(12) United States Patent
Sebok

(10) Patent No.: US 9,082,177 B2
(45) Date of Patent: Jul. 14, 2015

(54) METHOD FOR TRACKING X-RAY MARKERS IN SERIAL CT PROJECTION IMAGES

(75) Inventor: David Sebok, Eagleville, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 918 days.

(21) Appl. No.: 12/626,310

(22) Filed: Nov. 25, 2009

(65) Prior Publication Data

US 2011/0123080 A1     May 26, 2011

(51) Int. Cl.
  *G06K 9/00*       (2006.01)
  *G06T 7/00*       (2006.01)
  *A61B 6/00*       (2006.01)

(52) U.S. Cl.
  CPC .............. *G06T 7/0028* (2013.01); *A61B 6/583* (2013.01); *G06T 2207/10081* (2013.01); *G06T 2207/30036* (2013.01); *G06T 2207/30204* (2013.01)

(58) Field of Classification Search
  CPC ............ G06K 9/4604; G06K 9/00134; G06K 9/00369; G06T 7/2008; G06T 2207/10081; G06T 2207/30036; G06T 2207/30204
  USPC .................................................. 382/128–131
  See application file for complete search history.

(56) References Cited

U.S. PATENT DOCUMENTS

| | | | |
|---|---|---|---|
| 3,109,588 A | 11/1963 | Polhemus et al. | |
| 4,709,333 A | 11/1987 | Crawford | |
| 5,023,894 A | 6/1991 | Yamashita et al. | |
| 5,109,397 A | 4/1992 | Gordon et al. | |
| 5,339,367 A | 8/1994 | Roth | |
| 5,359,637 A | 10/1994 | Webber | |
| 5,442,674 A | 8/1995 | Picard et al. | |
| 5,668,844 A | 9/1997 | Webber | |
| 5,676,673 A | 10/1997 | Ferre et al. | |

(Continued)

FOREIGN PATENT DOCUMENTS

| CN | 1475971 | 2/2004 |
|---|---|---|
| CN | 101489033 | 7/2009 |

(Continued)

OTHER PUBLICATIONS

Lee, K.J., Kwon, D., Yun, I.D., Lee, S.U.: "Deformable 3d volume registration using efficient MRFS model with decomposed nodes", British Machine Vision Conference (2008).*

(Continued)

*Primary Examiner* — Robert Sorey
(74) *Attorney, Agent, or Firm* — Michael Best & Friedrich LLP

(57) ABSTRACT

A method and system of rapidly detecting and mapping a plurality of marker points identified in a sequence of projection images to a physical marker placed on a patient or other scanned object. Embodiments of the invention allow a marker physical mapping module executable by an electronic processing unit to obtain a sequence of images based on image data generated by a scanner. Each image in the sequence of images represents an angle of rotation by the scanner and includes a plurality of marker points each having a U position and a V position. Expected U and V positions for the physical marker are calculated and a list of candidate marker points is created based on the expected positions. The images are processed and selected candidate marker points are added to a good point list.

5 Claims, 38 Drawing Sheets

(56) References Cited

U.S. PATENT DOCUMENTS

| | | | |
|---|---|---|---|
| 5,769,789 A | 6/1998 | Wang et al. | |
| 5,771,306 A | 6/1998 | Stork et al. | |
| 5,871,445 A * | 2/1999 | Bucholz | 600/407 |
| 6,006,126 A * | 12/1999 | Cosman | 600/426 |
| 6,021,222 A | 2/2000 | Yamagata | |
| 6,081,577 A | 6/2000 | Webber | |
| 6,148,058 A | 11/2000 | Dobbs | |
| 6,243,439 B1 | 6/2001 | Arai et al. | |
| 6,246,900 B1 | 6/2001 | Cosman et al. | |
| 6,314,310 B1 | 11/2001 | Ben-Haim et al. | |
| 6,330,356 B1 | 12/2001 | Sundareswaran et al. | |
| 6,359,960 B1 | 3/2002 | Wahl et al. | |
| 6,370,271 B2 | 4/2002 | Fu et al. | |
| 6,385,632 B1 | 5/2002 | Choe et al. | |
| 6,405,072 B1 | 6/2002 | Cosman | |
| 6,484,048 B1 | 11/2002 | Hoshino et al. | |
| 6,549,607 B1 | 4/2003 | Webber | |
| 6,738,656 B1 | 5/2004 | Ferre et al. | |
| 6,766,056 B1 | 7/2004 | Huang et al. | |
| 6,856,827 B2 | 2/2005 | Seeley et al. | |
| 6,859,555 B1 | 2/2005 | Fang et al. | |
| 6,888,924 B2 | 5/2005 | Claus et al. | |
| 6,973,202 B2 | 12/2005 | Mostafavi | |
| 7,002,342 B2 | 2/2006 | Duerk et al. | |
| 7,027,618 B2 | 4/2006 | Trajkovic et al. | |
| 7,084,868 B2 | 8/2006 | Farag et al. | |
| 7,110,614 B2 | 9/2006 | Launay et al. | |
| 7,133,042 B2 | 11/2006 | Anh et al. | |
| 7,207,715 B2 | 4/2007 | Yue | |
| 7,221,728 B2 | 5/2007 | Edic et al. | |
| 7,239,908 B1 * | 7/2007 | Alexander et al. | 600/427 |
| 7,258,674 B2 | 8/2007 | Cribbs et al. | |
| 7,312,795 B2 | 12/2007 | Aso et al. | |
| 7,336,765 B1 | 2/2008 | Amiton et al. | |
| 7,340,108 B2 | 3/2008 | Florent et al. | |
| 7,426,256 B2 | 9/2008 | Rasche et al. | |
| 7,494,277 B2 | 2/2009 | Setala | |
| 7,499,576 B2 | 3/2009 | Setala | |
| 7,519,412 B2 | 4/2009 | Mistretta | |
| 7,532,705 B2 | 5/2009 | Yin et al. | |
| 7,545,909 B2 | 6/2009 | Singh et al. | |
| 7,591,793 B2 | 9/2009 | Orito et al. | |
| 7,646,899 B2 | 1/2010 | Fitzpatrick | |
| 7,796,787 B2 | 9/2010 | Wang et al. | |
| 7,991,107 B2 | 8/2011 | Sadakane et al. | |
| 8,116,544 B2 | 2/2012 | Masumoto | |
| 8,180,130 B2 | 5/2012 | Sebok | |
| 8,364,245 B2 * | 1/2013 | Kruecker | 600/426 |
| 8,559,691 B2 | 10/2013 | Borghese et al. | |
| 2002/0065461 A1 * | 5/2002 | Cosman | 600/426 |
| 2002/0085668 A1 | 7/2002 | Blumhofer et al. | |
| 2002/0109795 A1 | 8/2002 | Bruzzone et al. | |
| 2002/0122536 A1 | 9/2002 | Kerrien et al. | |
| 2003/0130576 A1 | 7/2003 | Seeley et al. | |
| 2003/0228044 A1 | 12/2003 | Gopalasamy et al. | |
| 2004/0114033 A1 | 6/2004 | Eian et al. | |
| 2004/0136590 A1 | 7/2004 | Brouwer | |
| 2005/0030076 A1 * | 2/2005 | Mohanavelu et al. | 327/165 |
| 2005/0059879 A1 | 3/2005 | Sutherland et al. | |
| 2005/0059887 A1 | 3/2005 | Mostafavi et al. | |
| 2005/0078861 A1 | 4/2005 | Usikov | |
| 2005/0165292 A1 | 7/2005 | Simon et al. | |
| 2006/0133564 A1 | 6/2006 | Langan et al. | |
| 2006/0147100 A1 | 7/2006 | Fitzpatrick | |
| 2006/0245628 A1 | 11/2006 | Jeung et al. | |
| 2007/0047794 A1 | 3/2007 | Lang et al. | |
| 2007/0076938 A1 | 4/2007 | Hartman et al. | |
| 2007/0106152 A1 * | 5/2007 | Kantrowitz et al. | 600/424 |
| 2007/0160270 A1 | 7/2007 | Arini et al. | |
| 2007/0221850 A1 | 9/2007 | Panin et al. | |
| 2007/0238947 A1 | 10/2007 | Pescatore et al. | |
| 2007/0253599 A1 | 11/2007 | White et al. | |
| 2007/0286470 A1 | 12/2007 | Bernard et al. | |
| 2007/0291895 A1 | 12/2007 | Yin et al. | |
| 2008/0021297 A1 | 1/2008 | Boosten | |
| 2008/0037853 A1 | 2/2008 | Bernard et al. | |
| 2008/0069418 A1 * | 3/2008 | Bystrov et al. | 382/131 |
| 2008/0075348 A1 | 3/2008 | Rappaport et al. | |
| 2008/0159612 A1 | 7/2008 | Fu et al. | |
| 2008/0221431 A1 * | 9/2008 | Steinmeyer et al. | 600/414 |
| 2008/0267455 A1 | 10/2008 | Grass et al. | |
| 2008/0267482 A1 * | 10/2008 | Abe et al. | 382/131 |
| 2009/0022266 A1 | 1/2009 | Stayman et al. | |
| 2009/0076369 A1 | 3/2009 | Mistretta | |
| 2009/0122866 A1 | 5/2009 | Crawford et al. | |
| 2009/0129634 A1 | 5/2009 | De Waele | |
| 2009/0169080 A1 | 7/2009 | Noordhoek | |
| 2009/0187096 A1 * | 7/2009 | Tiernan et al. | 600/421 |
| 2009/0268865 A1 | 10/2009 | Ren et al. | |
| 2010/0040274 A1 * | 2/2010 | Zhang et al. | 382/131 |
| 2010/0099979 A1 | 4/2010 | Schoonenberg et al. | |
| 2010/0254583 A1 * | 10/2010 | Chan et al. | 382/131 |
| 2010/0280375 A1 * | 11/2010 | Zhang et al. | 600/443 |
| 2011/0123080 A1 | 5/2011 | Sebok | |
| 2011/0123081 A1 | 5/2011 | Sebok et al. | |
| 2011/0123085 A1 | 5/2011 | Sebok et al. | |
| 2011/0123088 A1 | 5/2011 | Sebok et al. | |
| 2011/0176723 A1 | 7/2011 | Ali et al. | |
| 2013/0338492 A1 * | 12/2013 | Munro et al. | 600/424 |
| 2014/0253113 A1 | 9/2014 | Suzuki | |

FOREIGN PATENT DOCUMENTS

| | | |
|---|---|---|
| JP | 01212570 | 8/1989 |
| JP | 06142093 | 5/1994 |
| JP | 0759763 | 3/1995 |
| JP | 0810265 | 1/1996 |
| JP | 10145335 | 5/1998 |
| JP | 2000316837 | 11/2000 |
| JP | 2001017422 | 1/2001 |
| JP | 2001087283 | 4/2001 |
| JP | 2003132356 | 5/2003 |
| JP | 2003305032 | 10/2003 |
| JP | 2004363850 | 12/2004 |
| JP | 2005021345 | 1/2005 |
| JP | 2005021675 | 1/2005 |
| JP | 2005296340 | 10/2005 |
| JP | 2005319207 | 11/2005 |
| JP | 2005324015 | 11/2005 |
| JP | 2006231051 | 9/2006 |
| JP | 2007016220 | 1/2007 |
| JP | 2007316809 | 6/2007 |
| JP | 2007244737 | 9/2007 |
| JP | 2008142543 | 6/2008 |
| JP | 2010535051 | 11/2010 |
| JP | 2011253433 | 12/2011 |
| WO | 01/01859 | 1/2001 |
| WO | 01/52190 | 7/2001 |
| WO | 2007/102509 | 9/2007 |

OTHER PUBLICATIONS

Flask, C., et al. "A method for fast 3D tracking using tuned fiducial markers and a limited projection reconstruction FISP (LPR-FISP) sequence." Journal of Magnetic Resonance Imaging, vol. 14, Issue 5, p. 617-627 (2001).*

U.S. Appl. No. 12/626,197, filed Nov. 25, 2009, David Sebok.

U.S. Appl. No. 12/626,218, filed Nov. 25, 2009, David Sebok.

U.S. Appl. No. 12/626,268, filed Nov. 25, 2009, David Sebok.

Debrunner, Christian, et al., "Tomographic Reconstruction from an Uncontrolled Sensor Trajectory", IEEE, 0-7803-8388-5/04, pp. 1416-1419, 2004.

Marchant, T.E., et al., "Measurement of Inter and Intra Fraction Organ Motion in Radiotherapy Using Cone Beam CT Projection Images", Physics in Medicine and Biology, vol. 53, No. 4, pp. 1087-1098, Feb. 21, 2008.

Seslija, Petar, et al., "Feasibility of 3D Tracking of Surgical Tools Using 2D Single Plane X-Ray Projections", Progress in Biomedical Optics and Imaging—Proceedings of SPIE, vol. 6918, Medical Imaging 2008: Visualization, Image-Guided Procedures, and Modeling, San Diego, CA, Feb. 17-19, 2008.

(56) References Cited

OTHER PUBLICATIONS

Hannaford, Blake, et al., "Adaptive Linear Predictor Tracks Implanted Radiopaque Markers", IEEE Transactions on Biomedical Engineering, vol. BME-32, No. 2, pp. 117-125, Feb. 1985.
Owen, Rebecca, et al., "The Detectability and Localization Accuracy of Implanted Fiducial Markers Determined on In-Room Computerized Tomography (CT) and Electronic Portal Images (EPI)", Medical Dosimetry, vol. 33, No. 3, pp. 226-233, Elsevier, 2008.
Cucchiara, Rita, et al., "An Image Analysis Approach for Automatically Re-Orienteering CT Images for Dental Implants", Computerized Medical Imaging and Graphics, vol. 28, pp. 185-201, Elsevier, 2004.
Perrenot, Beatrice, et al., "Motion Compensation for 3D Tomographic Reconstruction of Stent in X-Ray Cardiac Rotational Angiography", IEEE, 0-7803-9577-8/06, pp. 1224-1227, ISBI 2006.
Mao, W., et al., "Fast Internal Marker Tracking Algorithm for Onboard MV and kV Imaging Systems", Medical Physics, vol. 35, No. 5, pp. 1942-1949, May 2008.
Pouliot, Sebastien, et al., "Automatic Detection of Three Radio-Opaque Markers for Prostate Targeting Using EPID During External Radiation Therapy", IEEE, 0-7803-6725-1/01, pp. 857-860, 2001.
International Search Report and Written Opinion in International Application No. PCT/US2010/046828 dated Oct. 20, 2010, 14 pages.
International Search Report and Written Opinion in International Application No. PCT/US2010/46830 dated Oct. 22, 2010, 12 pages.
International Search Report and Written Opinion in International Application No. PCT/US2010/046834 dated Oct. 25, 2010, 11 pages.
International Search Report and Written Opinion in International Application No. PCT/US2010/46836 dated Oct. 13, 2010, 15 pages.
International Search Report and Written Opinion in International Application No. PCT/US2010/046845 dated Oct. 18, 2010, 11 pages.
International Search Report and Written Opinion in International Application No. PCT/US2010/046847 dated Oct. 25, 2010, 14 pages.
Perrenot, Beatrice, et al., "Motion Correction for Coronary Stent Reconstruction from Rotational X-Ray Projection Sequences", IEEE Transactions on Medical Imaging, vol. 26, issue 10, pp. 1412-1423, Oct. 2007.
Aubry, Jean-Francois, et al., "Measurements of Intrafraction Motion and Interfraction Rotation of Prostate by Three-Dimensional Analysis of Daily Portal Imaging with Radiopaque Markers", International Journal of Radiation Oncology Biology Physics, vol. 60, No. 1, pp. 30-39, 2004.
Civco Medical Solutions, ISOLOC Software, available online at:<http://www.civco.com/oncology/localization/isoloc-software/>, available at least as early as Feb. 18, 2009.
Yue, Ning, et al., "A Method to Implement Full Six-Degree Target Shift Corrections for Rigid Body in Image-Guided Radiotherapy", Med. Phys., vol. 33, issue 1, pp. 21-31, Jan. 2006.
Canon, R.M., et al., "Analysis of Fiducial Markers Used for On-Line Verification in the External-Beam Radiotherapy of Patients with Cranial Tumours", Clinical and Translational Oncology, pp. 531-536, 2007.
Non-Final Office Action from the United States Patent and Trademark Office for U.S. Appl. No. 12/626,268 dated Apr. 15, 2011 (16 pages).
Office Action from the United States Patent and Trademark Office for U.S. Appl. No. 12/700,028 dated Oct. 12, 2012 (18 pages).
Office Action from the United States Patent and Trademark Office for U.S. Appl. No. 12/700,032 dated Sep. 11, 2012 (20 pages).
Notice of Allowance from the United States Patent and Trademark Office for U.S. Appl. No. 12/626,197 dated Oct. 2, 2012 (10 pages).
Hayashi, "Three Dimensional Analysis of Orthodontic Tooth Movement Based on XYZ and Finite Helical Axis System," Oct. 18, 2007, The European Journal of Orthodontic Advance Access, pp. 1-4.
Office Action from the Japanese Patent Office for Application No. 2012-541073 dated Aug. 30, 2013 (English Translation, 4 pages).
Office Action from the Korean Patent Office for Application No. 10-2012-7016387 dated Aug. 30, 2013 (English Translation and Original, 5 pages).
Office Action from the Japanese Patent Office for Application No. 2012-541074 dated Aug. 30, 2013 (English Translation, 3 pages).
Office Action from the Korean Patent Office for Application No. 10-2012-7016386 dated Aug. 23, 2013 (English Translation and Original, 5 pages).
Office Action from the Japanese Patent Office for Application No. 2012-541075 dated Aug. 20, 2013 (English Translation, 2 pages).
Office Action from the Korean Patent Office for Application No. 10-2012-7016513 dated Sep. 17, 2013 (English Translation and Original, 5 pages).
Office Action from the Japanese Patent Office for Application No. 2012-541076 dated Aug. 19, 2013 (English Translation, 2 pages).
Notice of Allowance from the United States Patent and Trademark Office for U.S. Appl. No. 13/716,860 dated Mar. 5, 2013 (20 pages).
Office Action from the United States Patent and Trademark Office for U.S. Appl. No. 12/700,032 dated Feb. 14, 2013 (24 pages).
Office Action from the United States Patent and Trademark Office for U.S. Appl. No. 12/700,028 dated Apr. 5, 2013 (25 pages).
Office Action from the United States Patent and Trademark Office for U.S. Appl. No. 12/626,218 dated Jun. 7, 2013 (14 pages).
First Office Action from the State Intellectual Property Office of the People's Republic of China for Application No. 201080062385.4 dated Apr. 30, 2014 (15 pages).
Korean Patent Office Action for Application No. 10-2012-7016328 dated Oct. 31, 2013 (7 pages, English translation included).
Manoharan, "Validation of PET/CT Dataset for radiation treatment planning", Master's Thesis, Louisiana State University and Agricultural and Mechanical College, 133 pages, 2004.
Sun et al., "Automatic Segmentation of Fiducial Marks Using Attribute-based Mathematical Morphology" Journal of Electronic Imaging, vol. 10, No. 2, pp. 560-566, 2001.
Wiersma et al., Combining kV and MV imaging for real-time tracking of implanted fiducial markers:, Medical Physics, vol. 35, No. 4, pp. 1191-1198, 2008.
Navab et al., Dynamic Geometrical Calibration for 3-D Cerebral Angiography, SPIE, vol. 2708, pp. 361-370, 1996.
Chinese Patent Office Action for Application No. 201080062365.7 dated Jan. 8, 2014 (14 pages).
United States Patent Office Notice of Allowance for U.S. Appl. No. 12/626,218 dated Feb. 21, 2014 (11 pages).
Japanese Office Action for Japanese Patent Application No. 2012-541074 dated Apr. 11, 2014 (3 pages).
Korean Office Action for Korean Patent Application No. 10-2012-7016387 dated Apr. 15, 2014 (7 pages).
Japanese Office Action for Japanese Patent Application No. 2012-541075 dated May 2, 2014 (1 page).
Japanese Notice of Allowance for Japanese Patent Application No. 2012-541076 dated May 29, 2014 (3 pages).
First Office Action for Chinese Patent Application No. 201080062135.0 dated Apr. 3, 2014 (11 pages).
Japanese Office Action for Japanese Patent Application No. 2012-541073 dated Apr. 11, 2014 (6 pages).
Chinese Patent Office Action for Application No. 201080062012.7 dated Jun. 18, 2014 (27 pages—with translation).
Notice of Allowance from the U.S. Patent and Trademark Office for U.S. Appl. No. 13/331,539 dated Aug. 6, 2014 (11 pages).
Office Action from the Korean Patent Office for Application No. 10-2012-7016387 dated Nov. 19, 2014 (5 pages).
Notice of Allowance from the Japanese Patent Office for Application No. 2012-541073 dated Dec. 3, 2014 (4 pages).
Office Action for Japanese Patent Application No. 2013-262534 dated Dec. 2, 2014 (2 pages).
Notice of Preliminary Rejection from the Korean Intellectual Property Office for Application No. 10-2015-7002525 dated Feb. 16, 2015 (6 pages).
2nd Office Action from The State Intellectual Property Office of the People's Republic of China for Application No. 201080062385.4 dated Mar. 9, 2015 (15 pages).

* cited by examiner

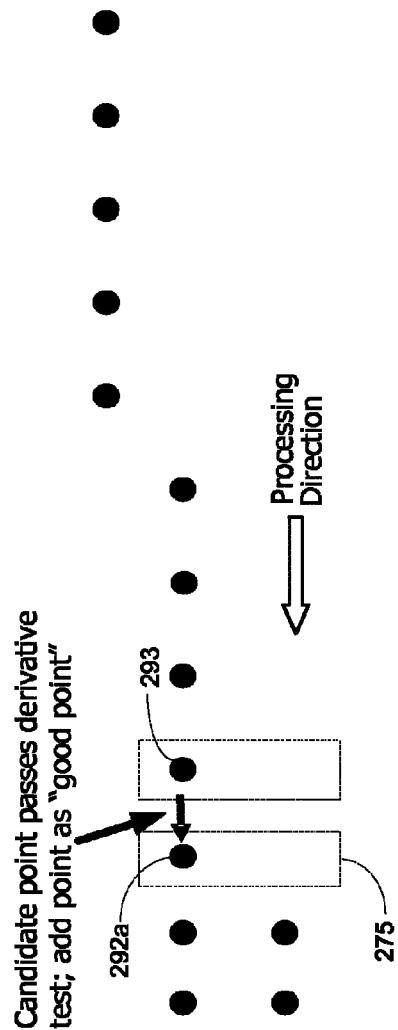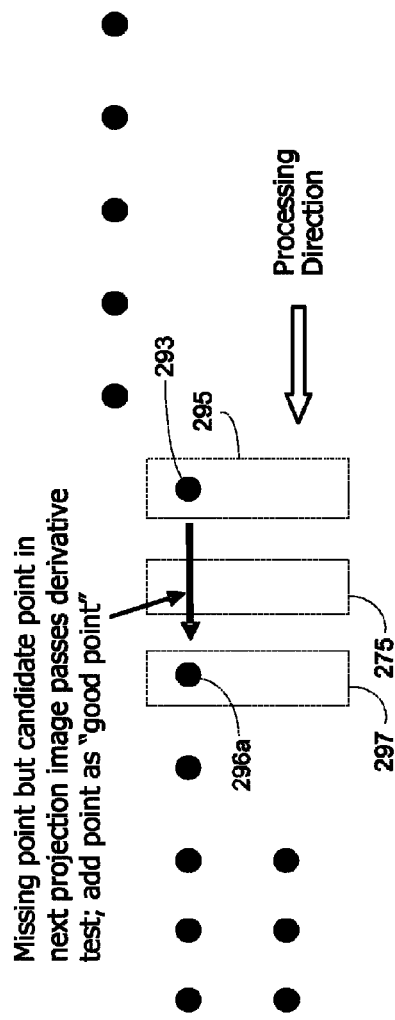

METHOD FOR TRACKING X-RAY MARKERS IN SERIAL CT PROJECTION IMAGES

BACKGROUND

Embodiments of the invention relate to image processing. In particular, embodiments provide methods and systems for detecting, localizing, and classifying marker-associated points located in x-ray images.

SUMMARY

Modern imaging systems acquire many images during a single procedure or scan. The images are combined using a process known as reconstruction to produce one or more images representing finite-width "slices" through a patient. Because the resulting images are often analyzed in preparation for medical or dental procedures or to properly calibrate the imaging equipment, it is important that the images be as clear as possible. However, patient movement during the scan can cause errors or blurring in the image.

Markers are often placed on a patient before an imaging procedure. The markers appear on the resulting image as marker points and are used to identify particular features in the image. The marker points can also be used to correct the images for patient movement. In a typical motion correction scenario, a relatively small number of markers (e.g., seven) must be identified in each of the hundreds (e.g., 600) or more images captured during the scan. Thus, using markers to detect and correct patient motion is practical only if the thousands of marker points (e.g., 4,200 marker points using the example above) can be automatically identified in the images. Marker point identification is further complicated by the non-linear nature of x-ray imaging and the relatively large dynamic range of x-ray images.

Yet another complication is that marker point identification and the resulting motion correction needs to be performed quickly because it must be completed before reconstruction of the images can begin. Existing methods for identifying marker-like points on images rely on the general circular nature of these points and employ point identification techniques such as image gradient processing or some variation of a Hough transform, which can take as long as 30 seconds per image to complete. Even the simplest methods can take 1/10 of a second or more per image and often take as long as five seconds per image.

The accuracy of these motion correction methods is directly related to the accuracy in extracting marker point locations. For example, in most correction methods the markers must be localized to a precision of 1/4 to 1/8 of a pixel. This degree of accuracy must be accomplished in the presence of a wide dynamic range of background values, a non-linear dependence on image background, and noise. Many existing correction methods do not properly deal with the non-linear nature of the image background, which leads to positional errors at image edges. These existing methods also do not work well when markers in images are relatively close to each other.

Once marker points are identified in an image they also need to be mapped back to the physical markers from which they originated. The physical markers are uniquely identified by their three-dimensional ("3D") positional coordinates. Thus, to make lists of points from each projection image associated with particular markers, one step is to identify each marker's physical location. This can be done by identifying the 3D location for each marker that is most consistent with how the position of the points produced by the marker changes from projection image to projection image as the gantry rotates. However, each marker's associated point locations may vary significantly from their expected locations because of patient movement or unplanned system or equipment movement. Therefore, the accuracy of identifying a marker's 3-dimensional coordinates suffers in the presence of noise or patient motion or when multiple markers are positioned close to each other. Existing techniques for identifying a marker's 3D location may use a position-dependent electromagnetic field that is detected by a remote sensor and is converted to a position. In addition to the complexity of this transmitter and sensor system, the technology used by the system depends on multiple sensors to determine a 3-dimensional position of a marker. Other localization techniques involve optical technologies that depend on knowledge of a fixed relationship between multiple detected sites, which increases the complexity of the technology.

Even after the physical markers associated with the image points are identified and a position is assigned to each, the problem still exists of assigning each point on each image to its source marker. Before this is done, all the points in all the images exist only as a single list. Point assignment (marker tracking) attempts to associate each marker point on each image with the marker that actually generated it. After point assignment is complete, each marker will possess a separate list of the marker points associated with that marker. Each marker's separate list may have only one or zero marker points at each projection image. It is important that the correct correspondence between markers and their associated marker points be maintained, even in the presence of motion and measurement error.

Embodiments provide systems and methods for rapidly identifying marker-associated points in an image, which can then be used in motion correction systems. One method includes processing each projection image to reduce the intensity of all objects but circular objects (i.e., the shape of the marker points), identifying local maxima in each image, growing the local maxima to create candidate regions, and applying circularity and projection continuity criteria to each candidate region. The method uses a sequence of applied simple mean filters, differences, and division/subtraction operations to reduce the intensity of all the objects but circular objects, in a manner which reduces the total image processing time by at least an order of a magnitude compared to other methods. One method includes obtaining an image, applying a 2-D high pass filter to create a background suppressed image, and extracting marker associated points from the background image.

Embodiments also provide systems and methods for performing accurate sub-pixel localization of marker point locations in an image. One method includes independently evaluating the position of each marker point identified in an image in each of the two dimensions. This evaluation is done by determining a background profile of each marker point by sampling one or both sides of a marker point. Taking a ratio of a baseline profile and the marker point profile corrects for background effects while addressing the non-linear nature of x-ray attenuation. Residual background offset is removed by subtracting the average value of tails of the marker point profile. Finally, the resulting marker point profile is evaluated to determine its first moment, which represents the marker point's location. Alternatively, the profile can be processed by fitting a theoretical marker point profile to the marker point profile using a positional fit parameter. This method determines the position of marker points in a projection image of a computer tomography scan with resolution significantly higher than that of the projection image pixel size. Furthermore, the method performs marker identification or localization in the presence of significant inhomogeneous background and adjacent structures. One method includes obtaining an image including a marker point, deriving a background corrected marker point profile, deriving a background and baseline corrected marker point profile, and defining a sub-pixel position of the marker point as a center of a peak of the background corrected marker point profile.

Embodiments also provide systems and methods for rapidly identifying and assigning an approximate 3D position to a marker associated with marker points on the images. One method includes taking the observed marker point's positional changes from projection image to projection image, and fitting the positional changes to theoretical projection trajectories defined by using different possible values of the ϕ, Z, and R cylindrical coordinates. This step includes defining a set of potential values for one or more of the cylindrical coordinate dimensions and selecting one of the values from the set. The method then determines the marker points in each projection image that fall within a range of distances from the trajectory defined by the selected value from the set. A metric is then assigned to each marker point falling in the range by finding the mean squared distance of each marker point from the boundaries of the trajectory range. The metric is summed for all marker points within the range to derive a single metric associated with the particular trial coordinate value set. These steps are repeated for each value in the set of potential coordinate values and the resulting values of the metric (as a function of coordinate values) are evaluated to determine function peaks, which are each assumed to represent a cluster of one or more markers. These coordinate values for the one or more cylindrical coordinates associated with the peaks are assigned to the corresponding derived physical markers. These steps are repeated for the remaining cylindrical coordinates until the markers have been assigned all three coordinates. Because of the nature of the metric fitting, it is possible to find the average marker location in the presence of noise and patient movement and extract and separate multiple markers that are positioned close to each other. One method includes obtaining a sequence of images, each image representing an angle of rotation of the scanner and having a first value and a second value. The method also includes analyzing the behavior of the first value of the marker point positions through the sequence of images to determine the radial distance of the marker and the angular position of the marker. The method also includes analyzing the behavior of the second value of the marker point positions through the sequence of images to determine the axial position of the marker.

Embodiments also provide systems and methods for assigning each marker point in each projection image to the single physical marker most likely to be associated with that marker point through a process called marker tracking. One method includes obtaining a sequence of images with a plurality of marker points and calculating an expected U and V position and range for the physical marker in each image. The method also includes selecting a physical marker and creating a list of candidate points made up of marker points that fall within a range of expected marker point locations in each projection image theoretically determined for that physical marker. The method further includes processing the list by subtracting the theoretical trajectory of the physical marker from the actual image location of each marker point in the list to assign an error from theoretical to each marker point. The method then traverses the list, projection-by-projection, and narrows the list to zero or one "good points" per projection image based on the first time derivatives between the errors of consecutive points in the candidate list in both the U and V directions and other criteria.

Other aspects of the invention will become apparent by consideration of the detailed description and accompanying drawings.

BRIEF DESCRIPTION OF THE DRAWINGS

FIG. 31 is a graphical illustration of processing a "next" projection image when the "next" projection image includes a single candidate marker point.

FIG. 32 is a graphical illustration of processing a "next" projection image when the "next" projection image includes no candidate marker points.

DETAILED DESCRIPTION

Figure 1:
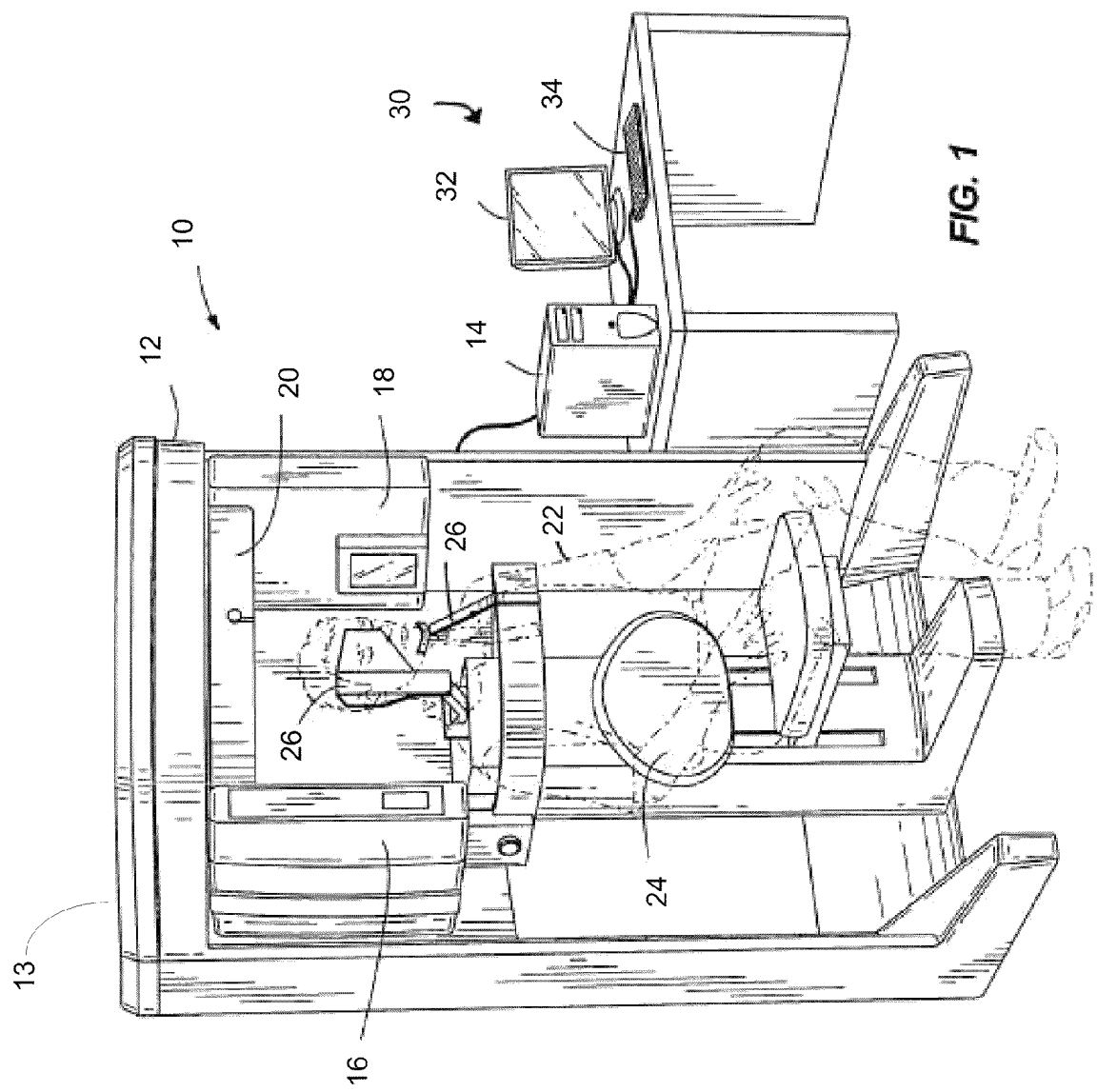
FIG. 1 schematically illustrates a cone-beam computed tomography system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It should also be noted that a plurality of hardware and software based devices, as well as a plurality of different structural components, may be utilized to implement the invention. Furthermore, and as described in subsequent paragraphs, the specific configurations illustrated in the drawings are intended to exemplify embodiments of the invention. Alternative configurations are possible.

X-rays are a form of radiation similar to light rays but are rays that can penetrate the human body. When x-rays pass through a human body, however, the intensity of the x-ray decreases. The amount of decrease in intensity is related to the density of the tissues through which the x-rays pass. This characteristic of x-rays is used to produce images of structures inside the human body and other subjects.

An x-ray system traditionally includes an x-ray tube that generates a diverging beam of x-rays. A person or subject is placed between the x-ray tube and a sheet of film that is sensitive to the intensity of the x-ray striking it at each location. The x-ray tube is turned on and off, the film is developed, and the resulting image presents a "shadow image" of the structures in the path of the x-ray with denser structures appearing whiter in the image.

Modern x-ray processes use one or more detectors rather than film. The detectors electronically detect and quantify the amount of (i.e., the intensity of) x-rays reaching the detector. Using the detectors, x-ray computed tomography ("CT") systems were created that rotate an x-ray source around a patient and electronically detect the resulting x-rays with a single-wide strip of detector elements on the side of the patient opposite from the x-ray source. The data from the detectors is collected for all the different x-ray positions and then combined in a process known as reconstruction. The combined images represent a single, finite-width "slice" through the patient where the image's intensity at each point represents the x-ray density of the tissue at a particular physical location. The combination of the x-ray source, the detectors, and the mechanical structure that allows rotation of the x-ray source is known as the "CT gantry."

Multiple slices can be acquired by repeating the process while moving the patient, the x-ray source, or both between image acquisitions or scans. For example, moving the table supporting the patient while also rotating the x-ray source produces a "helix" instead of a slice of data. In addition, increasing the size or width of the detector strip or ring from a signal row of detectors to multiple rows (e.g., up to 256 rows) allows for more rapid acquisition of more data. Furthermore, replacing the detector strip with a larger two-dimensional detector acquires an entire detector panel image at each x-ray source position rather than just a single strip of data. The collections of these images, which can number 600 or more, are known as projection images. Each projection image represents an x-ray snap-shot of the patient from a different perspective or angle as the x-ray source and the detector are rotated in synchronization around the patient. Because of the cone-shaped x-ray beam needed to cover the two-dimensional detector, this type of CT imaging is known as cone-beam ("CB") CT imaging. FIG. 1 schematically illustrates a CB CT imaging system 10 according to one embodiment of the invention.

The CB CT imaging system 10 includes a scanner 12 and a computer 14. The scanner 12 includes a CT gantry 13 which includes an x-ray source 16, a detector 18, and a rotating carrier 20. The x-ray source 16 and the detector 18 are aligned across from each other on the rotating carrier 20, which moves the x-ray source 16 and the detector 18 around a patient 22. The patient 22 is supported by a seat 24. The imaging system 10 illustrated in FIG. 1 is a dental imaging system. Therefore, the patient 22 sits in the seat 24 and places his or her chin into a rest 26. The rest 26 holds the patient's head relatively still while the gantry 13 is rotated to complete a scan of the patient's head.

The scanner 12 outputs image data to the computer 14. The image data represents the intensity levels of x-rays detected by the detector 18 during the scan. The computer 14 is connected to a console 30, which includes a display 32 and one or more input and/or output devices, such as a keyboard 34. A user uses the console 30 to interact with the computer 14. For example, a user can use the console 30 to request images or other data from the computer 14. The computer 14 provides the requested information to the console 30, and the console 30 displays the information on the display 32, prints the information to a printer (not shown), and/or saves the information to a computer-readable memory module (not shown).

Figure 2:
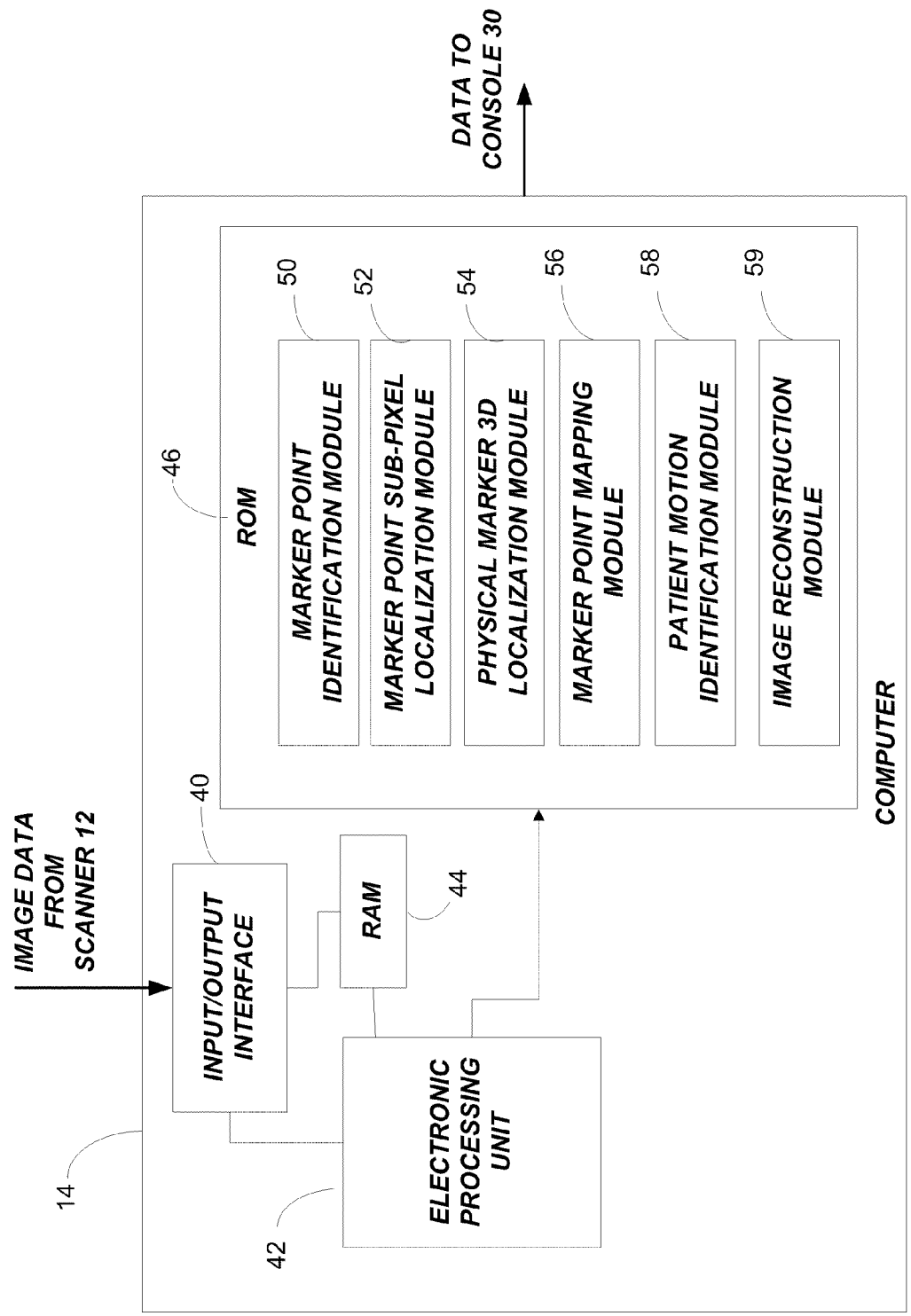
FIG. 2 schematically illustrates the computer of FIG. 1.

FIG. 2 schematically illustrates the computer 14 of FIG. 1 according to one embodiment of the invention. The computer 14 includes an input/output interface 40, an electronic processing unit ("EPU") 42, and one or more memory modules, such as a random access memory ("RAM") module 44 and a read-only memory ("ROM") module 46. The input/output interface 40 receives image data from the scanner 12 and provides the image data to the EPU 42. In some embodiments, the input/output interface 40 stores the image data to a memory module, such as the RAM module 44, and the EPU 42 obtains the image data from the memory module for processing. The input/output interface 40 may also transmit data to the scanner 12, such as calibration and operational data or instructions.

The EPU 42 receives the image data and processes the information by executing one or more applications or modules. In some embodiments, the applications or modules are stored in memory, such as the ROM module 46. In other embodiments, the applications or modules may be stored on a hard disk storage unit and transferred to RAM for execution. As shown in FIG. 2, the ROM module 46 stores a marker point identification module 50, a marker point sub-pixel localization module 52, a physical marker three-dimensional ("3D") localization module 54, a marker point mapping module 56, a patient motion identification module 58, and an image reconstruction module 59. The EPU 42 retrieves and executes the marker point identification module 50 to identify marker points in the received image data (see FIGS. 4-10). The EPU 42 retrieves and executes the marker point sub-pixel localization module 52 to provide accurate sub-pixel localization of marker point locations (see FIGS. 11-17). The EPU 42 retrieves and executes the physical marker 3D localization module 54 to determine three-dimensional locations of the physical markers identified through their marker points in the projection images (see FIGS. 18-23). The EPU 42 retrieves and executes the marker point mapping module 56 to map marker points identified in the projection images to particular physical markers (see FIGS. 24-33). The EPU 42 retrieves and executes the patient motion identification module 58 to derive patient motion information. The EPU 42 retrieves and executes the image reconstruction module 59 to combine the projection images with the motion information and produce a set of motion-corrected axial images.

Complete gantry rotation takes approximately eight to 40 seconds. During this time, a patient may move, which causes blurring of the resulting images. Typical image resolution is on the order of 0.25 millimeter. Therefore, patient motion of this same order often causes image blurring and extensive patient movement can make the resulting images unacceptable for their intended clinical purpose.

The computer 14 (see FIG. 2) can correct the images for patient movement by tracking the movement of rigid objects in the resulting images. For example, in ideal conditions, where there is no patient movement, imaged rigid objects change location in the two-dimensions of the projection images in a well-defined way as the gantry rotates around the patient. Deviation between the expected locations of objects in the image is caused by patient movement. By measuring a well-defined object's deviations from its expected locations, the amount of patient motion can be measured and corrected. In particular, if at least three objects are present in an image, the measured deviations of the objects from their expected locations can be combined to determine a six-parameter patient position error value (e.g., a patient motion vector), which can be applied to the images to correct for the patient movement.

To ensure that the desired number of well-defined, rigid objects are present in the images, one or more fiducial markers are placed on a patient. The markers typically consist of lead or steel BBs, which are dense and prevent or limit x-rays from passing through. The markers may be made from other materials and constructed in other forms or shapes that are visible in a high proportion of projection images generated during a scan. Each marker or multiple markers may be positioned between layers of adhesive and the adhesive can be applied to a patient to ensure that the markers do not move during the procedure.

The markers are placed on a patient such that each field of view or image created by the CB CT imaging system includes at least three marker points. For example, seven to nine markers may be placed on the patient to ensure that at least three marker points are within each image created by the CB CT imaging system, to decrease the position measurement noise, and to allow statistical combination of the results. In some embodiments, the markers are evenly spaced to have a maximal spatial distribution about the patient and to avoid interfering with normal image interpretation.

Identifying Markers in an Image

Figure 3:
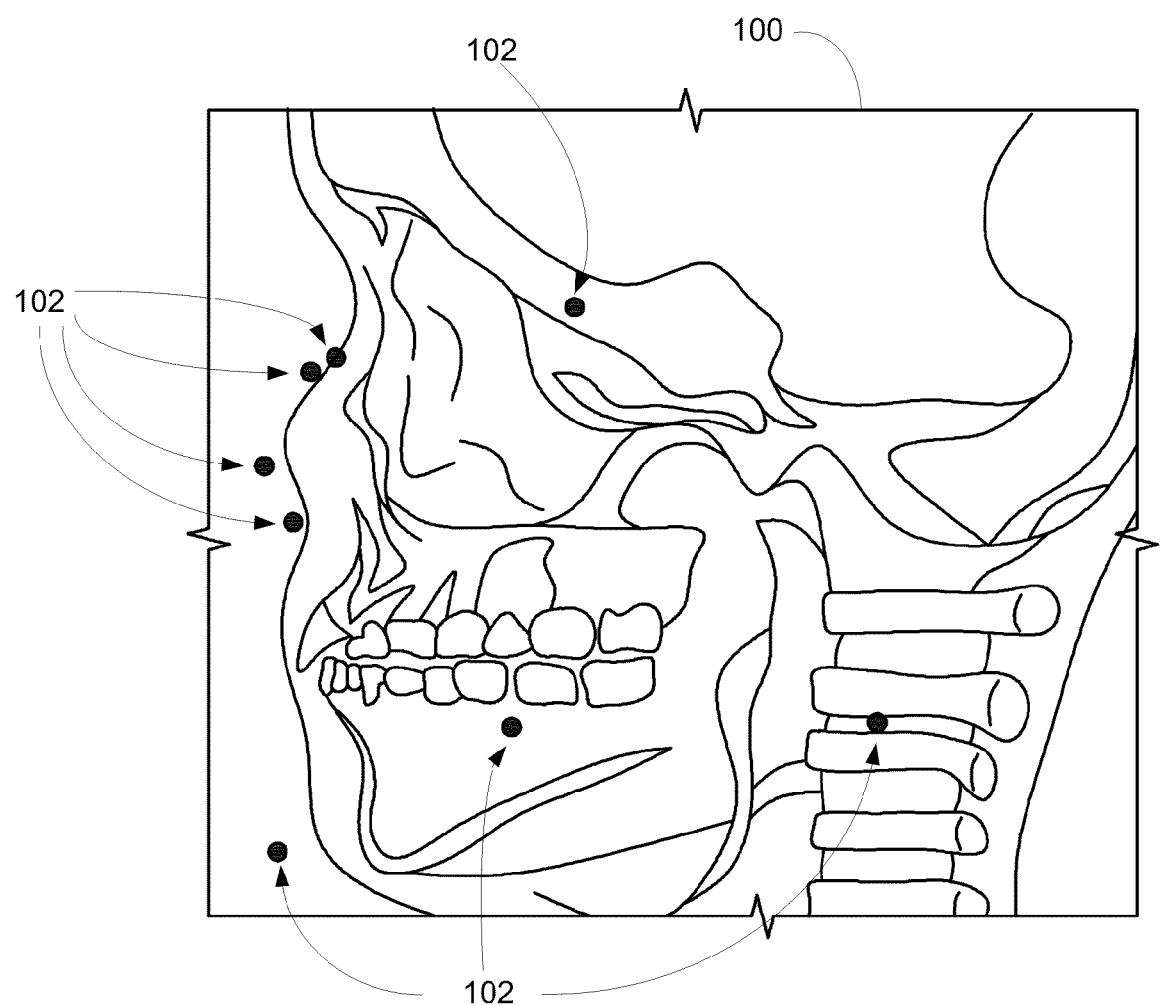
FIG. 3 illustrates an image including numerous marker points.
Figure 4:
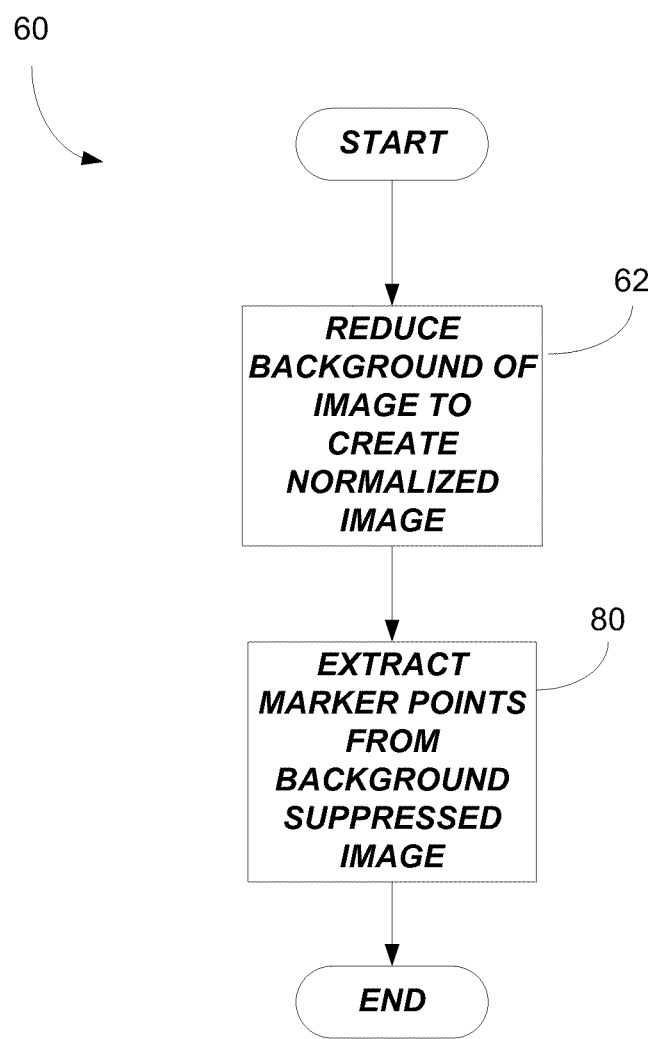
FIG. 4 is a flow chart illustrating a marker point identification method.

After the markers are placed on the patient, a scan is made of the patient, such as the patient's head, and the resulting image data representing a sequence of projection images is transmitted to the computer 14 (see FIG. 2). FIG. 3 illustrates an example projection image 100 that includes eight marker points 102. As an initial step in correcting the generated projection images for patient movement, the computer 14 processes the generated projection images to identify the marker points in each image. FIG. 4 illustrates a marker point identification method 60 according to one embodiment of the invention. The marker point identification method 60 is performed by the EPU 42 of the computer 14 when the EPU 42 executes the marker identification module 50.

As shown in FIG. 4, the first step of the method 60 generally includes reducing the intensity of the background of each projection image (step 62). This background suppression step minimizes the background portion of the image. The background portion of the image includes everything in the image other than the marker points. Because the fiducial markers have a well-defined shaped (i.e., a spherical or circular shape), step 62 minimizes everything in the image that does not have this well-defined shape.

In some embodiments, background suppression is accomplished by applying a linear high-pass filter to each image. In order to obtain acceptable speed, three optimizations are performed. First, the high-pass operation is accomplished by combining the original image with a low-pass filtered image. Secondly, instead of performing the filter simultaneously in the two image directions, a one dimensional high-pass operation is sequentially applied to the image in two or more dimensions (i.e., at 0°, 45°, 90°, and 135°). Finally, the low-pass filter operation is accomplished with a simple mean filter implemented with a cumulated pixel approach described below.

A one-dimensional high-pass filter operation will tend to accentuate areas of rapid change in the direction of the filter. A sequence of such operations performed in different directions will tend to accentuate circular objects over all other shapes. Since the marker points produced by the markers are circular, this sequence of filtering will accentuate the marker points and attenuate any surrounding structures.

Figure 5:
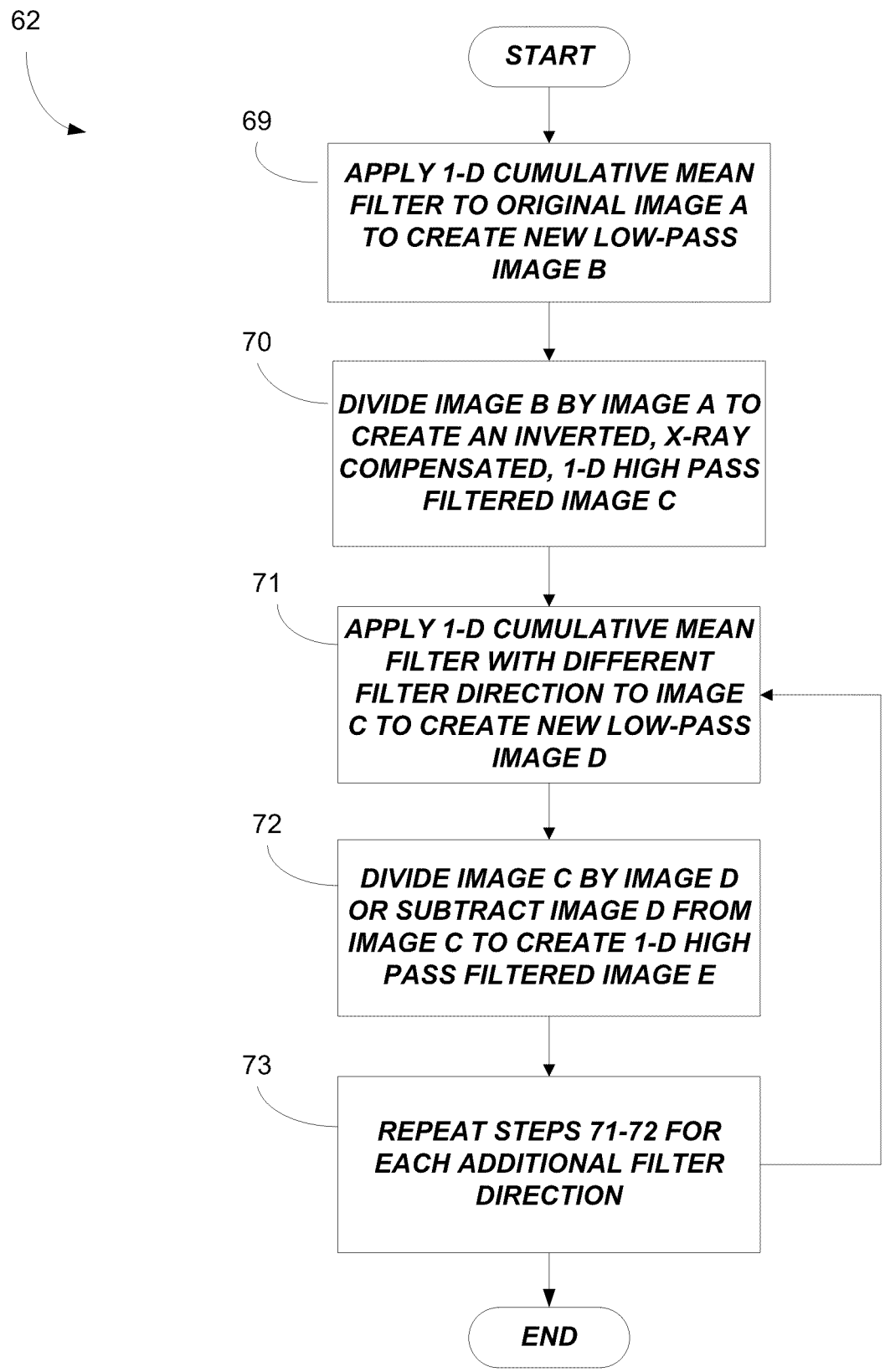
FIG. 5 is a flow chart illustrating a background reduction process of the marker point identification method of FIG. 4.
Figure 6:
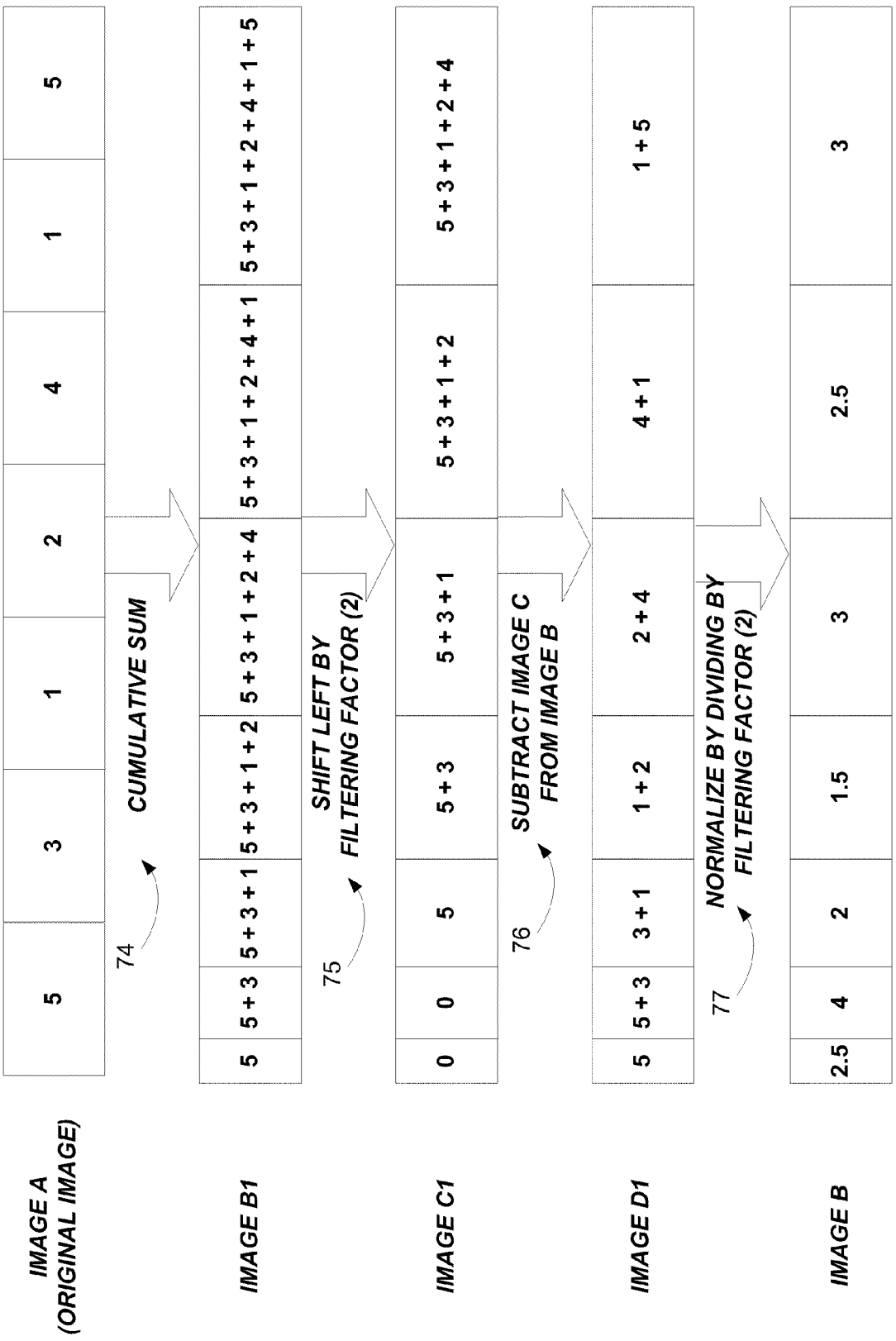
FIG. 6 is a graphical illustration of a process used to rapidly mean-filter the image in one dimension that is part of the background reduction process of FIG. 5.

FIG. 5 illustrates the process or steps involved in the reduction of background step 62. As shown in FIG. 5, the multi-dimensional high-pass filtering operation is executed by first performing simple one-dimensional, cumulative mean, low-pass image filtering on the original image A (step 69) to create filtered image B. Then, the filtered image B is combined with the original image A to create image C (step 70) as described below. These two steps are repeated for each filtering direction using the output image from the previous filtering step as the input to the next filtering step (steps 71-73). The process shown in FIG. 5 allows for rapid, multi-dimensional, high-pass filtering to reduce the background of the image. FIG. 6 illustrates an example of these steps involved in one-dimensional low-pass filtering in one direction.

Figure 5A:
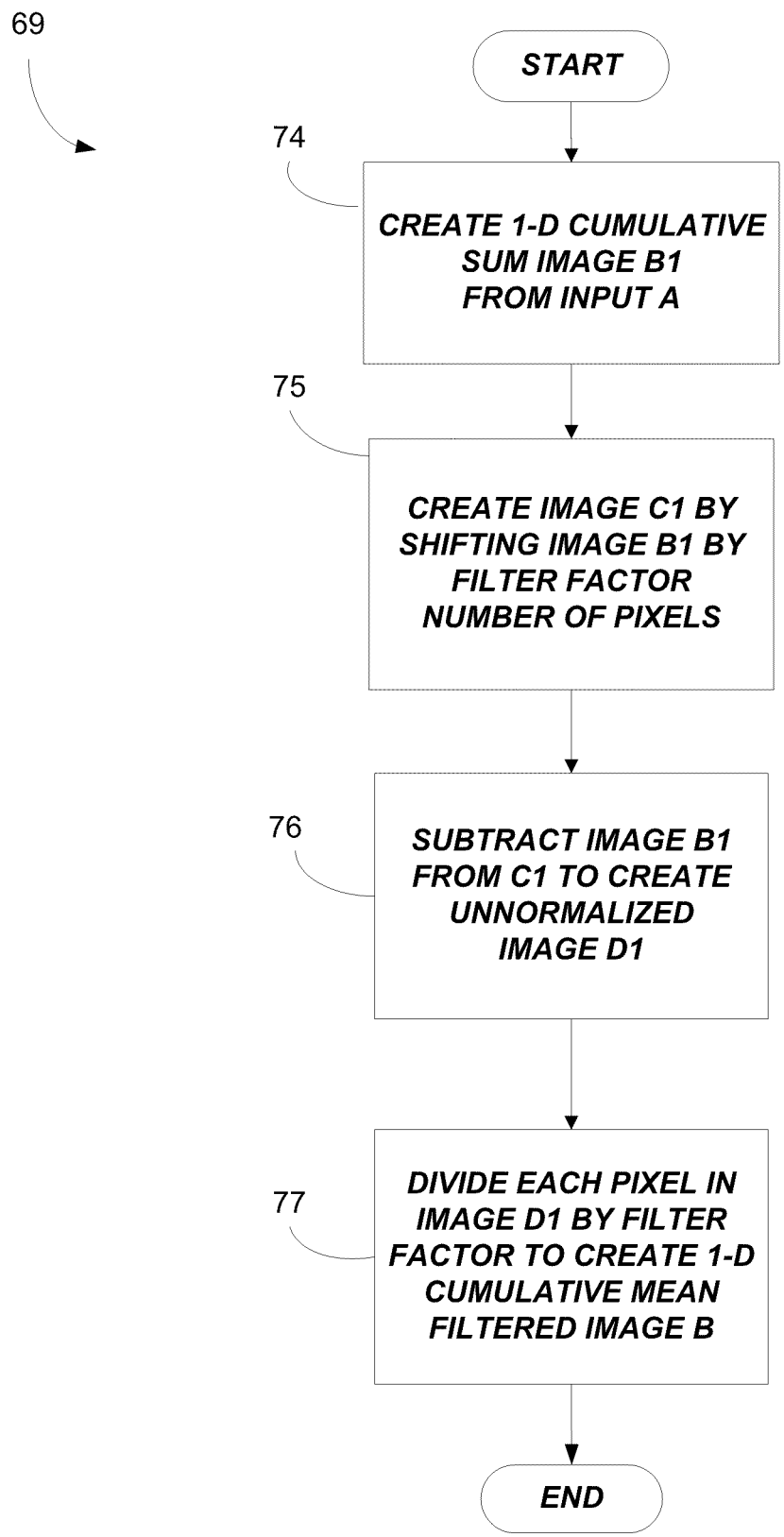
FIG. 5A is a flow chart illustrating an application of a 1-D cumulative mean filter.

Rather than using a more typical kernel-based filtering approach, the filtering of steps 69 and 71 is accomplished much more rapidly by using a cumulative mean filter (depicted in FIG. 5A). This rapid filtering is accomplished by creating a new image (image B1) where each pixel of the new image is set to the cumulative sum of all pixel values from the original image A from the particular pixel down to the first pixel in the direction of the filter (step 74). For example, as shown in FIG. 6, when the computer 14 initially obtains an original image (image A) from the scanner 12, the method considers one row of image A that includes seven pixels (where the processing direction is horizontal), then a cumulative image (image B1) is created by setting each pixel in this row to the sum of the pixel values to the pixel's left plus this pixel's value.

Once the cumulative image is generated at step 74, image B1 is shifted by an amount equal to the low-pass filtering factor (e.g., 2) to create a shifted image (image C1) (step 75). Image edges are handled by simply zeroing shifted edge pixels. For example, as shown in FIG. 6, each pixel in the cumulative image (image B1) is shifted two positions to the left to create the shifted image (image C1). Because there are no pixels two positions left of the first two pixels (i.e., the edge pixels), these pixels are set to 0.

The shifted image (image C1) is then subtracted from the cumulative image (image B1) to create a difference image (image D1) (step 76). As shown in FIG. 6, to subtract the images, each pixel value in the shifted image (image C1) is subtracted from the corresponding pixel value in the unshifted cumulative image (image B1). The final step is to normalize the difference image (image D1) by dividing each pixel in it by the filter factor (shift value) to produce the low-pass filtered image B (step 77).

The computation time for steps 74-77 is independent of the kernel size of the low-pass filter. The computations in these steps involve roughly 2×N additions and subtractions instead of (kernel size)×N operations, which are typically needed for a normal kernel-based filter. For an image of 512×512 pixels and a typical smoothing factor of 15, this represents a decrease in computation time versus a traditional 1-D kernel approach of 7.5:1. Compared to a 2-D kernel, (versus two 1-D cumulative mean filter operations) for a filter factor of 15, the speed improvement is 56:1.

After the one-dimensional low-pass filtered image is created, a high-pass filtered image (image C) is created by combining the low-pass image (image B) with the image used to generate it (image A) (step 73). This could be done by a simple difference operation between the two images. However, a division operation is used for the processing in the first direction filtering step 70. Division is used to compensate for the exponential nature of x-ray attenuation and normalized image (image B) to create image C (step 70). Dividing the difference image is effective because x-ray attenuation occurs as a negative exponent of the material density. Therefore, because division is the equivalent of subtracting logs followed by exponentiation, dividing the difference image avoids the computationally expensive log and exponentiation operations.

Figure 7:
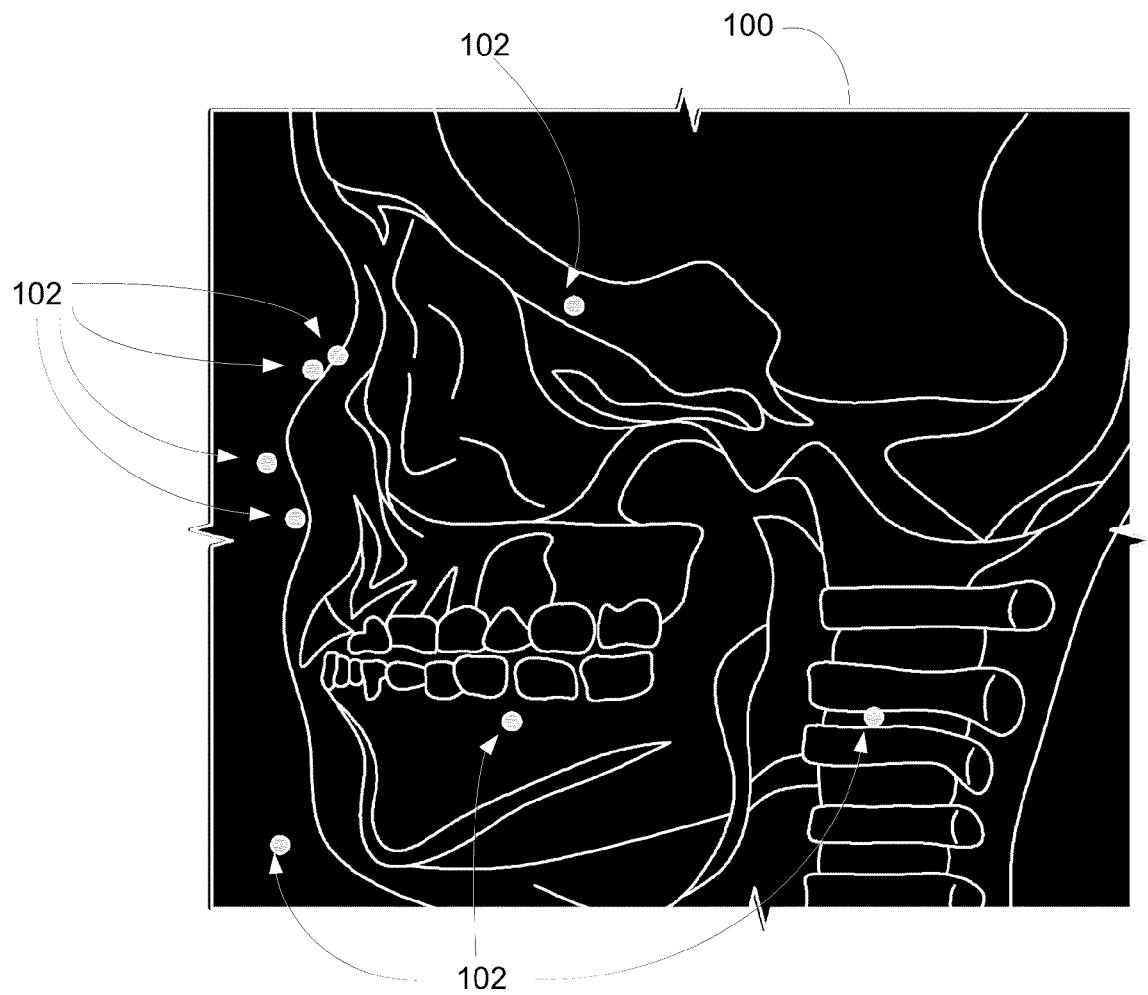
FIG. 7 illustrates the image of FIG. 3 after applying the background reduction process of FIG. 5.

The process of applying the one-dimensional, cumulative-mean, low-pass filter and combining the input and output images is repeated in each of the successive dimensions (step 71-73). However, after the first dimension is processed, a subtraction may be used instead of division at step 72 because correction for the exponential nature of x-ray attenuation is completed by the division performed when the first dimension is processed (step 70). Typically, four passes at 0, 45, 90, and 135 degrees are sufficient to obtain proper isolation of spherical-shaped marker points from a wide range of backgrounds. FIG. 7 illustrates the image 100 of FIG. 3 after applying the background reduction method of FIG. 5. As shown in FIG. 7, the majority of the background (i.e., the portions of the image other than the marker points 102) has been reduced or darkened, which allows the marker points 102 to be more easily identified.

Figure 8:
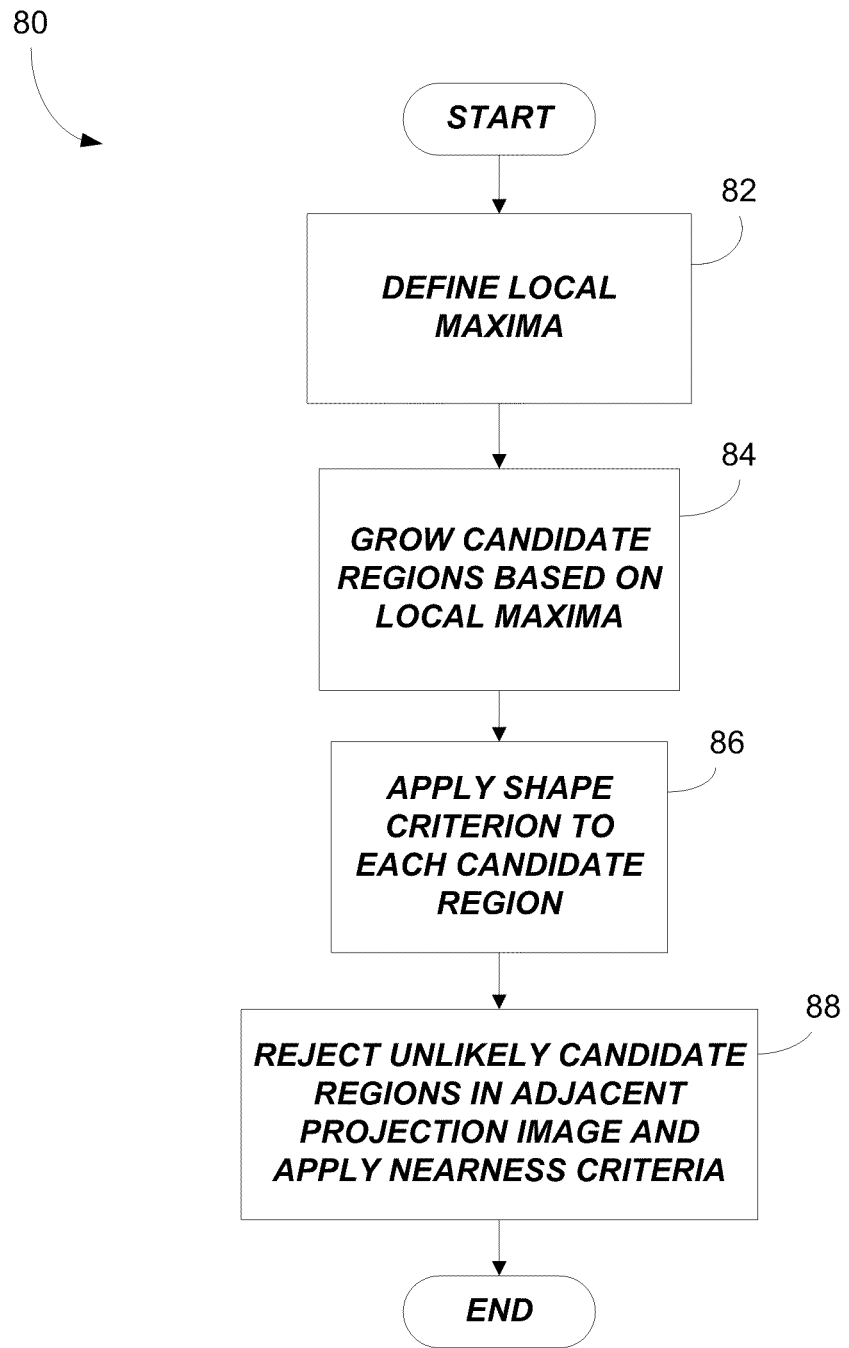
FIG. 8 is a flow chart illustrating a marker point extraction process of the marker point identification method of FIG. 4.
Figure 9:
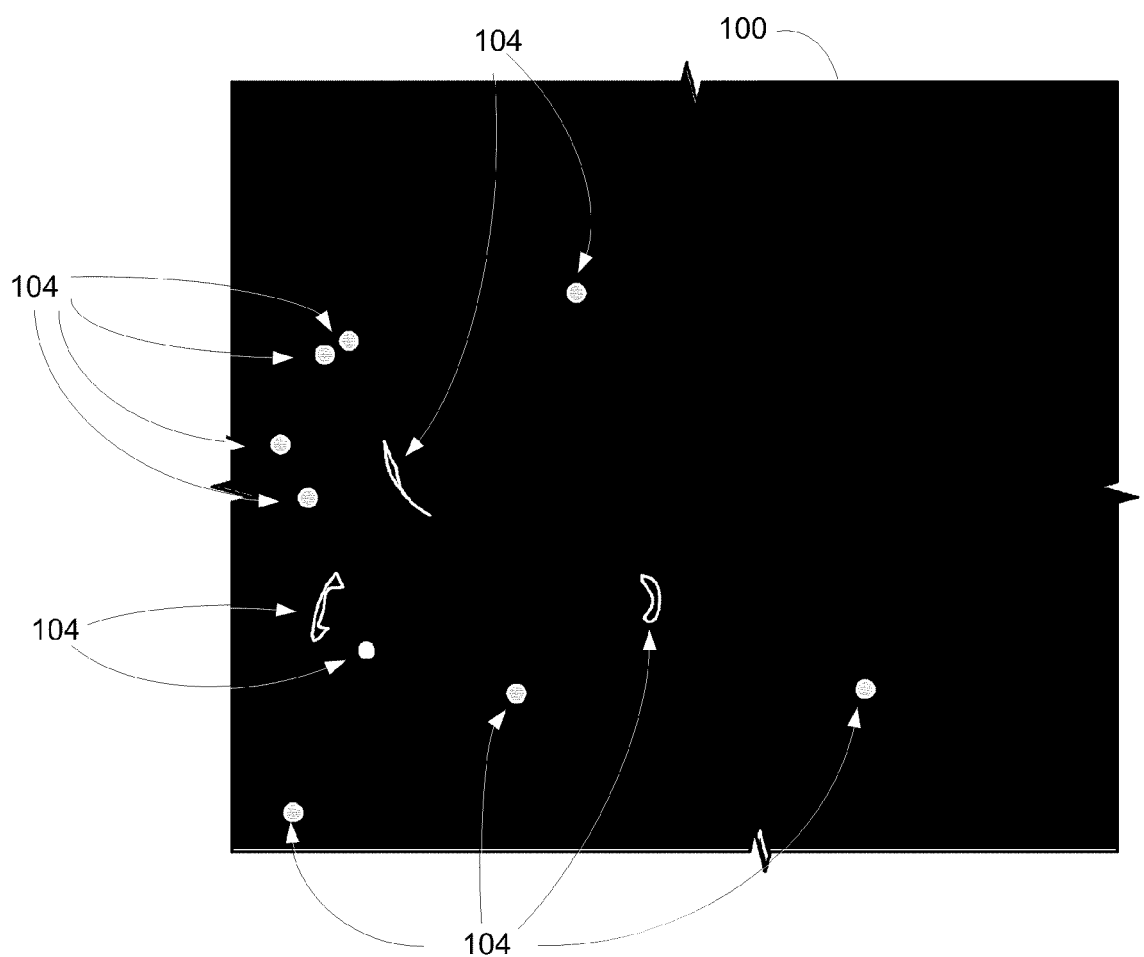
FIGS. 9 and 10 illustrate the image of FIG. 7 after performing the steps of the marker point extraction process of FIG. 8.

Returning to FIG. 4, once the background is reduced through the above steps, the marker points are extracted from the high-pass filtered image (step 80). FIG. 8 illustrates the process or steps of extracting the marker points from the high-pass image. As shown in FIG. 8, the process starts by defining the local maxima in each high-pass image (step 82). This step includes identifying each pixel in each image in which all 8 of the pixel's neighboring pixels have values smaller than it. Next, the identified local maxima are used as seed points to grow regions (step 84). This process combines the local maxima contained within a particular region into a single candidate object or region. In some embodiments, the size or extension of the generated regions is limited by an empirically-specified lower value threshold. FIG. 9 illustrates the image 100 of FIG. 7 after region growing the local maxima (steps 82 and 84), which creates candidate regions 104.

At step 86, a shape criterion is applied to each candidate region to identify which regions are most likely to represent marker points. In some embodiments, this process is performed by taking the ratio between (1) the pixel area of the candidate region (a) and (2) an area defined by the square of the mean radius of the candidate region times pi ((mean radius of a)$^2*\pi$). The value of this ratio is used to determine whether the candidate region is the proper shape to be a marker point (e.g., whether the candidate region has a circular shape).

Figure 10:
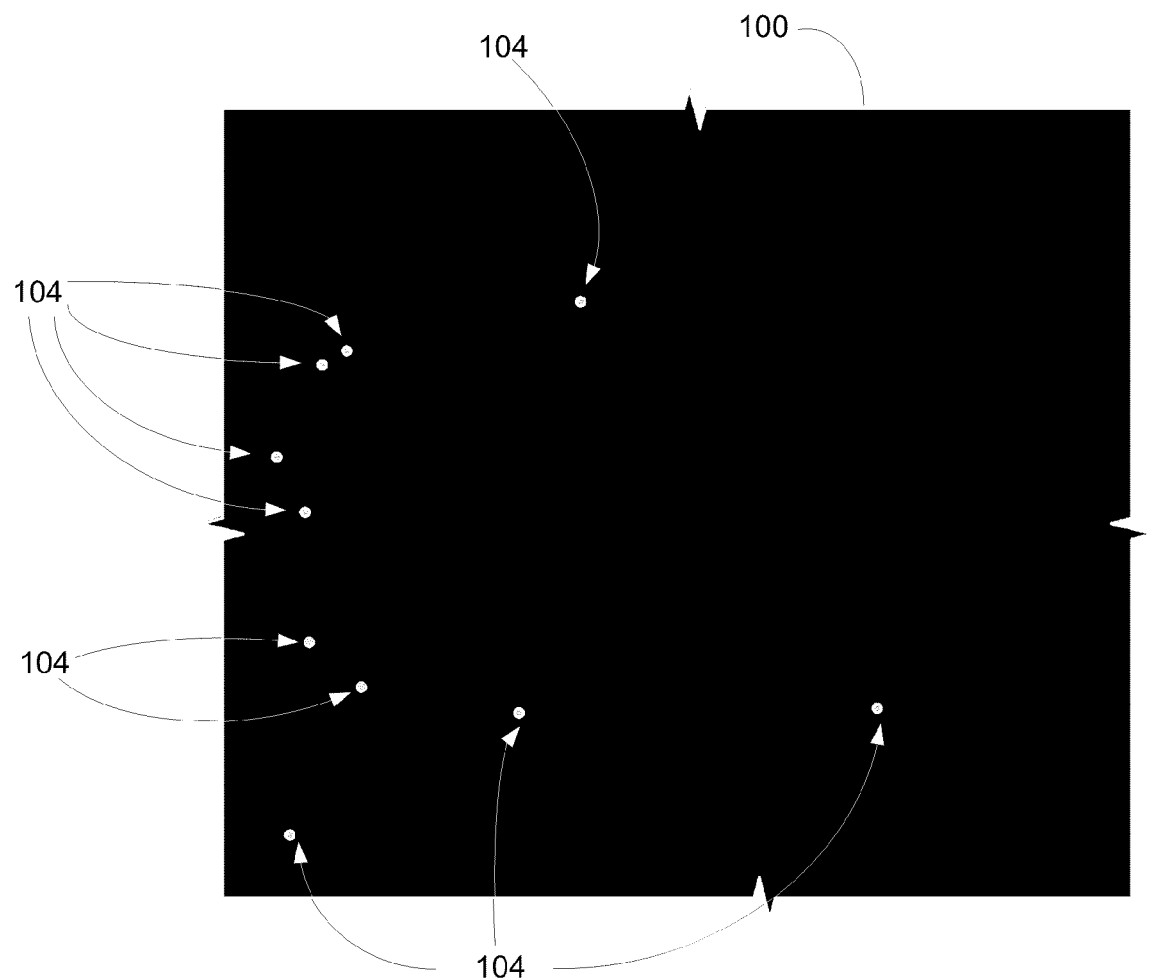

Finally, at step 88, the candidate regions are further processed to reject unlikely candidates by comparing the location of candidate regions in adjacent projection images and applying a nearness criterion. For example, if a candidate region moves too much in its position between sequential projection images, it is unlikely that the candidate region represents a marker point. Similarly, if two candidate regions are too close together, it is unlikely that the regions represent marker points. FIG. 10 illustrates the image 100 of FIG. 9 after applying the shape criterion to the candidate regions 104 and rejecting unlikely candidate regions 104 (steps 86 and 88). As shown in FIG. 10, after these steps only candidate regions 104 corresponding to the eight marker points 102 (see FIGS. 7 and 8) remain.

In some embodiments, applying a two-dimensional high-pass filter to an image includes first applying a two-dimensional low-pass filter to the image to create a low-pass image. Thereafter, the original image is combined with the low-pass image.

In some embodiments, the marker identification method 60 can be performed in times on the order of less than 50 milliseconds per image. In addition, when spherical markers are used, the marker point identification method 60 exhibits a high selective rate for markers and a high rejection rate for non-marker associated structures. For example, in some embodiments, the marker point identification method 60 can have a 100% sensitivity and a better than 40:1 specificity (less than 2.5% false detections) in real-world situations.

Determining a Sub-Pixel Center Point of a Marker

Figure 11:
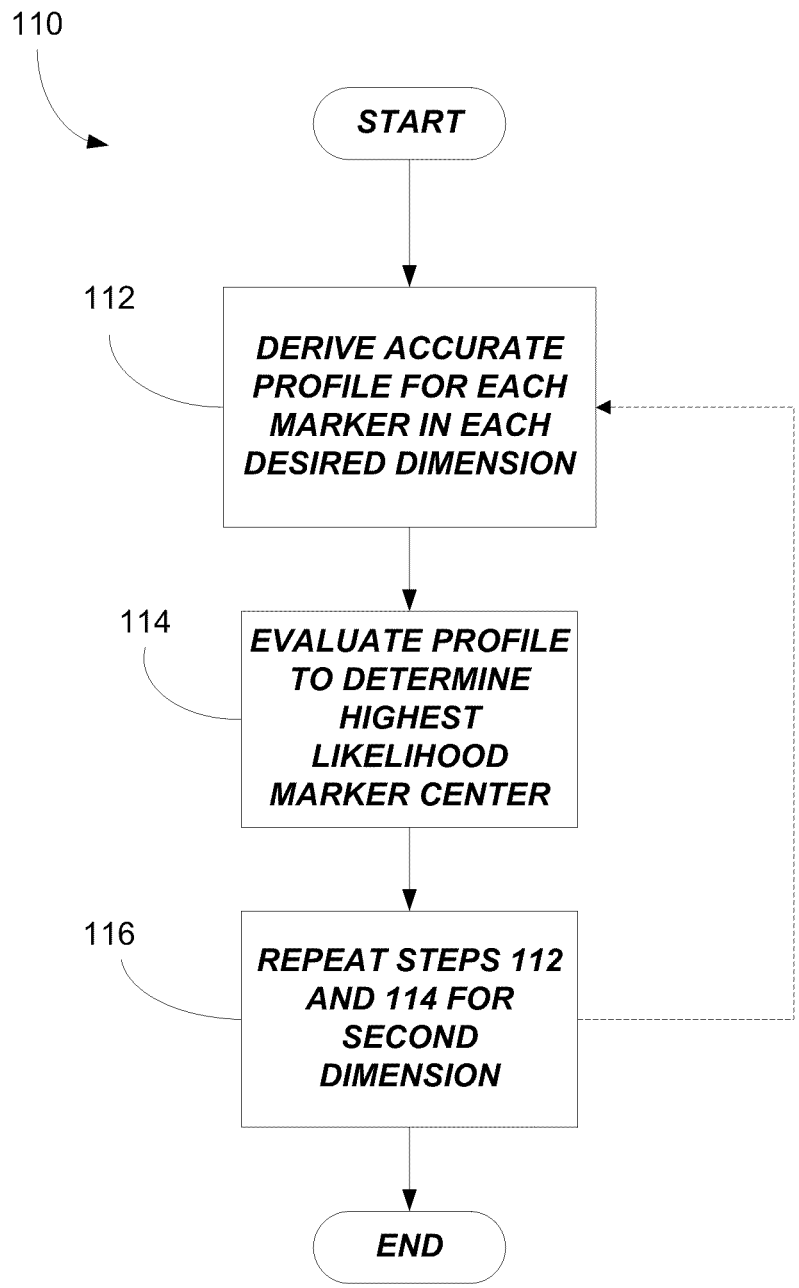
FIG. 11 is a flow chart illustrating a marker point sub-pixel localization method.

Even after the marker points are identified in the images using the marker point identification method 60, the marker points may need to be further or more accurately defined before they can be used to perform motion correction. In particular, it may be necessary to know the effective 2-dimensional position of the marker points to a resolution much better than the pixel resolution (sub-pixel) provided by the marker point identification method 60. A resolution as small as ⅛ of the pixel resolution may be needed. Again, this must be done in the presence of greatly varying background both within the images and from image to image. FIG. 11 illustrates a marker point sub-pixel localization method 110 according to one embodiment of the invention. The marker point sub-pixel localization method 110 is performed by the EPU 42 of the computer 14 when the EPU 42 executes the marker point sub-pixel localization module 52. In some embodiments, the marker point sub-pixel localization method 110 uses marker points identified by the marker point identification method 60 as a starting point to determine accurate sub-pixel marker locations as described below.

As shown in FIG. 11, the marker point sub-pixel localization method 110 generally includes a marker point profile derivation process (step 112) and a marker point center determination process (step 114), which are repeated for each of the two dimensions of the projection image (step 116). As described in more detail below (see FIGS. 12-14), the marker point profile derivation process 112 applies a sequence of steps to remove the majority of the background and generate multi-pixel marker point profiles in each desired dimension. In the marker point center determination process 114, the generated marker point profiles are compared to the expected shape of the marker and one-dimensional sub-pixel marker point center locations are derived (see FIGS. 15-16).

Figure 12:
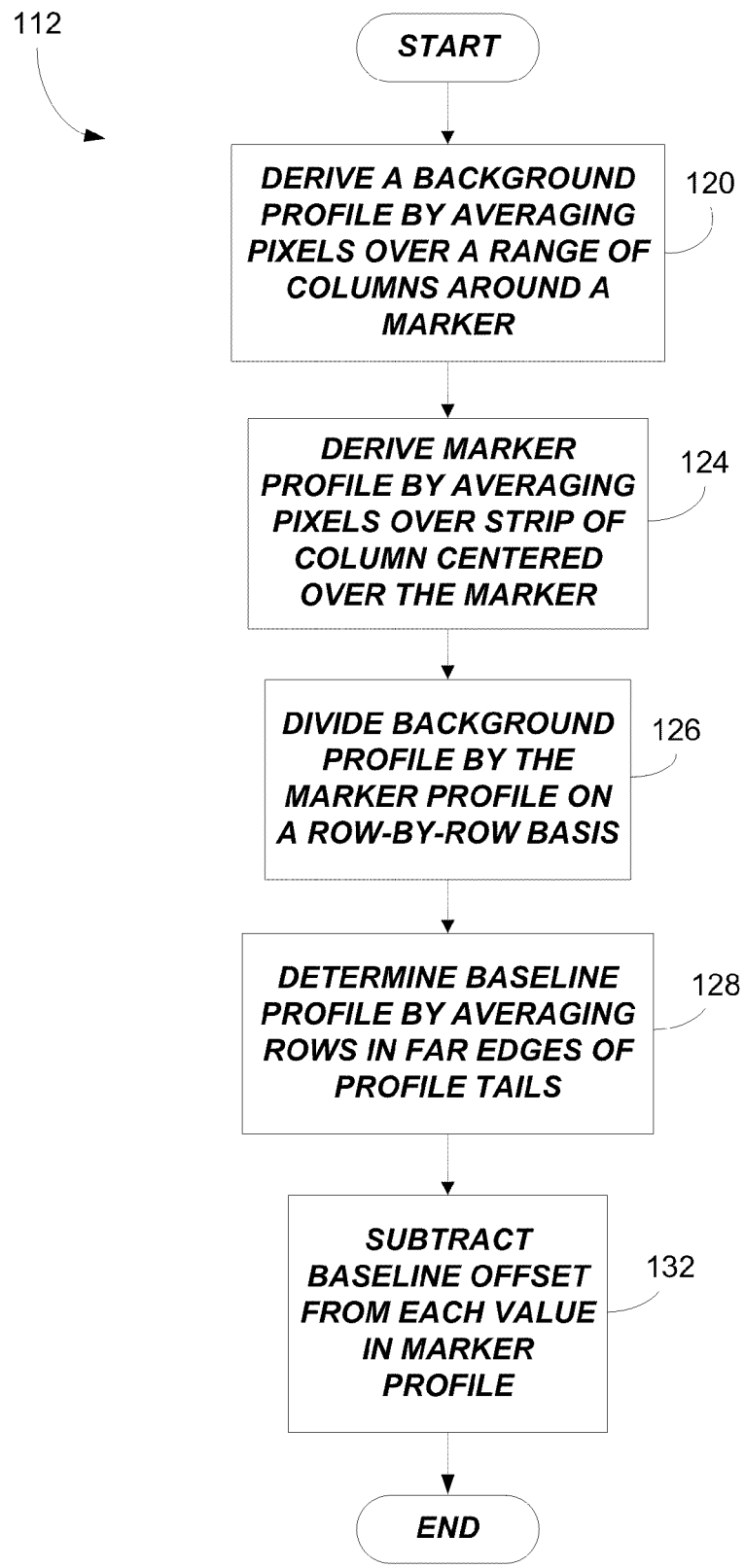
FIG. 12 is a flow chart illustrating a marker point profile derivation process of the marker point sub-pixel localization method of Fig.

FIG. 12 illustrates the marker point profile derivation process 112 according to one embodiment of the invention. Consider the operation of deriving the vertical position of the marker point where a sequence of pixels in the vertical direction is referred to as a column and a sequence of pixels in the horizontal direction is referred to as a row. The process for deriving the horizontal position of the marker point is analogous but with all references to rows replaced by columns and references to columns by rows. A row of pixels and column of pixels may each be referred to as a pixel line.

Figure 13:
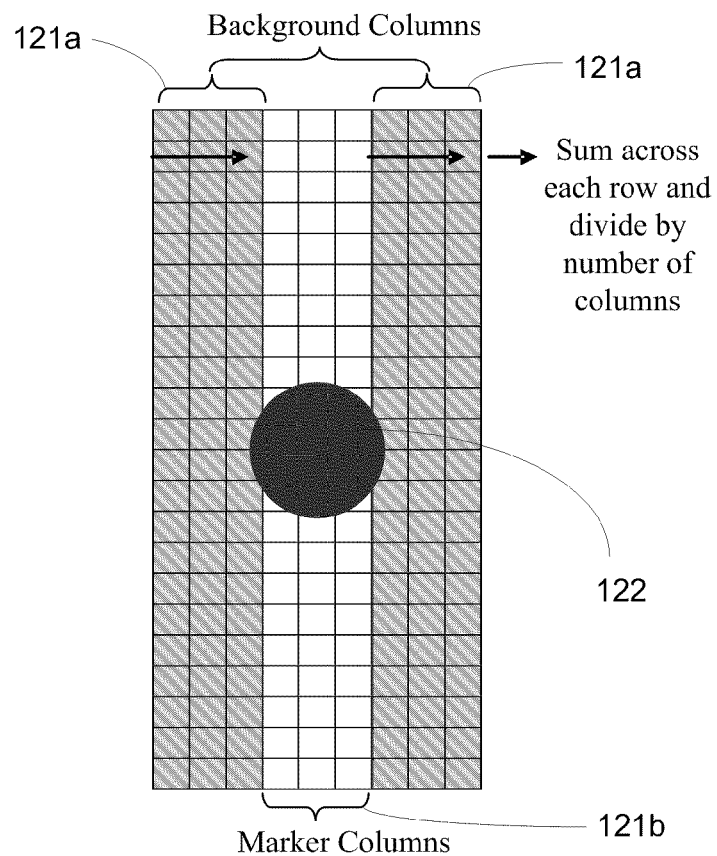
FIG. 13 is a graphical illustration of example pixel columns surrounding a marker point that are analyzed in the marker point profile derivation process of FIG. 12.

The first step of the process involves deriving a vertical background profile by averaging the pixel values over a range of background columns surrounding the marker (step 120). FIG. 13 illustrates example columns of pixels 121 surrounding and centered on a marker point 122. Step 120 averages the pixel values of background columns 121a surrounding the marker point 122 and excludes the pixel values of the marker columns 121b centered over the marker point 122. Averaging the background columns 121a includes summing the pixel values across each row of the columns 121a and dividing the sum by the number of columns. Averaging the background columns 121a generates a single column of background values, which is a background profile for the marker point 122.

Next, a marker point profile is derived by averaging the marker columns 121b, which are the columns centered over the marker point 122 (step 124). Again, averaging the marker columns 121b includes summing the pixel values across each row of the columns 121b and dividing the sum by the number of columns. Averaging the marker columns 121b generates a single column of marker values, which is a marker point profile for the marker point 122.

At step 126, the background profile is divided by the marker point profile on a row-by-row basis. For example, the value in each row of the column of averages making up the background profile is divided by the value in the corresponding row of the column of averages making up the marker point profile. Dividing the row values in this order ensures that image inversion occurs (e.g., dark areas become light and light areas become dark). In addition, step 126 uses division (e.g., instead of subtraction) to compensate for the negative exponential nature of x-ray attenuation (since, as noted, division is mathematically equivalent to taking the exponent of the difference of the logs of the two profiles).

As an alternative embodiment, the log of the pixel values can be computed before finding the marker point profile and background profile. Then background compensation of the marker point profile is accomplished by subtracting the two profiles on an element-by-element basis and taking the exponent of each element. This approach is slightly more precise than the above because it more accurately deals with images variations over the averaged rows, but it takes more time than the simple average and divide approach.

Figure 14:
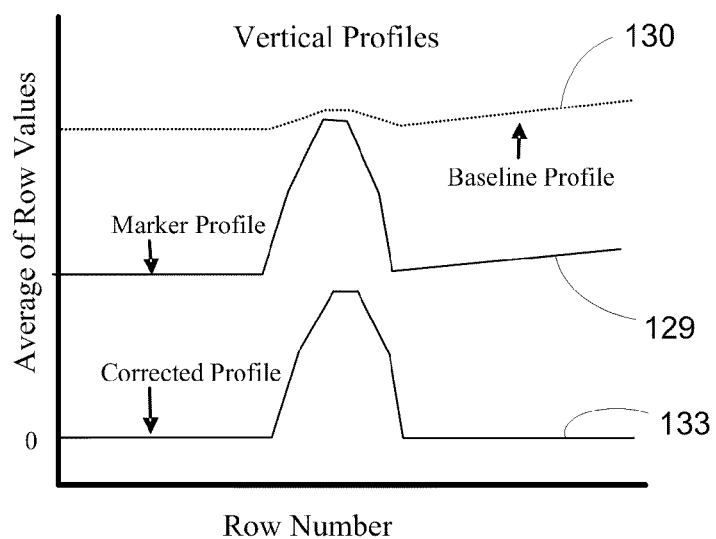
FIG. 14 is a graph illustrating example values of a marker point profile and a baseline profile used in the marker point profile derivation process of FIG. 12.

At this point, a reasonable baseline-corrected profile of the marker-point has been obtained. However, there may still be some residual offset of tails of the profile from zero, particularly if the tails are asymmetric. The profile is brought to zero by the following procedure. An average baseline offset value is determined by averaging pixel values over columns in the tail distant from a peak of the marker point (e.g., a pixel within the marker point having the highest value), such as over columns where the pixel values are no longer decreasing as they move away from the marker point center) (step 128). Care is taken to exclude from this average pixels in the tails associated with any structures adjacent to this marker point such as other markers or other structures in the image. FIG. 14 graphically illustrates the values of an example marker point profile 129 and an example baseline profile 130 and the results after fully baseline-correcting the marker point profile 133.

Figure 15:
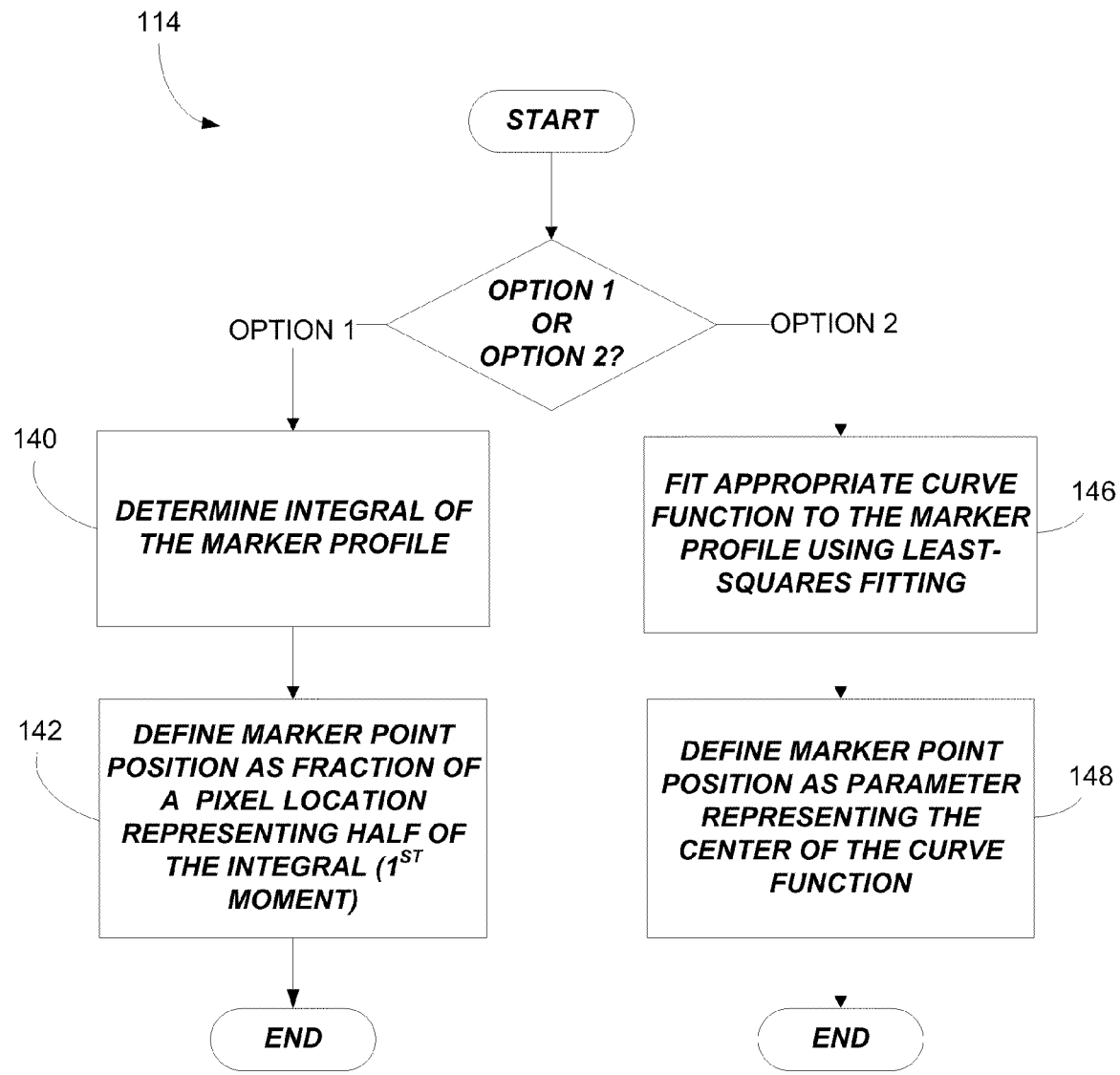
FIG. 15 is a flow chart illustrating a marker point position determination process of the marker point sub-pixel localization method of FIG. 11.
Figure 16:
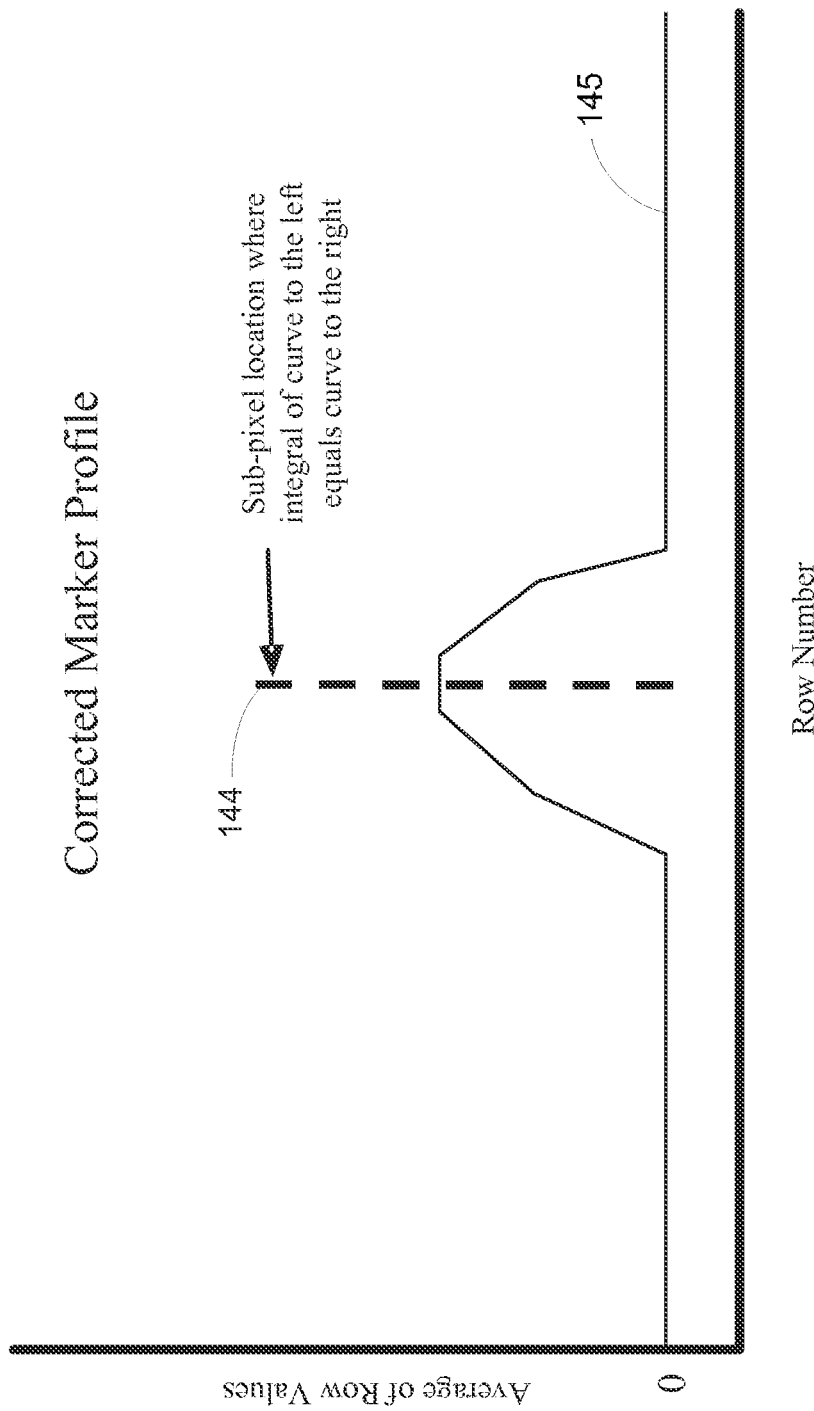
FIG. 16 is a graph illustrating a sub-pixel marker point center location of an example marker point profile curve using the integral marker center determination process of FIG. 15.

Returning to FIG. 11, after the baseline-corrected marker point profiles are generated, the second step of the localization method 110 includes the marker point position determination process 114. FIG. 15 illustrates this process in more detail. As shown in FIG. 15, there are at least two alternatives or options for performing this process. A first option includes determining the integral of the marker point profile (step 140) and defining the marker point position as the location along the integral representing half of the integral (step 142). This marker point position is effectively the first moment of the integral, or the position where that part of the integral to the left of this point equals that part of the integral to the right of this point. FIG. 16 illustrates an example sub-pixel marker point position location 144 of an example marker point profile curve 146.

Figure 17:
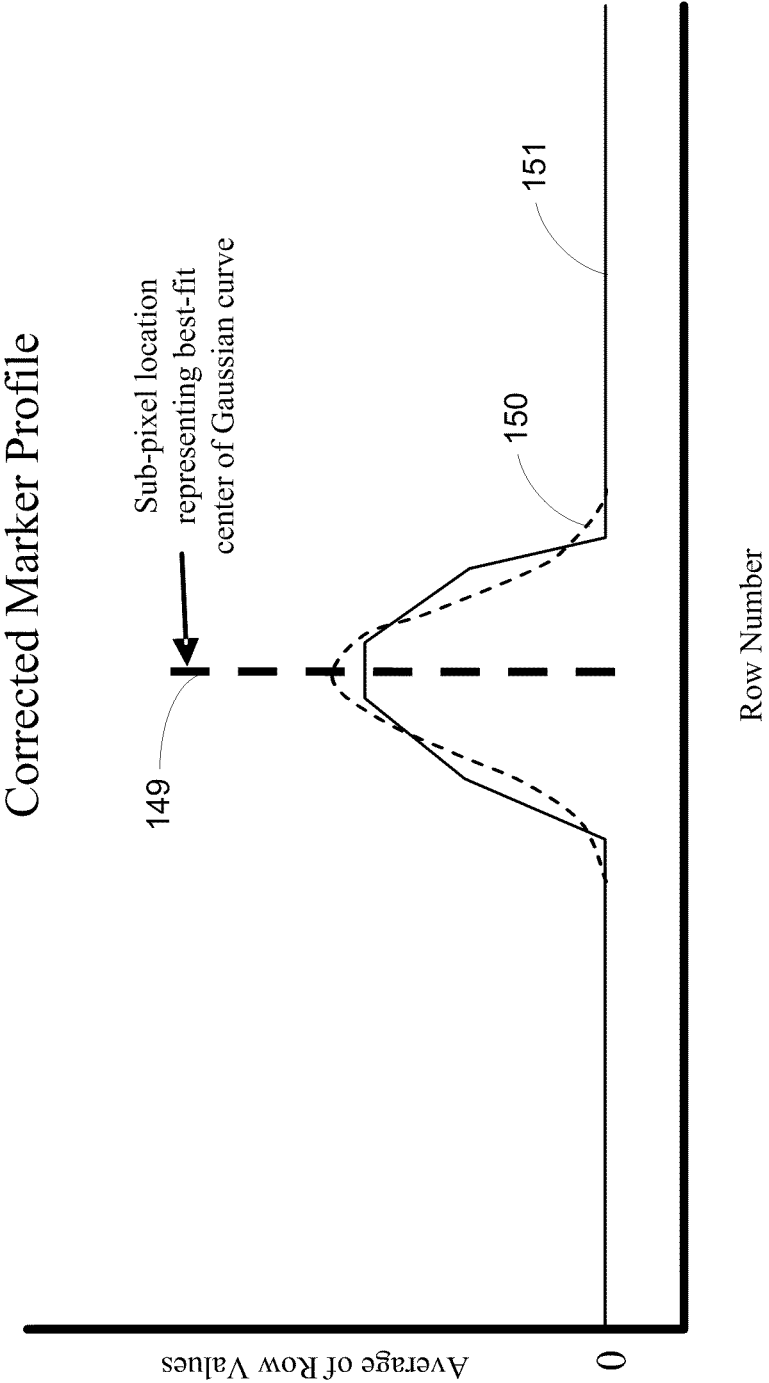
FIG. 17 is a graph illustrating a sub-pixel marker point center location of an example best-fit Gaussian curve to a marker point profile curve using the curve fit marker point center determination process of FIG. 15.

Returning to FIG. 15, the second option for determining a marker point position fits an appropriate curve function to marker point profile using least-squares or other fitting (step 146) and defines the marker point position as the parameter representing the center of the curve function (step 148). FIG. 17 illustrates an example sub-pixel marker point position location 149 of a best-fit Gaussian curve 150 fitted to an example marker point profile curve 151.

The curve function used in step 146 may be a Gaussian curve or an expected curve of a marker point, which takes into consideration issues related to imaging physics, such as partial volume effects and exponential attenuation characteristics. In general, the curve function used in step 146 may be any curve where one of the curve definition parameters represents a curve center. The curve function may also handle non-constant baseline profiles. In some embodiments, if a curve function is selected that handles non-constant baseline profiles, steps 128 and 132 in the marker point profile derivation step 112 can be eliminated. Furthermore, the curve function may be dynamically modified for each marker, image, or set of images based on measurable image characteristics, such as known marker dimensions, pixel size, and approximate sub-pixel location of a marker in other dimensions.

Determining 3D Cylindrical Coordinates for a Marker

Even after marker points and the marker point centers are identified in the images (e.g., using the marker point identification method 60 and the marker point sub-pixel localization method 110), the accumulation of marker points needs to be classified such that each marker point is properly associated with the physical marker responsible for generating the point. In order to do this, the first step is to uniquely identify each physical marker point. The physical marker points are each uniquely identified through their three-dimensional (3D) coordinates. Therefore, the first step in associating marker points with physical markers is to identify the physical markers and assign each its 3D coordinates. This process, however, can be complicated by patient movement and errors in the determination of marker point position on the projection images. In addition, because there are multiple markers, some marker points may be superimposed over other marker points in some projection images.

Figure 18:
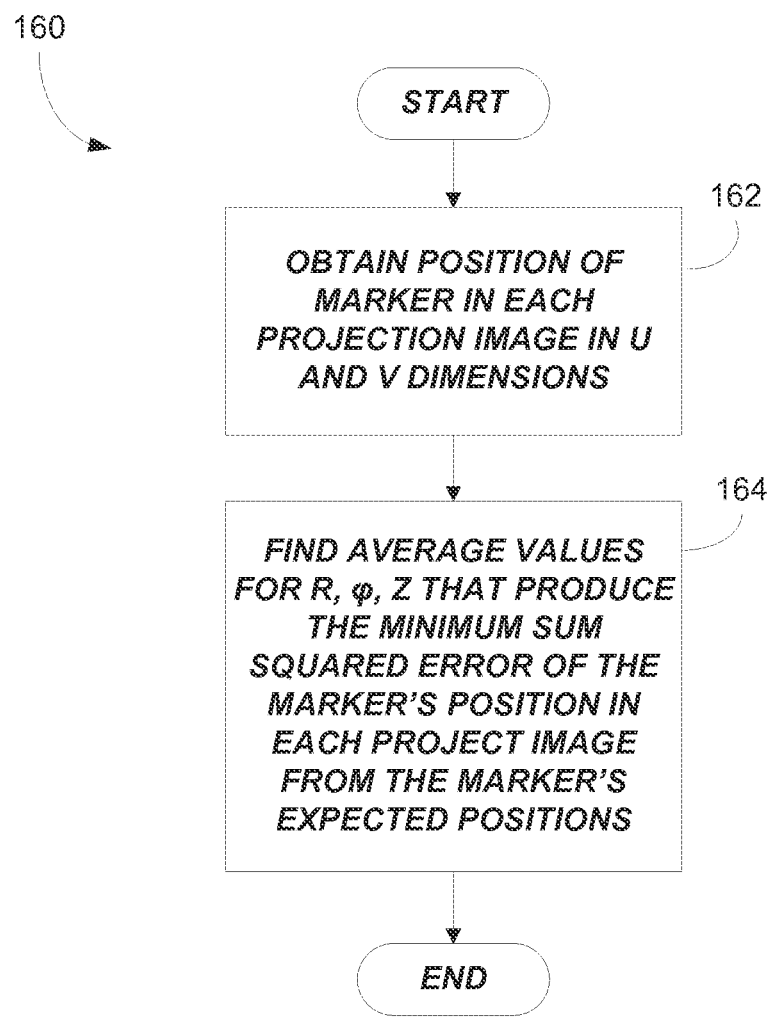
FIG. 18 is a flow chart illustrating a physical marker three-dimensional localization method.

FIG. 18 illustrates a physical marker 3D localization method 160 for identifying each of the physical markers and assigning each physical marker a position or location in 3D space. The physical marker 3D localization method 160 is performed by the EPU 42 of the computer 14 when the EPU 42 executes the physical marker 3D localization module 54. The physical marker 3D localization method 160 generally tracks the position of the points produced by the marker through a sequence of images generated as the CT gantry rotates to map the marker to a position in 3D space.

Existing tracking technologies use multiple sensors and multiple fixed relationships between multiple detected sites to track the position of a patient in 3D space. The tracking technology or method applied in the method 160, however, uses isolated single point detection sites. Therefore, rather than comparing the characteristics of multiple sites collected at the same time, the tracking method collects characteristics of single sites over time and matches the observed positional change over time to a 3D position that would produce the same positional change over time. This tracking method does not require any extra equipment other than the CT imaging gantry and is tolerant of a relatively large amount of image noise and patient movement.

As shown in FIG. 18, the method 160 starts by obtaining the position of each marker point (e.g., the center of each marker point determined by the marker sub-pixel localization method 110) on each projection image in two image dimensions, labeled "U" and "V" (step 162). U is a dimension tangential to the circle of rotation of the CT gantry and V is a dimension parallel to the axis of rotation of the CT gantry. These dimensional positions of a marker point may be determined by the marker identification point method 60, the marker point sub-pixel localization method 110, or combinations thereof.

If a marker has a fixed position in 3D space, its U and V positions (or values) on each projection image are described by the following formulas:

$$U = \frac{DSD * R * \sin(\theta - \phi)}{DSO - R * \cos(\theta - \phi)}$$

$$V = \frac{DSD * Z}{DSO - R * \cos(\theta - \phi)}$$

where the 3D cylindrical coordinates (R=radial distance, φ=angular position, and Z=height or axial position) represent the marker's 3D position, θ is the rotational angle of the CT gantry from its starting position, DSD is the distance from the x-ray source to the detector, and DSO is the distance from the x-ray source to the object or patient.

To determine a marker's 3D position, the marker's cylindrical coordinates or parameters (R, φ, and Z) must be determined using the above U and V formulas and the marker's known U and V values. However, the U and V positions in a particular projection image may be different from their correct values because of measurement error. Also, R, φ, and Z are functions of time (e.g., R(t), φ(t), and Z(t)) due to patient motion.

Due to these difficulties, the method 160 finds "average" values for R, φ, and Z (step 164). The average values are those values that produce the minimum sum squared error of the marker's actual position in each projection image from the marker's expected position in each projection image as specified by the above U and V formulas. The following error formula generally provides these average values:

$$Err = \sum_{\theta=1}^{n} \left( \left[ U_{meas} - \frac{DSD * R_{avg} * \sin(\theta - \phi_{avg})}{DSO - R_{avg} * \cos(\theta - \phi_{avg})} \right]^2 + \left[ V_{meas} - \frac{DSD * Z_{avg}}{DSO - R_{avg} * \cos(\theta - \phi_{avg})} \right]^2 \right)$$

However, the process of finding the desired values for $R_{avg}$, $Z_{avg}$, and $\phi_{avg}$ is simplified because the U dimension is independent of Z. As such, the process can be divided into two processes or steps: (1) analyzing the marker's behavior in the U dimension (see method 166 in FIGS. 19A-B) and (2) analyzing the marker's behavior in the V dimension (see method 168 in FIGS. 19C-D).

Figure 19A:
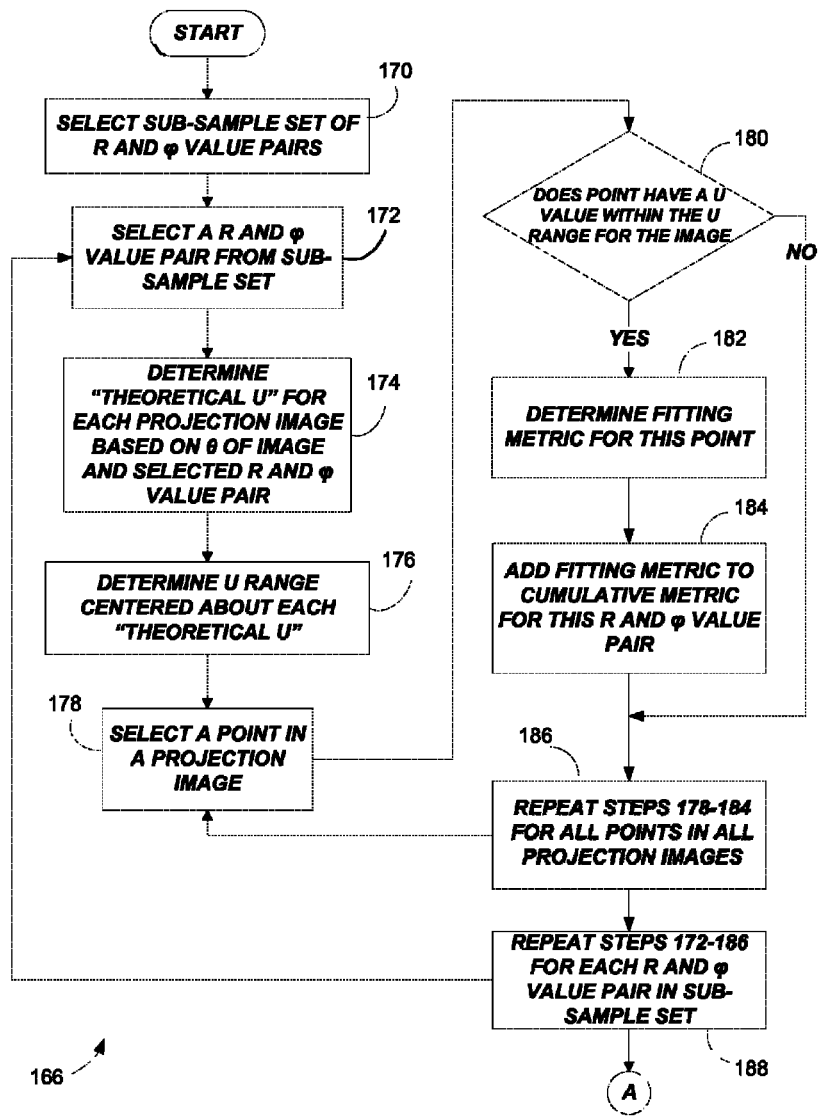
FIGS. 19A-B is a flow chart illustrating a process of analyzing a marker point's behavior in a U dimension.
Figure 19B:
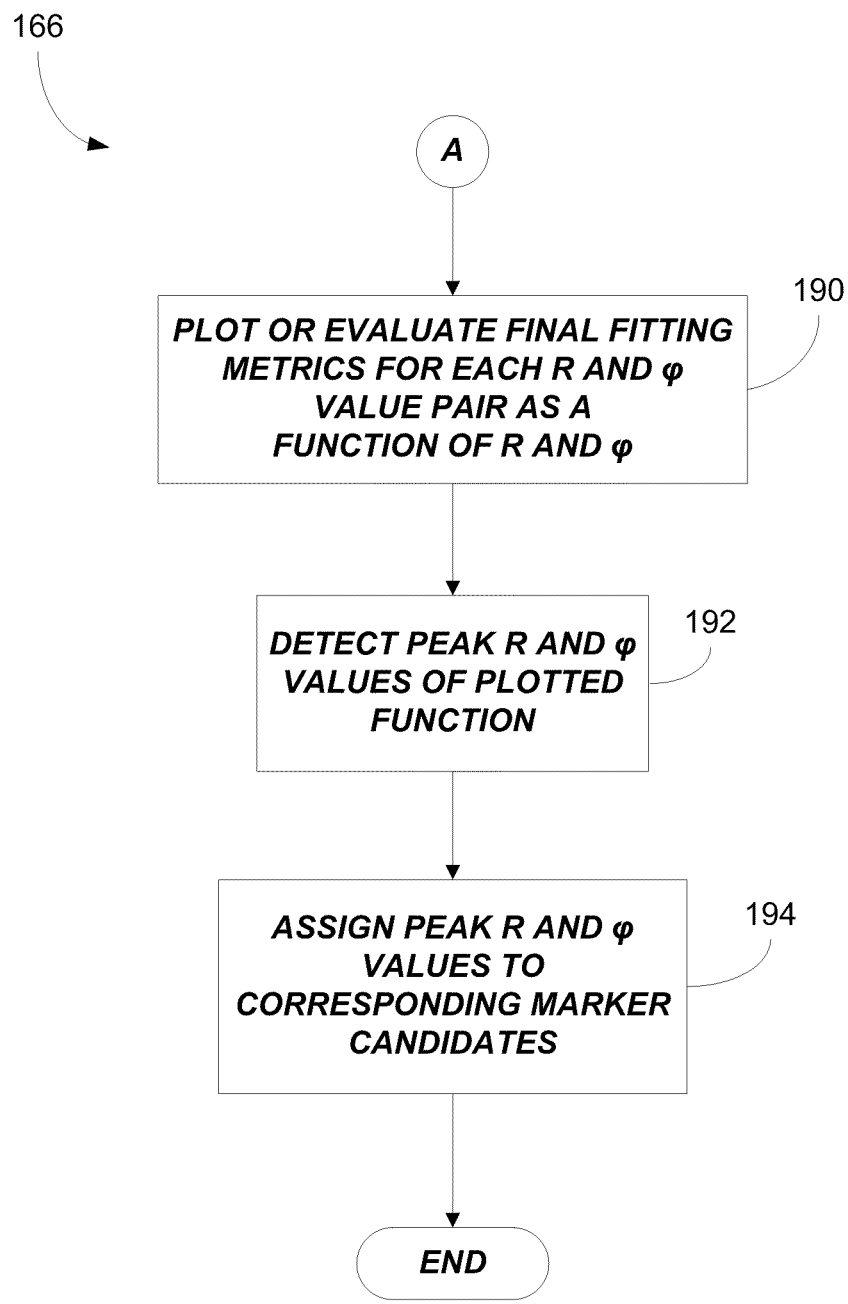

FIGS. 19A-B illustrates a method 166 of analyzing the marker's behavior in the U dimension according to one embodiment of the invention. As shown in FIG. 19A, the method 166 starts by selecting a number set of R and φ value pairs representing a sub-sample of all possible value pairs for the R and φ parameters (step 170). The size of the sub-sample set represents a compromise between execution speed and obtainable accuracy for R and φ. In general, the R and φ values are chosen to uniformly sample the range of physically possible R and φ values. That is, R is between 0 and the maximum scanner radial field of view, and φ is between 0° and 360°. Alternatively, a value of R may be assumed and only a sub-sample of possible values of φ is selected. Therefore, although the remaining steps of the method 166 are described with reference to pairs of R and φ values, it should be understood that the steps can be performed with an assumed value of R and varied values of φ.

As shown in FIG. 19A, after the sub-sample set is selected, an R and φ value pair is selected from the sub-sample set to process (step 172). Next, using the selected R and φ value pair and the U formula described above, a "theoretical U" value is determined for each projection image (step 174). Because each projection image is associated with a particular angle of rotation of the CT gantry, the θ value associated with each projection image is used in the U formula to determine each "theoretical U." A U range is then defined around each "theoretical U" value (step 176). The U range is centered about the "theoretical U" value and has a magnitude in each direction from the center equal to the maximum expected U-variation of a marker from its average or expected U position caused by patient motion.

Next, the U positions of the marker points identified in each projection image are compared with the U range for each projection image. In step 178, an identified marker point is selected. If the selected marker point identified in a projection image has a U value that falls within the projection image's U range (as determined in step 180), the marker point is identified as a marker point candidate and the method proceeds to step 182. Marker points that fall outside this range are neglected. It should be understood that more than one marker point may have a U value within a U range for a particular projection image. In fact, if there are multiple adjacent physical markers positioned on a patient, it is likely that more than one marker identified in the projection images will have a U value within a U range for a particular projection image (i.e., a particular value of θ).

Figure 20:
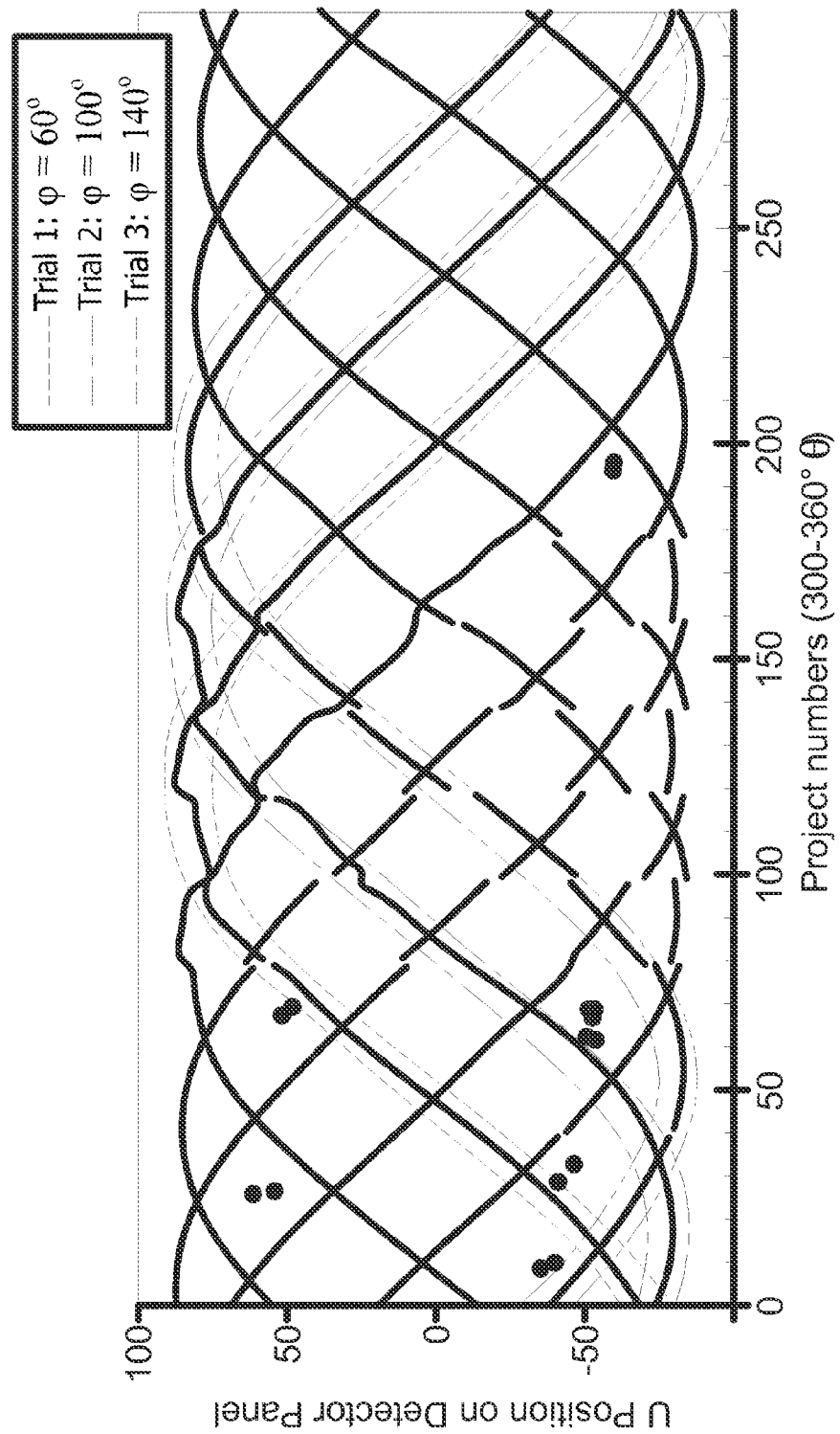
FIG. 20 is a graph illustrating an example of the process of fitting a trial value of ϕ to multiple U positions of a number of marker points through a sequence of projection images in the presence of motion in the U direction.

FIG. 20 illustrates the U positions of a number of markers through a sequence of 300 projection images. As shown in FIG. 20, three trials or variations of φ values were performed, while a corresponding R value was assumed and held constant. In particular, a first trial used a φ value of 60 degrees, a second trial used a φ value of 100 degrees, and a third trial used a φ value of 140 degrees. The U ranges for each of these trials are shown in the graph with dashed lines. For each projection image (see x-axis), each marker point that has a U position within the U ranges will be marked as a candidate marker.

Next, a fitting metric is determined for each candidate marker point in each projection image (step 182). In some embodiments, the fitting metric is the square of the distance between the marker candidate's U value and the closer boundary of the U range. For example, if a marker has a U value of 20 and the U range is 0 to 30, the fitting metric would be set to 10 (which is the distance between 20 and 30 —the closer U range boundary) squared or 100. If the marker's U value is the same as the "theoretical U" value, the fitting metric is maximized. The fitting metrics values from all candidate points are then summed to create a cumulative fitting metric, which is assigned to the currently selected R and φ value pair (step 184). As shown in step 186 of FIG. 19A, steps 178-184 are repeated for all points in all projection images.

Figure 21:
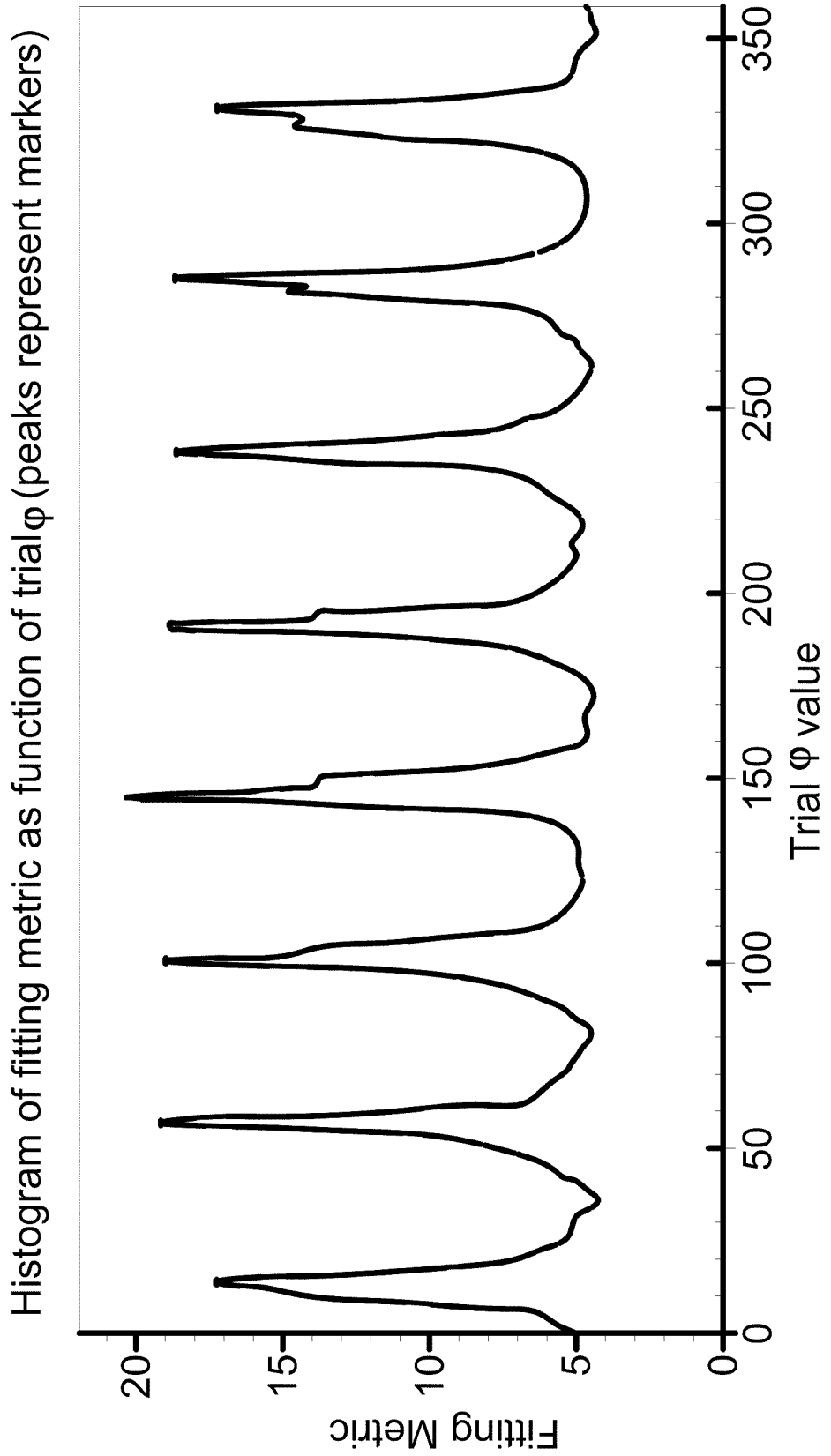
FIG. 21 is a graph illustrating an example one-dimensional plot of the cumulative fitting metrics for trial R and ϕ value pairs as a function ϕ at a fixed value of R.

As shown in FIG. 19A, steps 172-186 are repeated for each R and φ value pair in the sub-sample set (step 188) to assign a cumulative fitting metric to each value pair. After all of the R and φ value pairs have been assigned cumulative fitting metrics, the method 166 evaluates the cumulative fitting metrics for all R and φ value pairs as a function of R and φ (step 190 in FIG. 19B). The method 166 uses peak detection to determine the peaks of R and φ in this function (step 192). The peaks of the function are the peak R and φ value pairs which each represent one or more physical markers. The method 166 assigns each peak R and φ value pair to the corresponding marker associated with that peak (step 194). FIG. 21 illustrates an example of a one-dimensional plot (e.g., a histogram) of the cumulative fitting metrics for the R and φ value pairs as a function of φ (the value of R is assumed and held constant). As shown in FIG. 21, the peaks of the plotted function represent φ values for the physical markers.

Figure 19C:
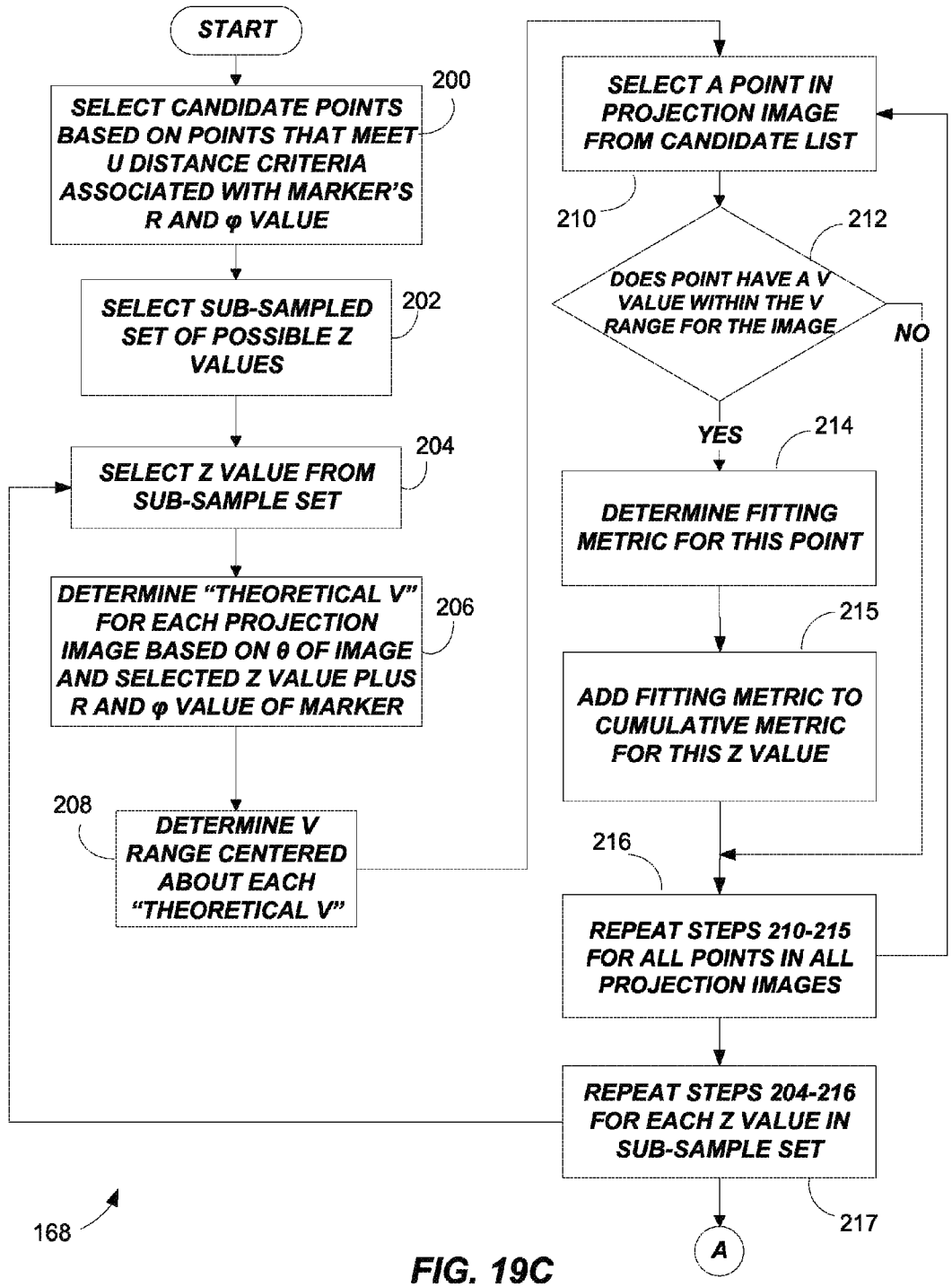
FIGS. 19C-D is a flow chart illustrating a process of analyzing a marker point's behavior in a V dimension.
Figure 19D:
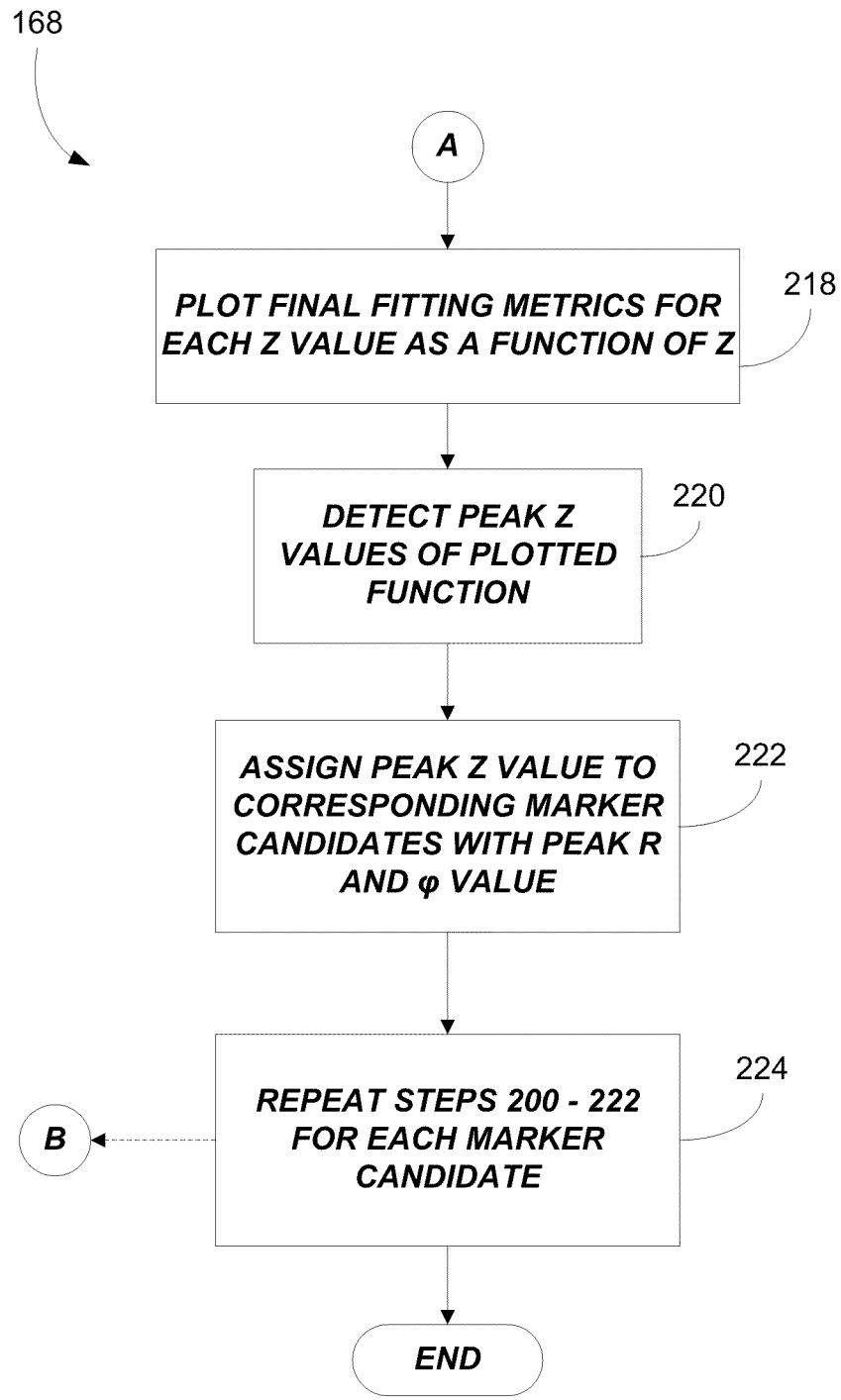

After analyzing the marker points' behavior in the U dimension, although candidate markers have been located and assigned R and φ values, it is possible that more than one marker exists with the same R and φ values. To address this situation, the marker points' behavior in the V dimension is analyzed. FIGS. 19C-D illustrates a method 168 of analyzing the marker points' behavior in the V dimension according to one embodiment of the invention. As shown in FIG. 19C, the method 168 starts by utilizing the peak R and φ value pair assigned to that marker candidate during method 166 (see step 194 in FIG. 19B). It uses these values to identify candidate points to evaluate further in terms of Z (step 200). A sub-sample of all possible values of Z is then selected. (step 202). The number of values in the sub-sample is chosen as a trade-off between execution speed and desired Z-value resolution. The range of the sub-sample is chosen to cover the range of physically possible values of Z (points that can at some point be within the scanning field of view).

A Z value is then selected from the sub-sample set (step 204). Using the R and φ value pair previously determined for this marker or markers, the selected Z value, and the V formula described above, a "theoretical V" value is determined for each projection image (step 206). Because each projection image is associated with a particular angle of rotation of the CT gantry, the θ value associated with each projection image is used in the V formula to determine each theoretical V. A V range is then defined around each theoretical V value (step 208). The V range is centered about the theoretical V value and has a magnitude in each direction from the center equal to the maximum expected V-variation of a marker from its average or expected V position caused by patient motion.

Next, the V position of each marker point that is part of the candidate list has its V value compared against the V range for this Z trial. In step 210, a point in the projection image is selected. If the point has a V value that falls within the projection image's V range (step 212), the marker is identified as a further restricted marker point candidate. To clarify, a point must fall within the range of U values associated with its R and φ values and within the range of V values associated with its R, φ, and Z values in order to be considered a candidate. As described above, more than one marker point identified in a particular projection image may have V and U values within the current V and U ranges associated with that projection image. As shown in step 216 of FIG. 19C, steps 210-215 are repeated for all points in all projection images.

Figure 22:
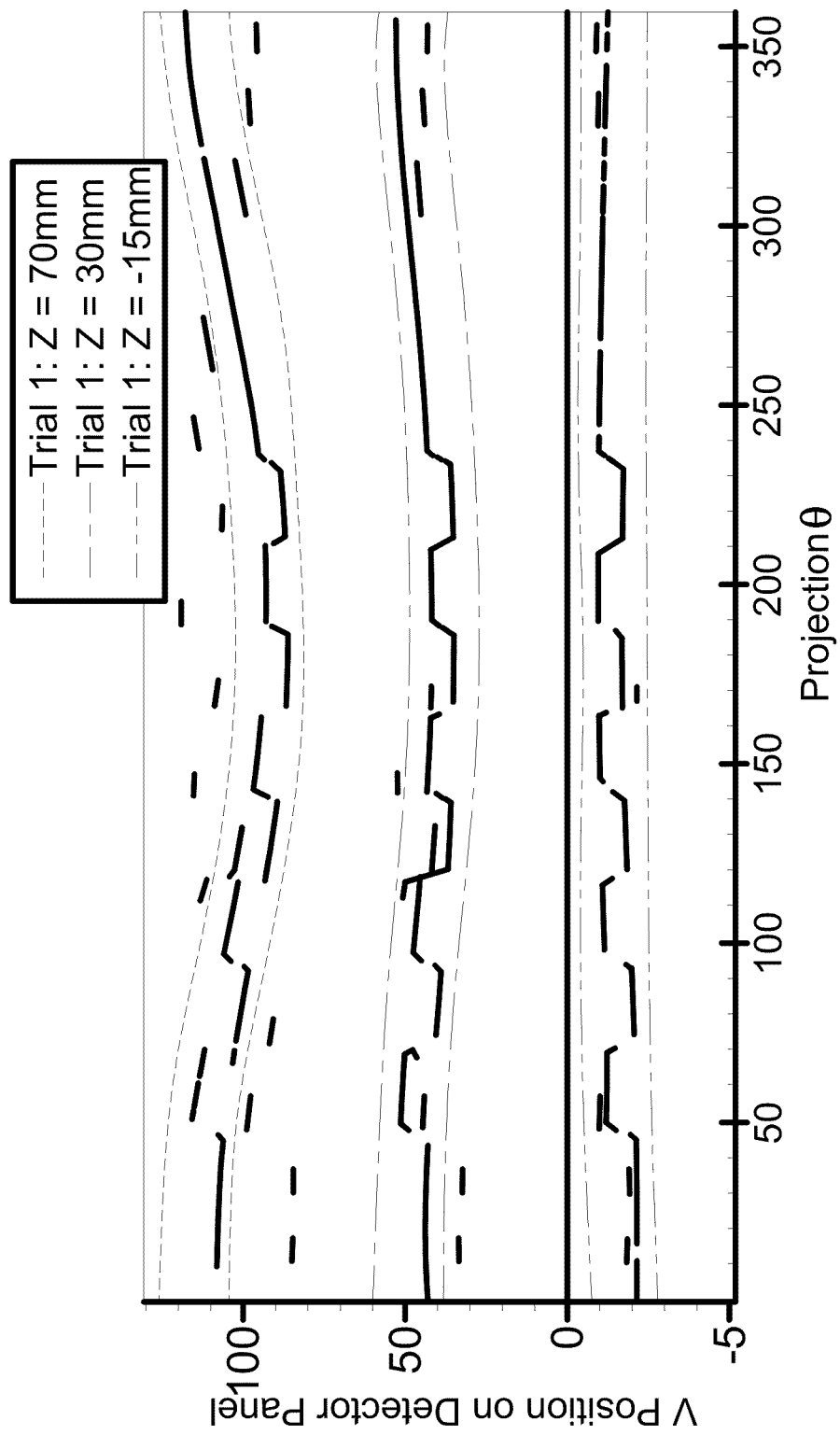
FIG. 22 is a graph illustrating an example of the process of fitting trial values of Z to the V trajectories of three markers through a sequence of projection images.

FIG. 22 illustrates the V positions of three markers through a sequence of 300 projection images. In FIG. 22, three trials or variations of Z values are shown. In particular, a first trial used a Z value of 70 millimeters, a second trial used a Z value of 30 millimeters, and a third trial used a Z value of −15 millimeters. The V ranges for each of these trials are shown in the graph with dashed lines. For each projection image (see x-axis), each marker that has a V position within the V ranges will be marked as a marker candidate.

Returning to FIG. 19C, a fitting metric is determined for each marker candidate in each projection image (step 214). The fitting metric is the square of the distance between the marker candidate's V value and the closer boundary of the V range. For example, if a marker has a V value of 20 and the V range is 0 to 30, the fitting metric would be set to 100 (which is 10—the distance between 20 and 30, the closer V range boundary—squared). The metric fittings from all the projection images are then summed to create a cumulative fitting metric, which is assigned to the currently selected Z value (step 215).

As shown in FIG. 19C, steps 204-218 are repeated for each Z in the sub-sample set (step 217) to assign a cumulative fitting metric to each value. After all of the Z values in the sub-sample set have been assigned cumulative fitting metrics, the method 168 evaluates the relationship between Z and the resulting cumulative fitting metric (step 218 on FIG. 19D). The method 168 then uses peak detection to determine the peaks of the relationship (step 220).

Figure 23:
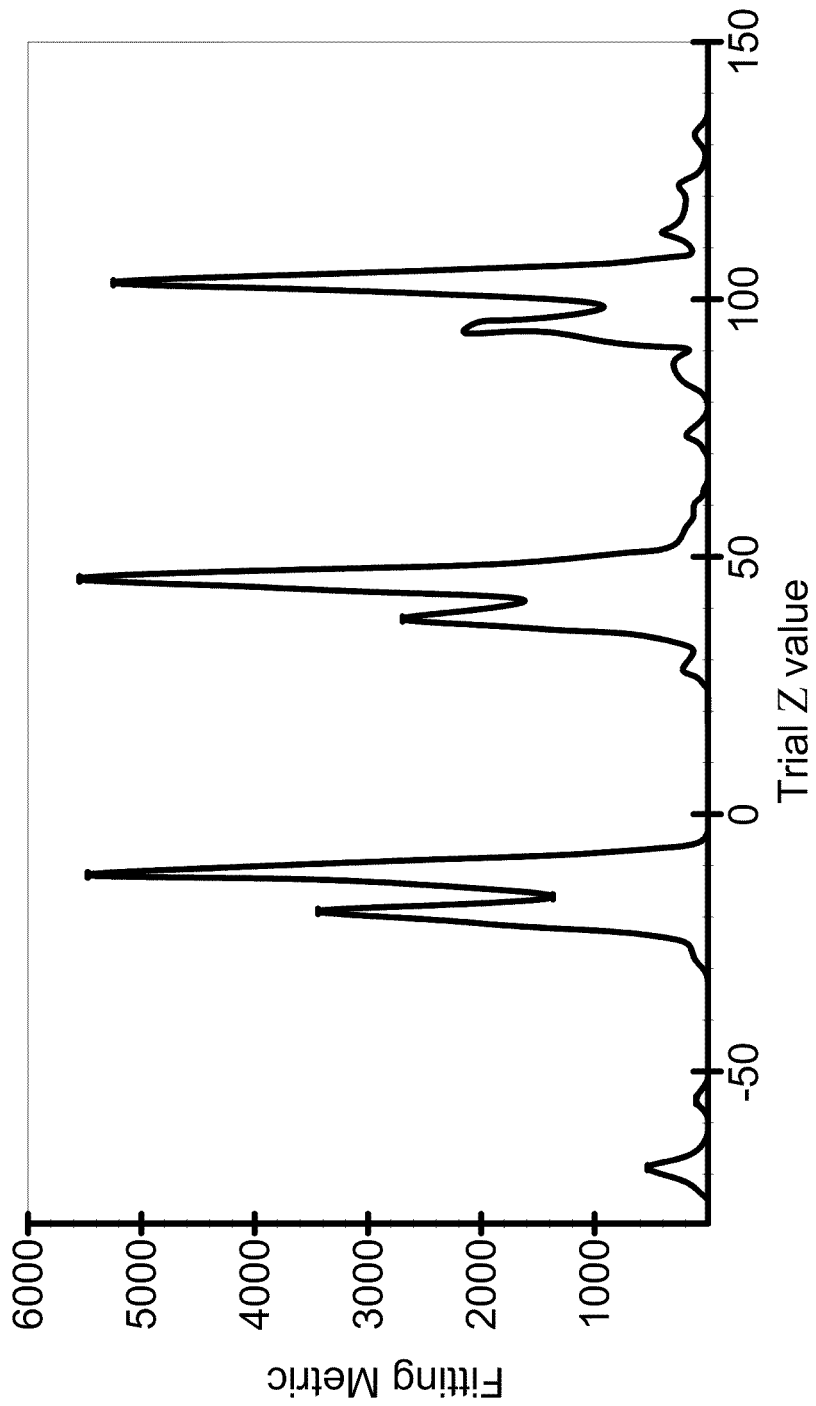
FIG. 23 is a graph illustrating an example one-dimensional plot of the cumulative fitting metric as a function Z.

Each peak in the cumulative fitting metric—Z relationship is associated with a unique physical marker. The Z value of the peak represents the Z value of the corresponding physical marker. The R and φ values assigned are those previously found for the marker or markers. Each of these markers now has known values for all three cylindrical coordinates (R, φ, Z). FIG. 23 illustrates an example of a one-dimensional plot (e.g., a histogram) of the cumulative fitting metric as a function of Z. In FIG. 23, there are three peaks corresponding to three separate physical markers, each at the same value of R and φ.

The method 168 is (steps 200-222) is repeated (step 224) for each of the other R and φ pairs determined by method 166 to isolate all unique physical markers and determine Z values for each. The method 168 terminates when all marker candidates are separated into unique physical markers and each physical marker has been assigned all three cylindrical coordinates. The assigned cylindrical coordinates represent the marker's average R, φ, and Z values, which represent the marker's 3D position.

The methods 166 and 168 described above with respect to FIGS. 19A-D represent a two-step process which uses two separate methods to assign 3D cylindrical coordinates to a marker (i.e., a first method assigns the R and φ values and a second method assigns the Z value). A first alternative implementation of the marker 3D localization method 160 combines these methods into a single operation where a sub-sampled set of values of R, φ, and Z is selected and each combination of values is used to determine a single fitting metric based on the combined U and V error. The result of this single process is a three-dimensional array that has peak values coincident with each isolated physical marker. This implementation, however, may take more time than the separate method implementation. In particular, if R, φ, and Z have, respectively, m, n, and q sub-samples, the first alternative implementation requires m*n*q iterations versus (m*n)+q for the separated implementation.

A second alternative implementation of the marker 3D localization method 160 can also be used to speed up the separated implementation. In the second alternative implementation, R, φ, and Z are found as a two-step process as originally described, but the number of R values (m) processed in the first method 166 would be decreased by sub-sampling R at a coarser frequency. This is reasonable because the fitting is less sensitive to R values. Then, a third method can be added that holds φ and Z fixed and uses a finer-sampled, sub-sample set of R and the fitting metric process described above to optimize R.

A third alternative implementation of the marker 3D localization method 160 can also make the sub-sampling coarser for one parameter, two parameters, or all three parameters. This implementation can also include final fitting methods for each marker candidate that uses a finer sampling rate for each parameter sub-sample set covering a narrower range. This implementation may increase both the speed of the method 160 and improve the final accuracy of the marker position coordinates.

One general challenge for the marker 3D localization method 160 is handling a situation where the markers are positioned very close to each other but still allow a reasonable range of motion for each marker. If the markers are separated by less than the maximum expected motion, the method 160 might label two markers as if they were one marker and assign this one marker a position between the actual positions of the two markers. To prevent this situation, the markers should be placed on the patient with adequate physical separation. But the method 160 needs to deal with situations where placement guidelines are not followed. The method 160 can be modified to identify situations where a large percentage of projection images have more than one marker within the candidate point acceptance range or identify situations where a cumulative metric peak is larger than expected for a single marker. If either of these situations is detected, the method 160 can include additional processing to better isolate the two markers. One approach would be, when overlapping markers are suspected, to repeat the localization process with a finer sub-sampling and ranges narrowed to cover only the suspect marker.

A second challenge is when marker motion causes two peaks in the cumulative fitting metric. In this case, a single marker will appear as two. To address this possibility, the method 160 can divide the θ range into sub-ranges, perform fitting within each sub-range separately, and then merge the results. In addition, the method 160 could adaptively change the candidate point acceptance range for the three coordinate parameters, R, φ, and Z. For example, the method 160 could start with a small acceptance range to ensure adequate isolation of closely adjacent markers and assuming little motion. If an adequate number of points are not included in these ranges, presumably because of motion, the range could be increased until sufficient candidate marker points are found.

In general, the marker 3D localization method 160 localizes markers to coordinate resolutions better than one millimeter in the presence of patient motion as great as two centimeters over the course of the scan. The method 160 also operates effectively in the presence of 24 or more markers and is tolerant of measurement noise. Finally, the method 160 can process 24 markers over 300 projection images in less than approximately 5 seconds.

Mapping a Point to a Physical Marker on a Patient

Even after image marker points are identified and localized and the corresponding physical markers identified and assigned 3-D coordinates, each marker point must be assigned to a specific physical marker placed on the patient. In a typical CB CT scan with 600 images and nine markers, there will be over 5,000 identified points in the projection images that must each be assigned to one of the nine physical markers.

Looking at the marker points identified in a single projection image, there is not (at least not in general) enough information to assign a particular marker point identified in an image to a particular physical marker positioned on the patient. In the ideal case, if the markers are physically motionless and their physical locations known exactly, unique U and V tracks of marker point position change from one projection image to a successive image can be defined for any marker point identified in the projection images. Only one physical marker will be consistent with the point position track that a particular marker makes from one projection image to the next. Thus, two projection images are theoretically sufficient to assign these two marker points to their corresponding physical marker.

However, additional challenges can occur when either a marker's physical location in the projection images is not exactly known or if there is a significant amount of patient motion (or unexpected gantry motion) during the scan. In these cases, a level of trajectory uncertainty is added that complicates the proper assignment of a marker point identified in projection images to a physical marker placed on a patient.

FIGS. 24A-E illustrates a physical marker mapping method 250 for assigning marker points identified in projection images to specific physical markers placed on a patient according to one embodiment of the invention. Generally, the method 250 tracks marker point locations in successive projection images in the presence of patient motion and evaluates each marker point on a projection image-by-projection image basis to identify the marker points most likely to be associated with a particular physical marker. The method 250 uses a number of different criteria, including the distances between the U and V measured for a marker point and the theoretical U and V associated with a physical marker and the time derivatives of these distances.

Figure 24A:
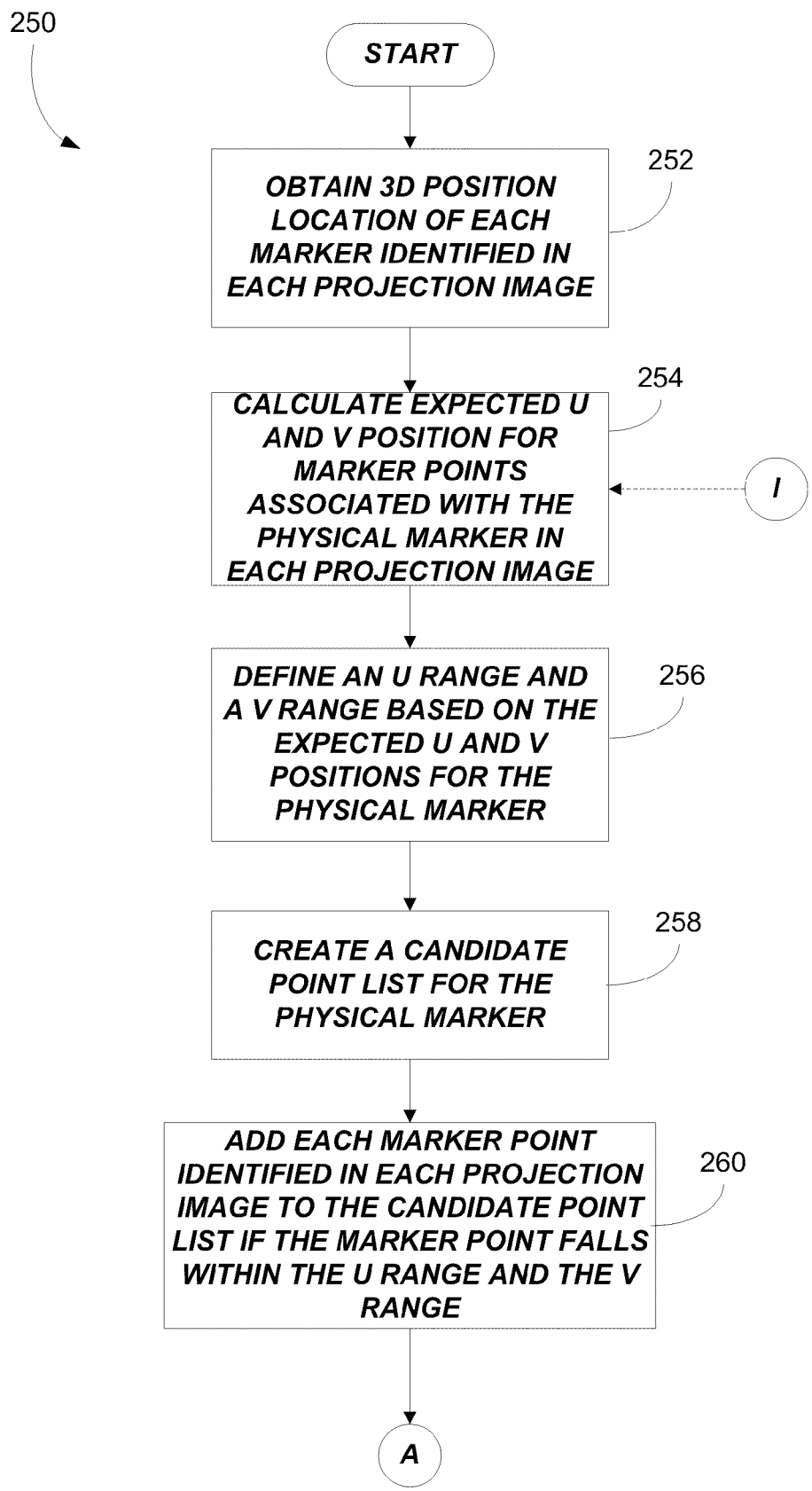
FIGS. 24A-E is a flow chart illustrating a marker point to physical marker mapping method.

As shown in FIG. 24A, an initial step of the method 250 includes identifying all physical markers associated with the scan and obtaining an approximate 3D location for each (step 252). This can be done using physical measurements, measurements from the reconstructed image dataset, or direct analysis of the projection images. In some embodiments, the method 250 uses the physical marker localization method 160 described above to obtain an approximate 3D location for each physical marker.

Next, the method 250 chooses one physical marker and calculates an expected U position ($U_{image}$) and an expected V position ($V_{image}$) for each projection image (step 254). The method 250 uses the following equations that describe how a physical point in space is expected to move from image to image based on the particular geometry of the CT gantry.

$$U_{image} = \frac{DSD * R * \sin(\theta - \varphi)}{DSO - R * \cos(\theta - \varphi)}$$

$$V_{image} = \frac{DSD * Z}{DSO - R * \cos(\theta - \varphi)}$$

For example, assuming that the CT gantry rotates smoothly about a center of rotation, R is the distance a point is from this center in a plane of rotation, $\phi$ is the angular location of the marker, and Z is the distance the marker is from the central plane of rotation (i.e., the plane that includes the point defining the location of the X-ray source). DSD is the distance from the x-ray source to the detector plane, and DSO is the distance from the x-ray source to the CT gantry's center of rotation. Each projection image is acquired at a gantry rotation angle of θ. Using these equations, the method 250 defines the expected U and V projection image positions of a physical marker with a 3D position of R, $\phi$, and Z at each projection image angle, θ.

The method 250 then uses the expected U and V marker image positions to define an expected U range and an expected V range of trajectories for the physical marker (step 256). The ranges are large enough to include all points associated with the physical marker, even in the presence of patient motion. For example, if the patient is expected to move as much as 20 millimeters over the course of the image acquisition, the expected U and V ranges for a particular physical marker would be:

$$\frac{DSD * R * \sin(\theta - \varphi)}{DSO - R * \cos(\theta - \varphi)} - 10 < U_{image} < \frac{DSD * R * \sin(\theta - \varphi)}{DSO - R * \cos(\theta - \varphi)} + 10$$

and $$\frac{DSD * Z}{DSO - R * \cos(\theta - \varphi)} - 10 < V_{image} < \frac{DSD * Z}{DSO - R * \cos(\theta - \varphi)} - 10$$

Figure 25:
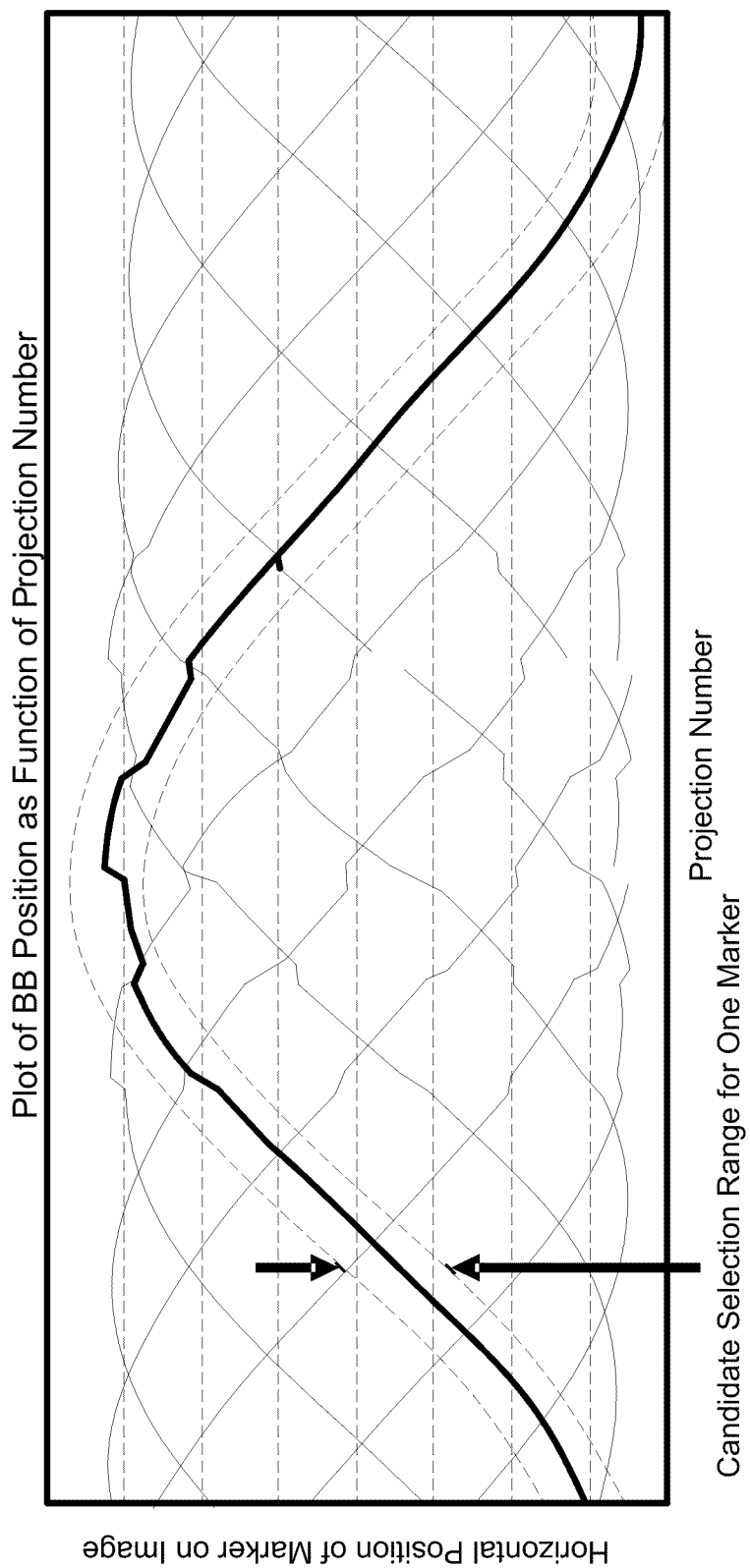
FIG. 25 is a graph illustrating an expected U range for an example physical marker and example U positions of all the marker points identified through the sequence of projection images.
Figure 26:
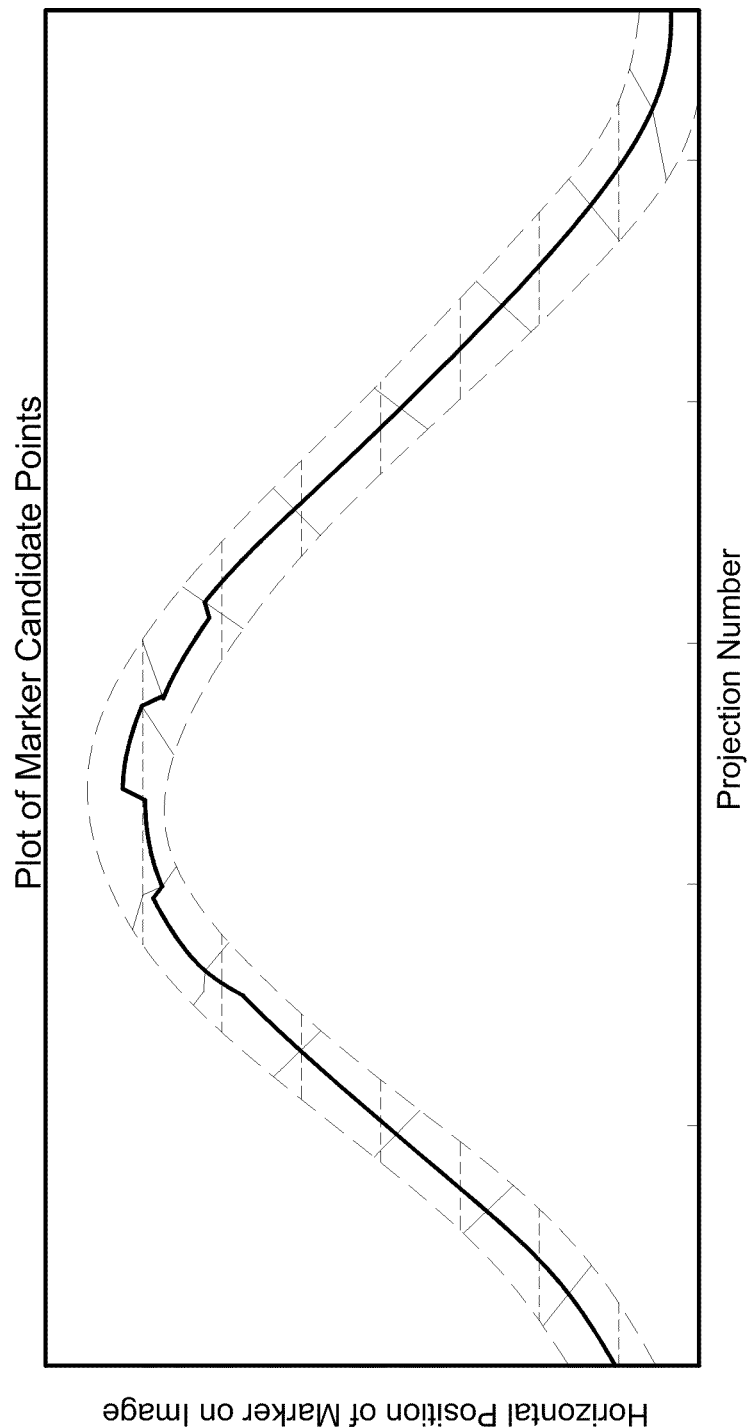
FIG. 26 is a graph illustrating the marker points illustrated in FIG. 25 that have U positions within the U range illustrated in FIG. 25.
Figure 27:
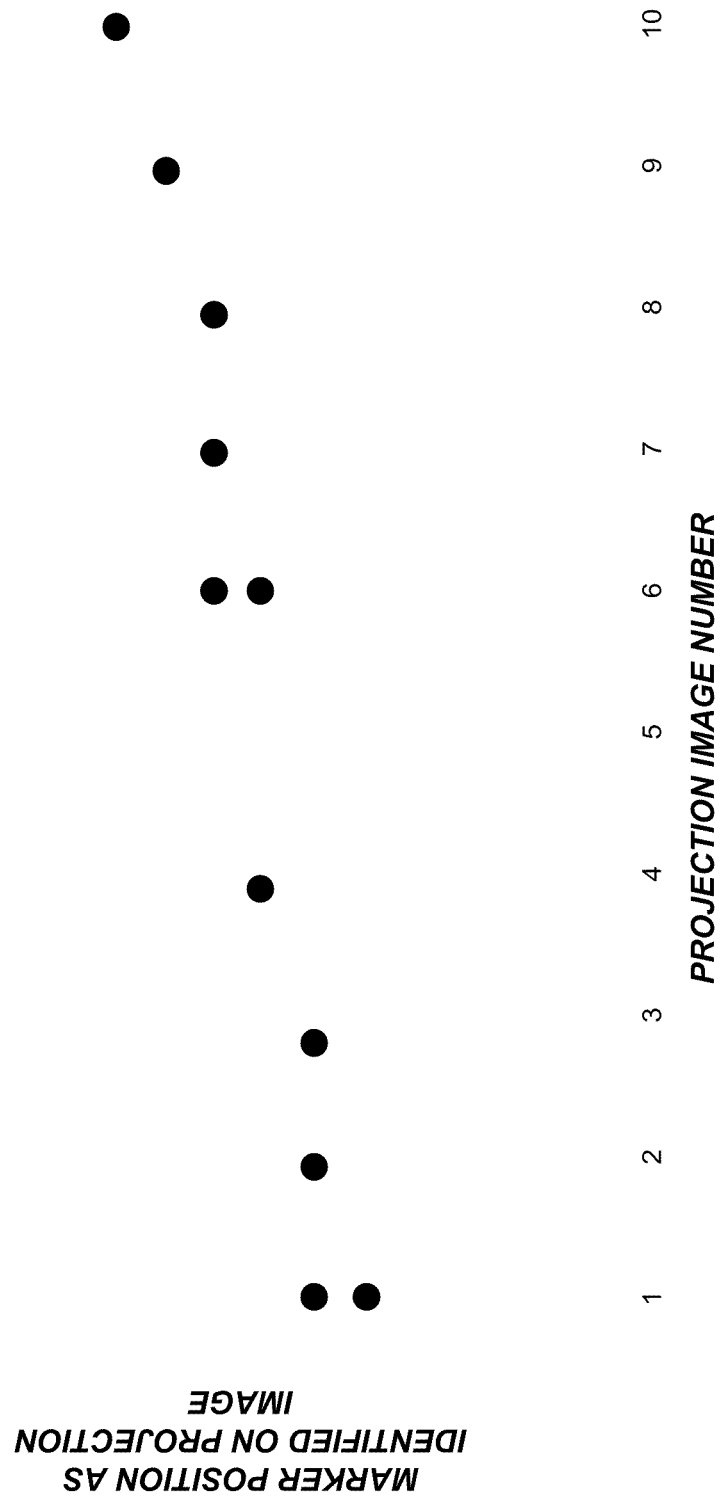
FIG. 27 is a graphical illustration of a portion of an example candidate marker point list.

The method 250 then creates a candidate point list for the physical marker (step 258) and adds each marker point identified in each projection image that falls within both the expected U range and the expected V range (step 260). FIG. 25 is a graph illustrating an example expected U range for a particular physical marker (between the dotted lines) and example U positions of marker points identified through a sequence of projection images. FIG. 26 illustrates those markers illustrated in FIG. 25 that have U positions within the expected U range illustrated in FIG. 25. Any of these markers that also have a V position within the expected V range will be added to the physical marker's candidate point list. For example, FIG. 27 graphically illustrates a portion of a candidate point list. As shown in FIG. 27, the candidate point list includes each marker from each projection image that has a U position and a V position that falls within the expected U and V ranges. The final list of marker points associated with the physical marker will be selected from this candidate point list. As shown in FIG. 27, the candidate point list can include more than one marker within a particular projection image (two candidate points in this example occur both in projection 1 and project 6. This can occur when two markers cross each other's path through the sequence of projection images. There can also be more than one marker point in a candidate point list for a particular projection image if two physical markers are positioned close to each other on the patient.

Figure 24B:
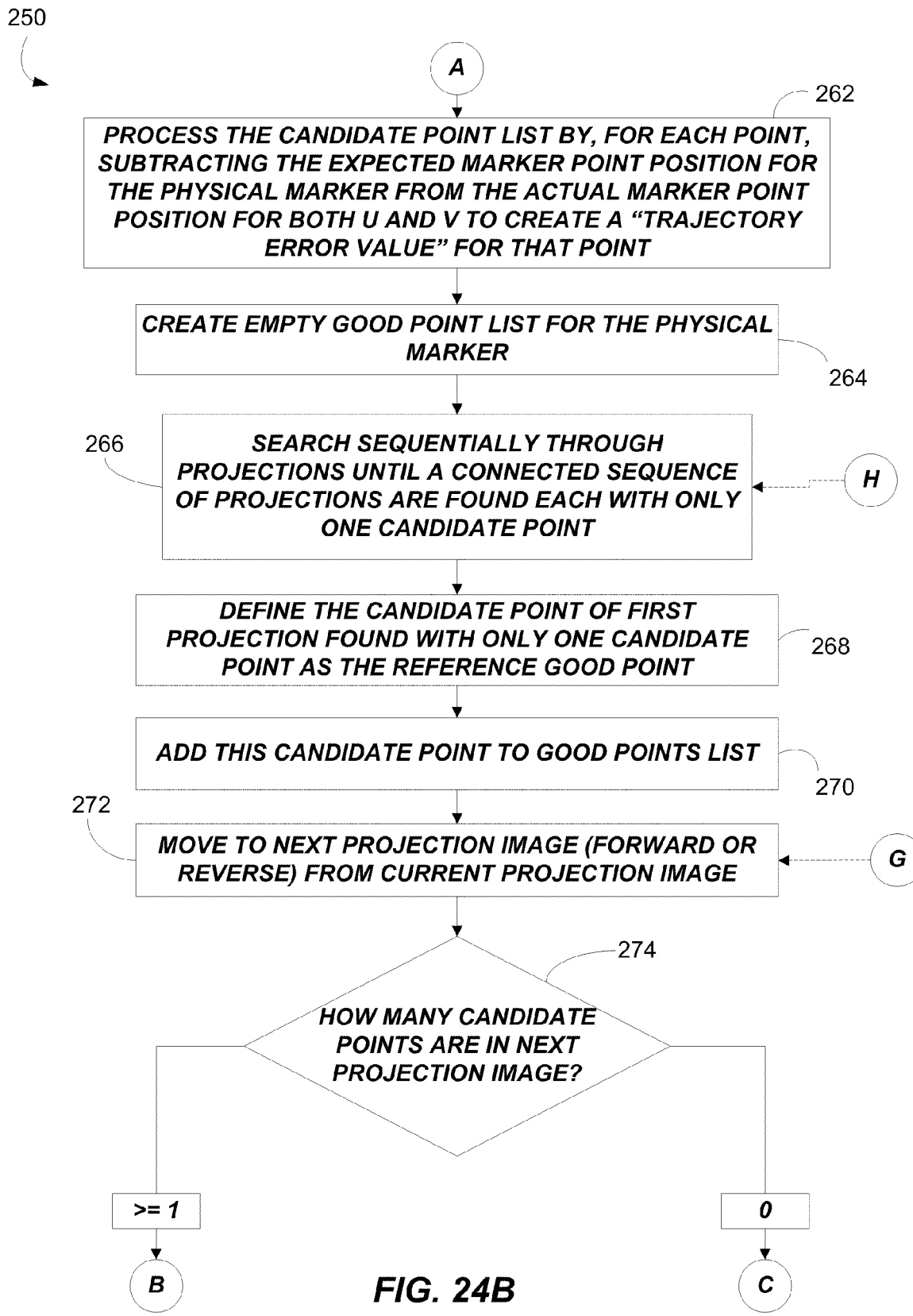
Figure 28:
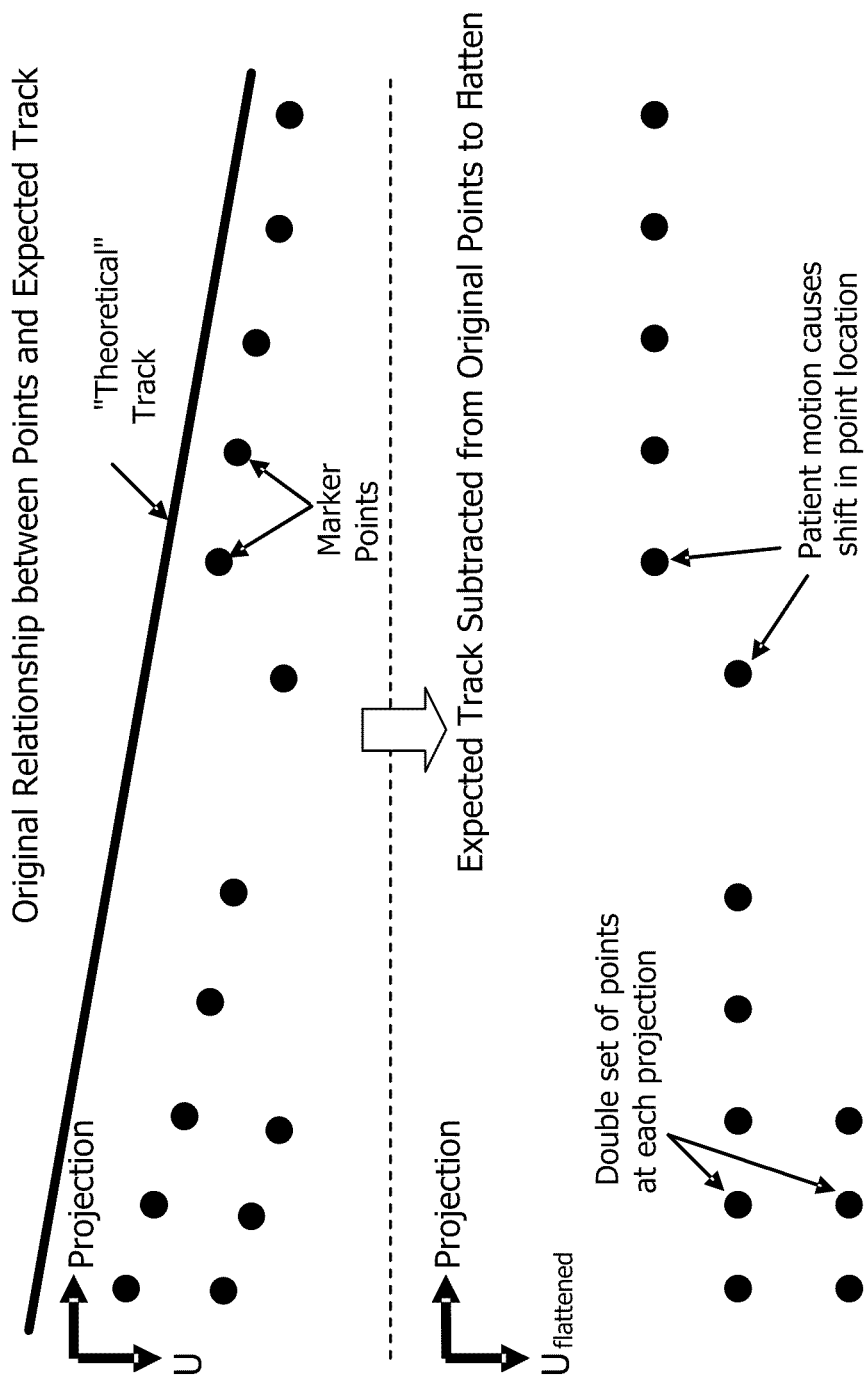
FIG. 28 is a graphical illustration of a flattening process of an example candidate marker point list.

As shown in FIGS. 24A and 24B, after creating and populating the candidate point list (steps 258 and 260), the method 250 processes the candidate point list by subtracting the "expected" marker locations of the physical marker from the actual marker point's locations for each point included in the candidate point list for both the U and V dimensions (step 262). This process flattens the marker's locations to create an "error from expected" candidate point list. The "error from expected" candidate point list, therefore, represents the amount of discrepancy or error (e.g., caused by patient movement or measurement error) between the expected position of the physical marker reflecting in the projection image and the actual marker point position. FIG. 28 graphically illustrates this flattening process applied to an example candidate point list.

Once the "error from expected" candidate point list is created for a physical marker, the process of point tracking occurs. The objective of this process is to proceed from one projection to the next and select the one point in the next projection most "likely" to be the correct point, that is, the point most likely to have been truly created by the associated physical marker. A number of heuristics are applied in order to accomplish this. The overall process generally has two components: synchronization and tracking. In the synchronization component, the point list is processed, one projection at a time, until a particular point is found to have a high likelihood of being associated with the physical marker. The tracking component starts with this point and continues, projection by projection, selecting the one (or zero) point (from the list of zero to multiple points at that projection) most consistent with a track that would be expected to be formed by this marker. If no consistent points are found for a set number of images, synchronization is lost and will have to be re-obtained. The tracking process can proceed in either direction of increasing projection number or decreasing projection number.

In the tracking process, at each new projection there are three possible cases: zero points exist, one point exists, and more than one point exists. Motion and measurement noise complicates the process in that a "correct point" might not be where it is expected to be. This is handled by implementing the concept of "suspect points." If a best candidate point falls outside some criteria, it is labeled as suspect. This label is removed and the point either included or rejected by looking at its position in the context of point positions in future projections. The following provides specifics for this process.

In some embodiments, the tracking component of method 250, steps 266-352, may be performed in either the direction of increasing projection number or that of decreasing projection number. In the latter case, it should be understood that references to "next projection" and "previous projection" and other terms relating to sequencing are relative to the direction of processing.

Figure 29:
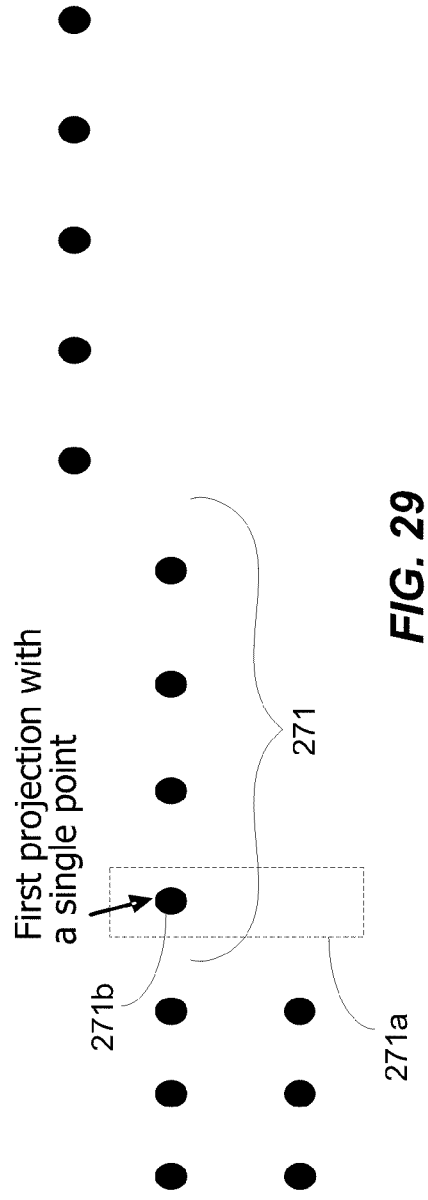
FIG. 29 is a graphical illustration of a synchronization process of an example candidate marker point list.

Returning to FIG. 24B, after processing the candidate point list at step 262, the method 250 creates an empty good point list for the physical marker (step 264). As described in more detail below, the good point list is populated with marker points identified in the projection images that have a high likelihood of being associated with the physical marker. The first step is synchronization (steps 266-270). The method 250 examines the candidate list, one projection at a time (e.g., starting from the first projection image) until a defined number of sequential projection images, such as 3, are found, where each image has a single candidate point in the candidate point list (step 266). The point associated with the first projection image in the detected sequence of projection images is labeled as the "reference good point" or reference point (step. 268). In addition, the method 250 adds this point to the good point list (step 270). FIG. 29 graphically represents the synchronization process on an example candidate point list. As shown in FIG. 29, the candidate point list includes a sequence 271 of three sequential projection images, where each image in the sequence 271 has only one point in the candidate point list. In the synchronization process, the first projection image in the detected sequence (labeled 271a) contains the single candidate point 271b which is labeled as the reference good point (step 268) and added to the good point list (step 270).

After synchronization has been obtained, the method 250 then moves to the "next" projection image in the sequence (step 272). In some embodiments, the method 250 will use the projection image found in the synchronization process and proceed first backward then forward from this point. The backward processing will proceed either until a projection having a point in the good point list is reached or, in the case where this is the first synchronization, to the first projection. The forward process will proceed until either the last projection is reached or until synchronization is lost. Again, when processing sequential projections, the definition of "next" will depend on whether processing is forward or backward.

Figure 30:
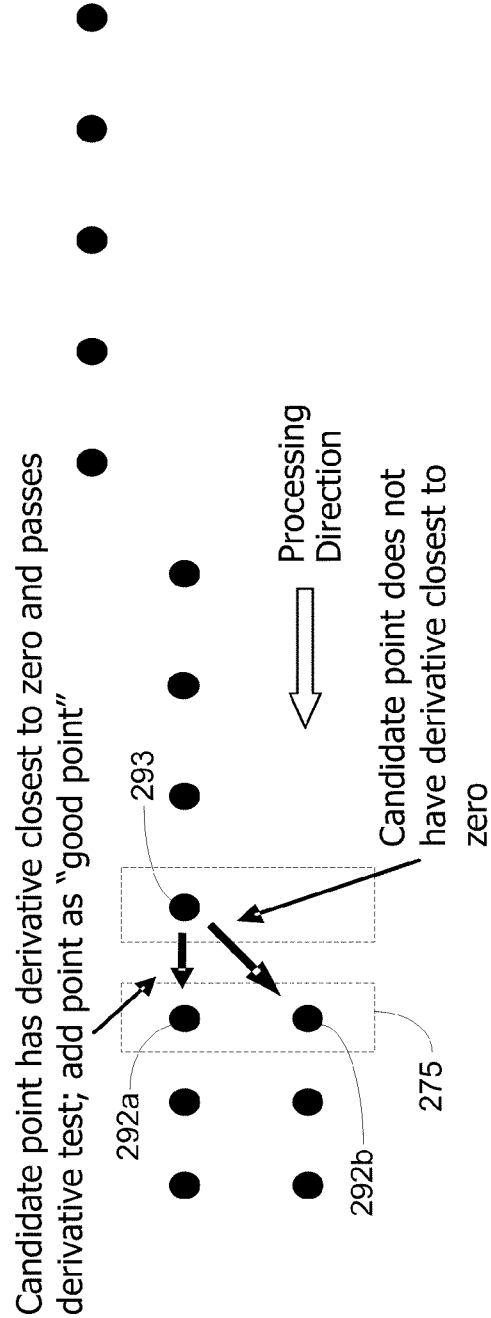
FIG. 30 is a graphical illustration of processing a "next" projection image when the "next" projection image includes two or more candidate marker points.

After moving to the next projection image, the method 250 determines how many candidate points are in that projection image (step 274). In some embodiments, there are two categories of results for step 274. The next projection image can include one or more candidate points or zero candidate points. FIG. 30 illustrates a situation where a next projection image 275 has two candidate points. FIG. 31 illustrates a situation where a next projection image 275 has only one candidate point, and FIG. 32 illustrates a situation where a next projection image 275 has no candidate points.

Returning to FIGS. 24B and 24C, if the next projection image has one or more candidate points, the method 250 determines the derivative of the U and V positional error with respect to θ (projection angle) between each candidate point in the next projection image and the most recently-added "good point" in the good point list (step 276). This derivative represents, in effect, the flatness of the line connecting two points as in FIG. 27. A zero derivative means that the amount of error between actual and theoretical has not changed between two images.

Next, the method 250 selects the candidate point associated with the derivative closest to zero (step 278) and adds this point to the good point list (step 280). If there is only a single candidate point, this point is chosen. Because the candidate point list was flattened to remove all effects except error (e.g., caused by patient movement or measurement noise), a large variance in the position error derivative between marker points in two adjacent projections may indicate (1) that a structure or object in an image has been erroneously defined as a marker or (2) that the marker point is actually associated with a different physical marker.

Therefore, two markers in the candidate point list that are associated with adjacent projection images and have a derivative close to zero are likely to be adjacent markers associated with the same physical marker. For example, as shown in FIG. 30, the next projection image 275 includes two candidate points 292a, 292b. The derivative between the reference "good point" 293 and the candidate point 292a is closer to zero than the derivative between the reference good point 293 and the candidate point 292b. Therefore, the candidate point 292a will be selected at step 278. As another example, as shown in FIG. 31, the next projection image 275 includes one candidate point 292a. The error derivative between the reference good point 293 and the candidate point 292a is calculated and the candidate point 292a is added to the good point list as a good point at step 280.

After selecting the candidate point associated with the derivative closest to zero, the method 250 determines if the candidate point's derivative passes a derivative test (step 282). The derivative test may include determining if the derivative has a value that differs from zero by more than a predetermined amount, such as 0.02 mm. If it does not, the candidate point passes the derivative test and the method 250 labels the point as the reference good point (step 284). If the point does not pass the derivate test, the method 250 labels the point as a "suspect point" (step 286). This newly added point is used to process the candidate points in the subsequent projection image.

The predetermined amount for the derivative test can be set and changed to modify the sensitivity of the method 250. For example, the predetermined amount can be set to a larger value in order to allow fewer suspect points to be added to the good point list, which may increase the amount of marker points ultimately mapped to a particular physical marker. In some embodiments, the derivative test can vary based on the number of candidate points in the next projection image, whether the good point list includes a suspect point, etc. In some embodiments, points labeled as suspect may not be considered for future processing but rather always considered bad and not added to the good point list. In these cases, the associated projection would have zero points.

Returning again to step 274 of FIG. 24B, if the next projection image does not include any candidate points, the method 250 skips the next projection image and continues to use the most recently-added reference good point (and the most recently-added suspect point if applicable) to process candidate points in the subsequent projection image (step 292). For example, as shown in FIG. 32, the next projection image 275 does not include any candidate points. Therefore, the method 250 skips the next projection image 275 and continues to use the most-recently added reference good point 293 (i.e., from the current projection image 295) to process the candidate point(s) (e.g., a candidate point 296a) in the subsequent projection image 297.

A suspect point can exist either because measurement noise causes misplacement of a particular point or because patient or unplanned gantry motion has caused actual movement in the physical marker. For proper motion correction, it is desirable to reject points related to the former and include points related to the latter. The handling of suspect points addresses these motion correction goals. Basically, the implementation of schemes for handling suspect points is based on the concept that a point that is suspect due to motion likely will have behavior reflected in multiple adjacent projections. Thus, once a suspect point has been flagged, final classification depends on examining future and possible additional past projection behavior.

Figure 24C:
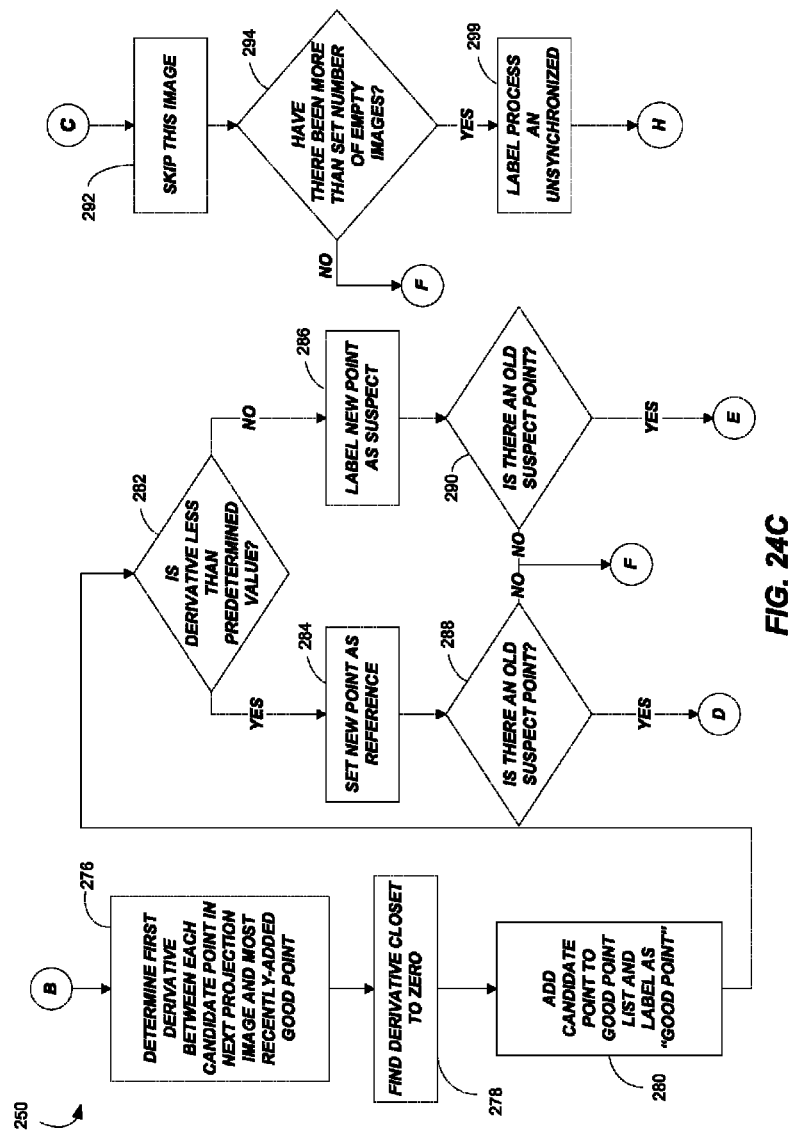
Figure 24D:
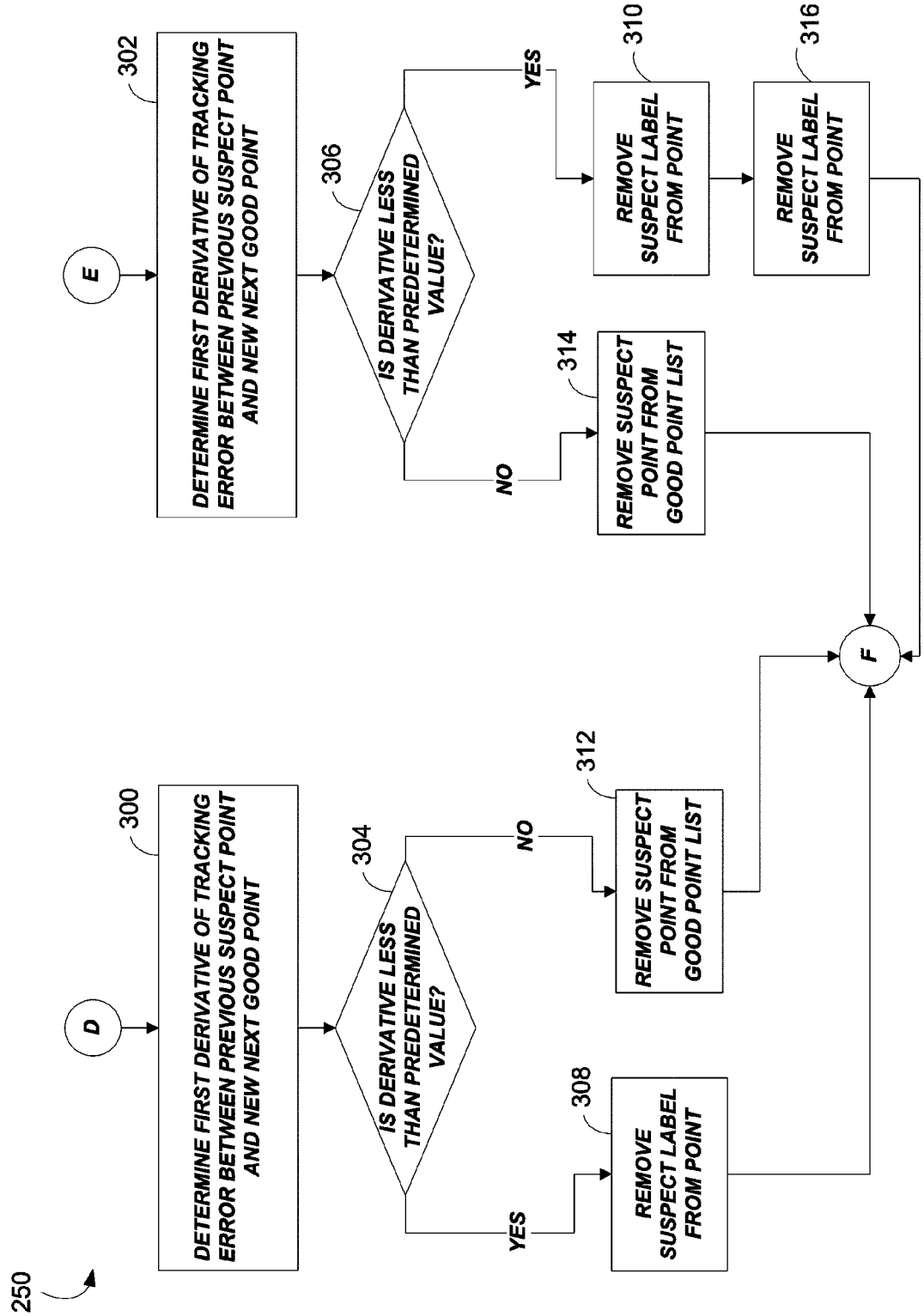
Figure 24E:
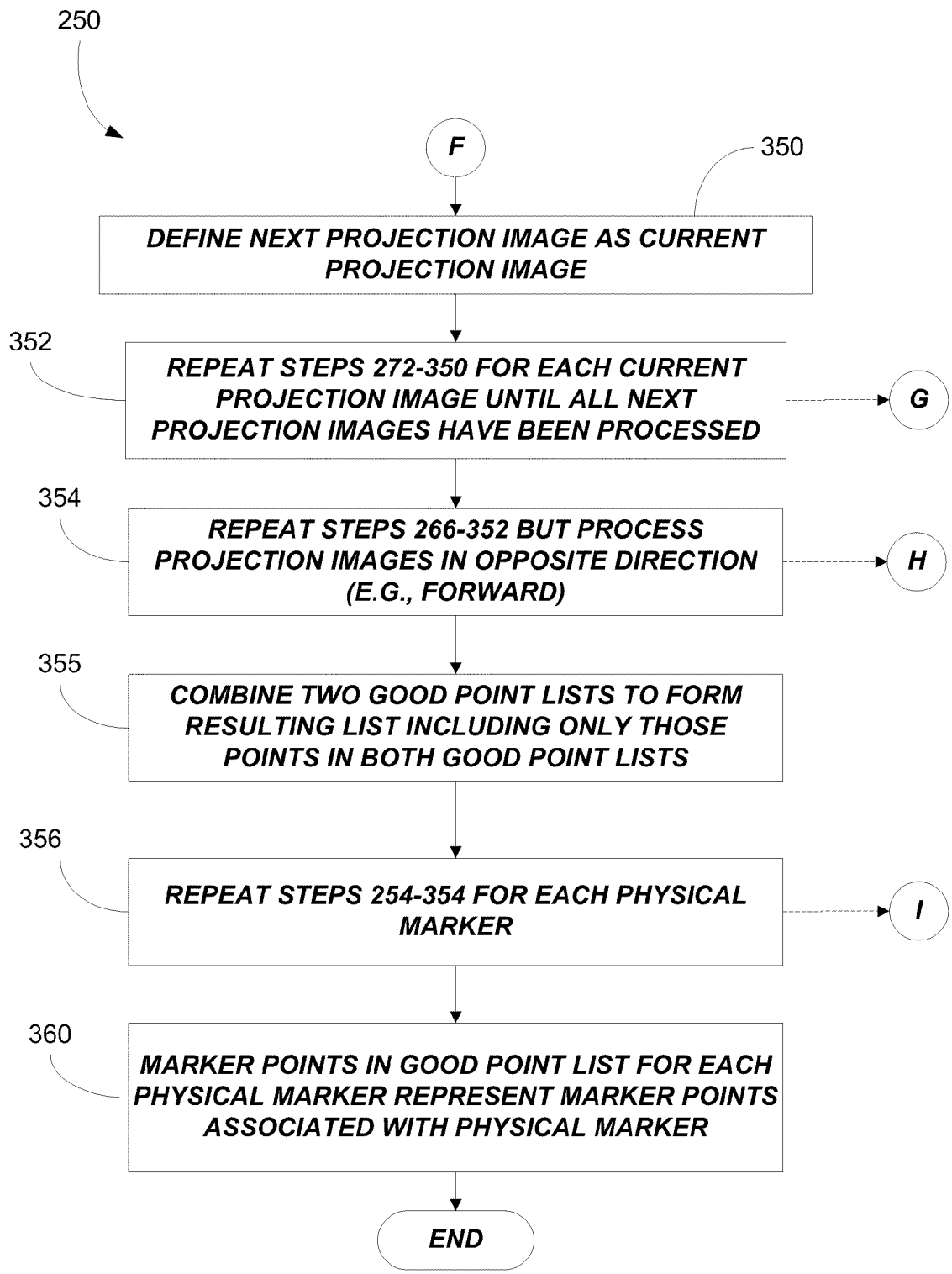

As referred to above, if the method 250 determines in steps 288 or 290 that there is a previous suspect point in the good point list (also referred to as an old suspect point), and the next projection image has one or more candidate points, special processing is required (see steps 300 and 302 in FIG. 24D). If so, the error derivative is formed between the suspect point and the most recently added point in the good point list (step 300 and 302). After forming the derivative associated with the suspect point, the method 250 determines if this derivative passes a derivative test (steps 304 and 306). The derivative test may include determining if the derivative has a value that differs from zero by more than a predetermined amount, such as 0.02 mm. If the derivative differs by less than the predetermined value, the suspect point is said to pass the derivative test. If the derivative differs by the same or greater than the predetermined value, the suspect point is said to fail the derivative test. If this suspect point passes the derivative test, the suspect label is removed from the point (steps 308 and 310). If the suspect point fails the derivative test, this point is removed from the good point list (steps 312 and 314) since it has failed two derivative tests, one with the previous point and one with the succeeding point.

If the previous suspect point passes the derivative test and point most recently added to the good point list had failed its derivative test, this previous suspect point now becomes the reference good point in the processing of succeeding projections (step 316). In this case, it is assumed that motion had occurred and the previous suspect point now represents the best indication of the new marker position.

Figure 33:
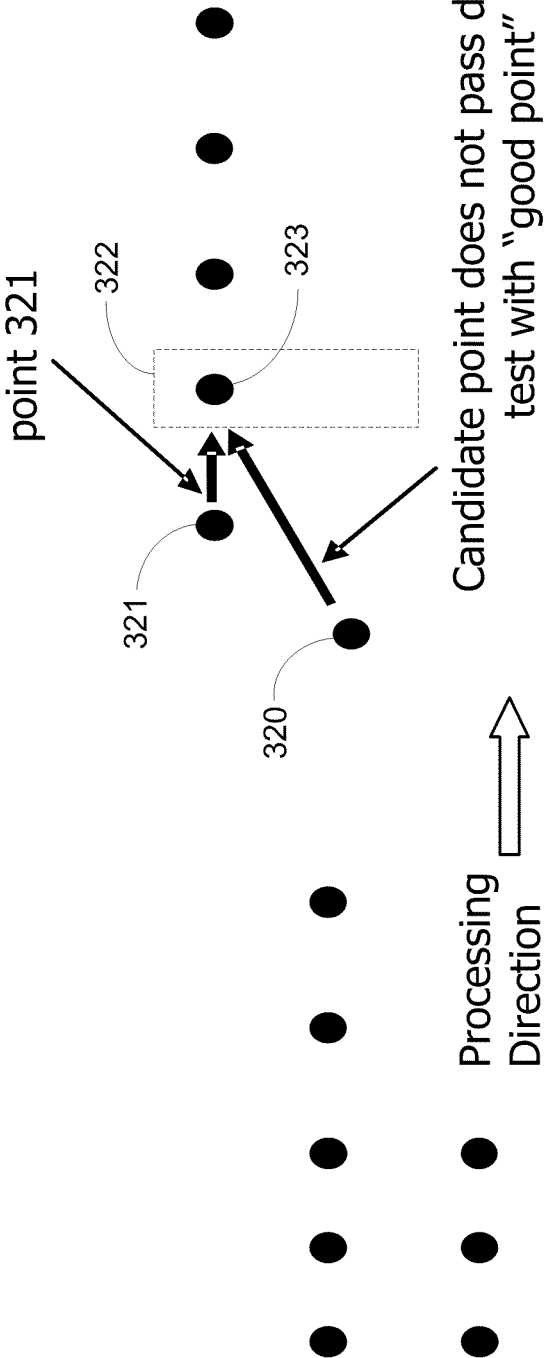
FIG. 33 is a graphical illustration of processing a "next" projection image when the good point list includes a good point and a suspect point.

For example, as shown in FIG. 33, the first derivative between the suspect point 321 and the candidate point 323 of projection image 322 is closest to zero and passes the derivative test. In addition, the corresponding first derivative between the good point 320 and the candidate point 323 fails the derivative test. Therefore, the suspect point 321 has its suspect label removed at step 310. The previously labeled suspect point, 321, will be used as the reference point for processing the next projection image (step 316).

There are a number of alternative embodiments of point tracking, many dealing with alternative ways of handling suspect points. In one, the method 250 is configured to only accept or re-label suspect points as good points if they have an error derivative with a candidate point that is closer to zero than the corresponding derivative with the reference good point for a predetermined number of sequential projection images greater than one. For example, the method 250 may determine whether, for three projection images in a row, the derivative between the suspect point and a candidate point is closer to zero than the corresponding derivative between the reference good point and the candidate point. If so, the method 250 re-labels the suspect point as a good point. The number of required projection images for accepting a suspect may be set and modified to change the sensitivity of the method 250 (i.e., the number of suspect points that ultimately get accepted as good points). In another alternative embodiment, any suspect points could be immediately removed from any further consideration. In such cases, there might be more reliance on resynchronization. In another embodiment, a suspect point flag would replace the labeling of individual points as suspect. In this case, the processing performed with the suspect point flag is set might be different depending on whether the candidate point list has a single point or more than one point.

If more than a particular number of projections, such as five, have no candidate points as determined in step 294, the processing is declared to have lost synchronization (step 299). In these cases, the synchronization process described above is repeated to regain synchronization.

As shown in FIGS. 24C and 24D, after processing the candidate point(s) in the next projection image, the method 250 defines the next projection image as the new current projection image (step 350) and repeats steps 272-350 (i.e., those steps applicable) for the new current projection image. This process is repeated until all the projection images in one direction from the initial current projection image have been processed as the "next projection image" (e.g., the first projection image is reached and processed as the next projection image) (step 352).

In some embodiments, the method 250 projection image steps 266-352 may be completely performed twice, once going from the lowest projection number to the highest and once going from the highest projection number to the lowest with each direction generating a separate good point list (step 354). Once the point lists are generated, they are combined projection-by-projection into a new list with any points not in both original lists eliminated (step 355). This combination step insures that any points included in the final good point list have a higher likelihood of being correct. FIGS. 30-32 illustrate processing projection images in a backward or reverse direction. FIG. 33 illustrates processing projection images in a forward direction.

After the projection images have been processed in either direction, the method 250 repeats steps 254-354 for each physical marker (step 356). For example, if nine physical markers were placed on the patient before the scan, the method 250 repeats steps 254-354 for each of the nine physical markers. After steps 254-354 have been performed for each physical marker, the method 250 has created a good point list for each physical maker and each good point list includes "good points" representing those marker points identified in the projection images that have the highest likelihood of being associated with a particular physical marker (step 360). Each good point list can include only zero or one marker point from each projection image that is associated with a particular physical marker. The "good points" in the good point lists can be used to extract patient motion information. For example, the expected locations of a physical marker reflected as marker points through the sequence projection images can be compared to the actual locations of the markers associated with the physical marker through the sequence projection images to determine the amount of patient movement.

One general challenge is that if physical markers are positioned close to each other (e.g., closer together than the range allowed for patient movement), it may be difficult to properly assign markers to a particular physical marker. This can be avoided by ensuring that the physical markers are separated by a proper distance when they are placed on the patient. Nonetheless, the method 250 is designed to handle, at least in part, situations where placement guidelines are not followed. If this situation occurs, it is possible that the tracking process might incorrectly assign marker points, a process referred to as "track jumping." Once one marker point "jumps" to a wrong track, there may not be a good basis for jumping back to the correct track, unless a sequence of points in the new (and wrong) track are missing. While the method 250 can deal with missing points on a track of markers, excessive missing points can lead to track jumping. This possibility can be minimized by choosing a small range of candidate points for a physical marker's candidate point list (e.g., because of lower expectations of the amount of patient movement).

In addition, processing the projection images in both directions (e.g., forward and backward) can identify and eliminate track jumping. For example, by comparing the results of processing the projection images in the forward direction to the results of processing the projection images in the backward direction, the method 250 can identify extended length differences, which are an indication of tracking problems. Another way to identify tracking problems is to compare the good point lists for different physical markers. If two good point lists include more than a few (e.g., one or two) of the same markers, the method 250 can detect and correct an incorrect tracking problem. However, with reasonable marker point detection and physical markers that are separated by approximately one centimeter or more, track jumping is usually non-existent with the method 250.

Although the marker point identification method 60, the marker point sub-pixel localization method 110, the physical marker 3D localization method 160, and the marker point mapping method 250 have been described in connection with CB CT imaging, the methods are also useful for CT, MRI, ultrasound, other forms of medical imaging, and forms of non-medical imaging, such as photography. For example, the marker point identification method 60 may be used in situations where an object (e.g., a small object) of a well-defined shape needs to be quickly isolated from a complex background. In addition, although the marker point identification method 60 has been described for use with circular or spherically-shaped markers, the method 60 may be used for marker points of other well-defined shapes. For example, steps 86 and 88 of step 80 (part of method 60) may be modified to recognize other shapes. The method 60 may also use well-defined anatomic objects internal to the patient as markers. Furthermore, the method 60 may be used as a starting point for extracting anatomical landmarks by searching for the general shape of a particular landmark.

Similarly, the marker point sub-pixel localization method 110 may be applied to any arbitrarily-shaped marker as long as the characteristics of the shape are known and the general orientation of the marker in a particular image can be ascertained. Various approaches can be used to ascertain the general orientation of a marker. For example, the marker point can be evaluated in general terms using its extensions in one (or two) dimensions to help define the placement of the marker point profile in the other dimension. The marker point profile can then be processed with a simple first-moment calculation or a more elaborate curve fitting. In addition, an image shape can be compared to an atlas of shapes expected at different orientations and the appropriate one can be selected. Furthermore, reconstruction of CT image data can be used to produce a 3D image of a marker to determine its orientation before defining and fitting a proper curve function.

The marker point sub-pixel localization method 110 also has other potential applications in medical imaging and non-medical imaging. For example, in dental imaging, the method 110 may be used to place brackets in an orthodontic treatment, where the positions of the brackets could be evaluated to a precision of approximately 100 micrometers or better. The method 110 may also be used for accurate registration of images acquired at different times but with the same external or internal markers. Similarly, the basic approach of the marker 3D localization method 160 may be used in markerless CT scanning and other non-CT scanning application, such as astronomy.

The physical marker mapping method 250 also has other potential applications than just patient motion tracking. For example, the method 250 can be used to create a dynamic calibration for gantries that experience non-ideal rotation. In this case, the method 250 would be applied to a fixed phantom containing embedded markers. This application would be particularly useful for CT systems with x-ray image intensifiers (sometimes referred to as C-Arm scanning settings). Furthermore, the method 250 can generally be used with systems where an object has an "ideal" progression that might, in actual practice, not be ideal.

In addition, the methods described above can use various data processing techniques. For example, the marker point mapping method 250 may use various lists and combinations of lists or tables for tracking candidate points, good points, and suspect points. For example, the method 250 may create a candidate point list and remove non-good points rather than create a separate good point list. In addition, the method 250 may create one or more lists of points and use flags or bits to distinguish between candidate points, good points, bad points, and suspect points.

Also, although FIG. 2 illustrates the ROM module 46 as storing separate modules (e.g., 50, 52, 54, 56, etc.), in some embodiments, these modules are combined and distributed into one or multiple modules stored in the ROM module 46, other memory modules, or combinations thereof. For example, in some embodiments, the same module performs the marker identification method and the marker sub-pixel localization method. In addition, the ROM module 46 can include other modules for performing functions other than those functions described above. In some embodiments, the modules may be stored on a hard-disk, flash, or other semi-permanent medium and transferred to RAM for execution.

Thus, the invention provides, among other things, methods and systems for identifying marker points in an image, determining a sub-pixel center point of a marker point identified in an image, determining 3D coordinates for a marker identified in an image, and mapping marker points to particular physical markers placed on a patient. Various features and advantages of the invention are set forth in the following claims.

What is claimed is:

1. A method of associating marker projections with radiopaque markers affixed to a patient, the method executed by an imaging system including a scanner, a computer with an electronic processing unit, and a memory module storing a module executable by the electronic processing unit, the method comprising:

generating, with the scanner, a sequence of computer tomography projection frames comprising at least a first projection frame, wherein the first projection frame includes a first marker projection;

determining, with the electronic processing unit, an approximate 3D physical location in relation to the scanner of a first radiopaque marker affixed to a patient;

based at least on the approximate 3D physical location of the first radiopaque marker, calculating, with the electronic processing unit, a first expected marker projection location in the first projection frame, wherein the first marker projection and the first expected marker projection location are separated from each other by a first distance in at least one dimension;

based at least on the first distance being within an expected range, determining, with the electronic processing unit, that the first marker projection is a projection of the first radiopaque marker; and correcting for patient motion based at least on determining that the first marker projection is a projection of the first radiopaque marker.

2. The method of claim 1, wherein the step of determining the approximate 3D physical location of the first radiopaque marker comprises:

selecting a plurality of candidate 3D locations of the first radiopaque marker;

computing an error value of each of the plurality of candidate 3D locations, the step of computing an error value comprising:

for each frame of a plurality of frames in the sequence, determining an error between an expected projection location of the candidate 3D location and an actual projection location of the first radiopaque marker in the frame, and computing a sum of the errors determined in the step of determining an error; and selecting a candidate 3D location having a lowest sum error value of the computed error values.

3. The method of claim 1, wherein the first distance is in a first dimension, wherein the first marker projection and the first expected marker projection location are further separated from each other by a second distance in a second dimension, the method further comprising:

determining the first distance in the first dimension;

determining the second distance in the second dimension, wherein the step of determining whether the first marker projection is a projection of the first radiopaque marker is based on the first and second distances.

4. The method of claim 1, wherein the step of determining whether the first marker projection is a projection of the first radiopaque marker comprises:

if both the first marker projection and a second marker projection are near the first expected marker projection location, performing the steps of:

a. computing a trajectory of projections of the first radiopaque marker in a plurality of projection frames;

b. identifying which of the first and second marker projections is closer to the trajectory; and d. associating the identified marker projection with the first radiopaque marker.

5. The method of claim 1, wherein the radiopaque markers are affixed to the patient in a manner permitting relative motion between the radiopaque markers.

* * * * *